US005635493A

United States Patent [19]
Vournakis et al.

[11] Patent Number: 5,635,493
[45] Date of Patent: Jun. 3, 1997

[54] METHODS AND COMPOSITIONS FOR POLY-β-1-4-N-ACETYLGLUCOSAMINE CHEMOTHERAPEUTICS

[75] Inventors: John N. Vournakis, Hanover, N.H.; Sergio Finkielsztein, Chestnut Hill; Ernest R. Pariser, Belmont, both of Mass.; Mike Helton, Memphis, Tenn.

[73] Assignee: Marine Polymer Technologies, Inc., Danvers, Mass.

[21] Appl. No.: 471,545

[22] Filed: Jun. 6, 1995

Related U.S. Application Data

[63] Continuation-in-part of Ser. No. 347,911, Dec. 1, 1994, which is a continuation-in-part of Ser. No. 160,569, Dec. 1, 1993.

[51] Int. Cl.$^6$ ............................ A61K 31/73; C08B 37/08
[52] U.S. Cl. ........................... 514/55; 514/2; 514/8; 514/62; 536/20; 536/55.2
[58] Field of Search ............................ 514/55, 62, 2, 514/8; 536/20, 55.2

[56] References Cited

U.S. PATENT DOCUMENTS

| | | | |
|---|---|---|---|
| 3,988,411 | 10/1976 | Capozza | 264/184 |
| 3,989,535 | 11/1976 | Capozza | 106/203 |
| 4,378,017 | 3/1983 | Kosugi et al. | 424/499 |
| 4,532,134 | 7/1985 | Malette et al. | 514/55 |
| 4,749,620 | 6/1988 | Rha et al. | 428/402.2 |
| 5,008,116 | 4/1991 | Cahn | 424/491 |
| 5,071,977 | 12/1991 | Cassels et al. | 536/123 |
| 5,219,749 | 6/1993 | Bouriotis et al. | 435/227 |
| 5,229,123 | 7/1993 | Masubuchi et al. | 424/408 |

FOREIGN PATENT DOCUMENTS

| | | |
|---|---|---|
| 0543572 | 5/1993 | European Pat. Off. . |
| 0543572A | 5/1993 | European Pat. Off. . |
| 55-152705 | 11/1980 | Japan . |
| 62-288602 | 12/1987 | Japan . |
| 62288602 | 12/1987 | Japan . |
| 1038367 | 8/1966 | United Kingdom . |
| WO93/12875 | 7/1993 | WIPO . |

OTHER PUBLICATIONS

US Pharmacopeia XXII, 1991, Supplement 5, pp. 2702–2703.
Kurita, K. et al., 1990, "Preparation of soluble chitin derivatives and the modifications to branched chitins" Polym. Prep. (Am. Chem. Soc., Div. Polym. Chem.) 31:624–625.
US Pharmacopeia XXII, 1990, pp. 1415–1500.
Hirano, S., 1989, "Production and application of chitin and chitosan in Japan,"in Chitin and Chitosan, Skjak–Braek, Anthonsen, and Sanford, eds. Elsevier Science Publishing Co., pp. 37–43.
Maresh, G. et al., 1989, "Hydroxypropylation of chtiosan," in Chitin and Chitosan, Skjak–Braek, Anthonsen, and Sanford, eds. Elsevier Science Publishing Co., pp. 389–395.

Austin, P.R. and Sennett, S., 1986, "Dry chitosan salts and complexes of aliphatic carboxylic acids," in Chitin in Nature and Technology, Muzzarelli et al., eds. Plenum Press, New York, pp. 279–286.
Komai, T. et al., 1986, "Biomedical evaluation of acylated chitins as coating materials," in Chitin in Nature and Technology, Muzzarelli et al., eds. Plenum Press, New York, pp. 497–506.
Nishi, N. et al., 1986, "Preparation and characterization of phosphorylated chitin and chitosan," in Chitin in Nature and Technology, Muzzarelli et al., eds. Plenum Press, New York, pp. 297–299.
Domard, A., 1986, "Circular dichroism study on N–acetylglucosamine oligomers," Int. J. Macromol. 8:243–246.
Tokura, S. et al., 1983, "Studies on chitin VIII. Some properties of water soluble chitin derivatives," Polym. J. 15:485–489.
Davis, M. and Preston, J.F., 1981, "A simple modified carbodiimide method for conjugation of small molecular weight compounds to immunoglobulin G with minimal protein crosslinking," Anal. Biochem. 116:402–407.
Hirono, S. et al., 1981, "SEM ultrastructure studies of N–acyl–and N–benzylidene–chitosan membranes," J. Biomed. Mat. Res. 15:903–911.
Hirano, S. et al., 1976, "Selective N–acylation of chitosan," Carbohydrate Research 47:315–320.
Schweiger, R.G., 1972, "Polysaccharide sulfates I. Cellulose sulfate with a high degree of substitution," Carbohydrate Res. 21:219–228.
Noguchi, J. et al., 1969, "Chitosan epichlorohydrin anion exchange resin with primary amine as absorption site," Kogyo Kagaku Zasshi 72:796–799.
McLachlan, A.G. et al, 1965, "Studies on the chitin (chitin: poly–N–acetylglucosamine) fibers of the diatom thalassiosira fluviatilis hustedt," Can. J. Botany 43:707–713.
Schorigin, P. and Hait, E., 1934, Chem. Ber. 67:1712–1714.
Falk et al. Can. J. Chem. 1966, 44, 2269–2281.
McLachlan and Craigie Some Contemp. Stud. Mar. Sci. 1966, 511–517.

(List continued on next page.)

*Primary Examiner*—John Kight
*Assistant Examiner*—Kathleen Kahler Fonda
*Attorney, Agent, or Firm*—Pennie & Edmonds

[57] ABSTRACT

The present invention relates to a purified, easily produced poly-β-1→4-N-acetylglucosamine (p-GlcNAc) polysaccharide species useful in drug compositions. The p-GlcNAc of the invention is a polymer of high molecular weight whose constituent monosaccharide sugars are attached in a β-1→4 conformation, and which is free of proteins, and substantially free of single amino acids, and other organic and inorganic contaminants. In addition, derivatives and reformulations of p-GlcNAc are described. The present invention further relates to methods for the purification of the p-GlcNAc of the invention from microalgae, preferably diatom, starting sources. Still further, the invention relates to methods for the derivatization and reformulation of the p-GlcNAc. Additionally, the present invention relates to the uses of pure p-GlcNAc, its derivatives, and/or its reformulations.

16 Claims, 58 Drawing Sheets

OTHER PUBLICATIONS

Bodemeier et al. *Pharm. Res.* 1989, 6(5), 413–417.

Blackwell *Meth. Enz.* 1988, 161, 435–442.

Blackwell et al. *J. Mol. Biol.* 1967, 28, 383–385.

Thanoo et al. *J. Pharm. Pharmacol.* 1992, 44, 283–286.

Hirano et al., 1990, "The Regulation of Serum Cholesterol Level by Oral Administration of Chitosan in Rabbits," in *Proceedings of The International Symposium on Chitin Derivatives in Life Sciences,* Oct. 5–7., pp. 115–120.

Zielinski and Aebischer, 1994, "Chitosan as a matrix for mammalian cell encapsulation", Biomaterials 15(13): 1049–1056.

Vournakis et al., 1994, "Isolation & characterization of pure poly–N–acetylglucosamine: Controlled enzymatic deacetylation and formulation for tissue engineering applications", J Cell Biochem Suppl ), No. 18C, p. 283 Abstract PZ 313, Keystone Symposium on Tissue Engineering.

Polk, A. et al., 1994, J. of Pharmaceutical Sciences, 83(2):178–185.

Matthew et al., 1993, "Complex coacervate microcapsules for mammalian cell culture and artificial organ development", Biotechnol Prog 9(5):510–519.

Groboillot et al., 1993, "Membrane formation by interfacial cross–linking of chitosan for microencapsulation of *Lactococcus lactis*" Biotechnology and Bioengineering 42(10):1157–1163.

Aebisher, P. et al., 1993, in "Fundamentals of Animal Cell Encapsulation and Immobilization", CRC Press, pp. 197–224.

Mireles, C. et al., 1992, in "Advances in Chitin and Chitosan", Brine, C.J. et al., eds., Elsevier Publishers, Ltd., pp. 506–515.

Thanoo et al., 1992, "Cross–linked chitosan microspheres: Preparation and evaluation as a matrix for the controlled release of pharmaceuticals", J. Pharm. Pharmacol., 44, 283–286.

Dong, C. and Rogers, J.A., 1991, Journal of Controlled Release, 17:217–224.

Yoshioke, T. et al., 1990, Biotechnol Bioeng. 35:66–72.

Kurita, K. et al., 1990, "Preparations of soluble chitin derivatives and the modifications to branched chitins" Polym. Prep. (Am. Chem. Soc., Div. Polym. Chem.) 31:624–625.

Kurita, K. and Inoue, S., 1989, in "Chitin and Chitosan", Skjak–Braek et al., eds., Elsevier Science Publishing Co., Inc., pp. 365–372.

Bedemeier et al., 1989, Pharm. res., 6(5), 413–417.

Blackwell, 1988, Meth. Enz., 161, 435–442.

Staros, J.V., et al., 1986, "Enhancement by N–hydroxysulfosuccinate of water soluble carbodiimide mediated coupling reactions" Anal. Biochem. 156:220–222.

Hwang, C. et al., 1985, "Encapsulation with Chitosan: Transmembrane Diffusion of Proteins in Capsules," in Muzzarelli, R. et al., eds., Chitin in Nature and Technology, Plenum Press, pp. 389–396.

Vahouny, G.V., 1983, Journal of Clinical Nutrition, 38:278–284.

Blackwell et al., 1967, J. Mol. Biol., 28, 383–385.

Falk et al., 1966, "Studies on chitin ($\beta$–(1→4)–linked 2–acetamido–2–deoxy–D–glucan) fibers of the diatom thalassiosira fluviatilis hustedt", Can. J. Chem., 44, 2269–2281.

McLachlan and Craigie 1966, Some Contemp. Stud. Mar. Sci., 511–517.

McLachlan, A.G. et al, 1965, "Studies on the chitin (chitin:poly–N–acetylglucosamine) fibers of the diatom thalassiosira fluviatilis hustedt," Can. J. Botany 43:707–713.

| PEAK | %RF | | AMPLITUDE | %SIGMA | AREA | %TOTAL | | RATIO | | RATIO |
|---|---|---|---|---|---|---|---|---|---|---|
| 1 | 5 | C=O | 0.087 | 0.29 | 1.304 | 1.674 | | | | 5.609 |
| 2 | 6 | C=O | 0.146 | 0.38 | 2.855 | 3.664 | 4.159 | 1.759 | | 2.562 |
| 3 | 47 | C1 | 0.563 | 0.38 | 11.153 | 14.314 | 11.153 | 0.656 | | 0.656 |
| 4 | 59 | C4 | 0.452 | 0.32 | 7.41 | 9.51 | 7.410 | 0.987 | | 0.987 |
| 5 | 63 | C5 | 0.311 | 0.49 | 7.906 | 10.147 | 7.906 | 0.925 | | 0.925 |
| 6 | 64 | C3 | 1.195 | 0.16 | 9.816 | 12.598 | | | | 0.745 |
| 7 | 65 | C3 | 0.533 | 0.4 | 11.11 | 14.259 | 20.926 | 0.350 | | 0.658 |
| 8 | 72 | C6 | 0.148 | 1.1 | 8.419 | 10.805 | | | | 0.869 |
| 9 | 73 | C6 | 0.21 | 0.18 | 1.98 | 2.541 | 10.399 | 0.703 | | 3.694 |
| 10 | 74 | C2 | 0.026 | 0.2 | 0.27 | 0.346 | | | | 27.089 |
| 11 | 75 | C2 | 0.227 | 0.72 | 8.38 | 10.755 | 8.650 | 0.846 | | 0.873 |
| 12 | 94 | CH3 | 0.377 | 0.38 | 7.314 | 9.387 | | | | 1.000 |

FIG. 5A

| PEAK | %RF | | AMPLITUDE | %SIGMA | AREA | %TOTAL | | RATIO | RATIO |
|---|---|---|---|---|---|---|---|---|---|
| 1 | 4 | C=0 | 0.803 | 0.42 | 18.08 | 14.5 | 18.080 | 0.8308 | 0.831 |
| 2 | 27 | C1 | 0.594 | 0.53 | 16.959 | 13.6 | 16.959 | 0.8857 | 0.886 |
| 3 | 37 | C4 | 2.073 | 0.28 | 30.787 | 24.68 | 30.787 | 0.4879 | 0.488 |
| 4 | 39 | C5 | 0.581 | 0.48 | 14.915 | 11.96 | 14.915 | 1.007 | 1.007 |
| 5 | 51 | C6 | 0.096 | 1.06 | 5.504 | 4.413 | | | 2.729 |
| 6 | 54 | C6 | 0.324 | 0.56 | 9.767 | 7.831 | 15.271 | 0.9836 | 1.538 |
| 7 | 57 | C2 | 0.197 | 0.55 | 5.848 | 4.689 | | | 2.568 |
| 8 | 59 | C2 | 0.226 | 0.64 | 7.843 | 6.289 | 13.691 | 1.0971 | 1.915 |
| 9 | 95 | CH3 | 0.363 | 0.77 | 15.02 | 12.04 | 15.020 | | 1.000 |

PROTOTYPE 1: DAY 0

PROTOTYPE 1: DAY 14

PROTOTYPE 1: DAY 21

PROTOTYPE 3A: DAY 0

PROTOTYPE 3A: DAY 14

METHODS AND COMPOSITIONS FOR POLY-β-1-4-N-ACETYLGLUCOSAMINE CHEMOTHERAPEUTICS

This is a continuation-in-part of Ser. No. 08/347,911, filed Dec. 1, 1994, which is continuation-in-part of Ser. No. 08/160,569, filed Dec. 1, 1993, which is incorporated herein by reference in its entirety.

TABLE OF CONTENTS
1. INTRODUCTION
2. BACKGROUND OF THE INVENTION
3. SUMMARY OF THE INVENTION
4. BRIEF DESCRIPTION OF THE FIGURES
5. DETAILED DESCRIPTION OF THE INVENTION
   5.1. p-GlcNAc
   5.2. METHODS OF PRODUCING MICROALGAL SOURCES OF p-GlcNAc
      5.2.1. MICROALGAL SOURCES OF p-GlcNAc
      5.2.2. METHODS FOR GROWING DIATOMS
   5.3. METHODS FOR ISOLATION, PURIFICATION, AND CONCENTRATION OF p-GlcNAc FIBERS
      5.3.1. MECHANICAL FORCE METHOD FOR PREPARATION OF PURE p-GlcNAc
      5.3.2. CHEMICAL/BIOLOGICAL METHOD FOR PURIFICATION OF p-GlcNAc
   5.4. DERIVATIZATION OF p-GlcNAc
   5.5. REFORMULATIONS
   5.6. USES
      5.6.1. BIOMEDICAL USES OF p-GlcNAc MATERIALS
         5.6.1.1. DRUG IMMOBILIZATION/DELIVERY USES
         5.6.1.2. p-GlcNAc CELL ENCAPSULATION USES
         5.6.1.3. UTILIZING p-GlcNAc MATERIALS FOR THE PREVENTION OF POST-SURGICAL ADHESIONS
         5.6.1.4. BIODEGRADABLE p-GlcNAc BARRIERS
         5.6.1.5. OTHER BIOMEDICAL USES OF p-GtcNAc MATERIALS
      5.6.2. AGRICULTURAL USES OF p-GlcNAc MATERIALS
      5.6.3. NUTRITION/FOOD INDUSTRY USES OF p-GlcNAc MATERIALS
      5.6.4. COSMETIC USES OF p-GlcNAc MATERIALS
      5.6.5. CHEMICAL ENGINEERING APPLICATIONS OF p-GlcNAc MATERIALS
6. EXAMPLE PHYSICAL CHARACTERIZATION OF PREPARATIONS OF PURE p-GlcNAC
   6.1. MATERIALS AND METHODS
   6.2. RESULTS
      6.2.1. CD ANALYSIS
      6.2.2. IR SPECTRA ANALYSIS
7. EXAMPLE: PURIFICATION OF p-GlCNAC USING THE MECHANICAL FORCE PURIFICATION METHOD
   7.1. MATERIALS AND METHODS/RESULTS
8. EXAMPLE: PURIFICATION OF p-GlcNAC USING THE BIOLOGICAL/CHEMICAL PURIFICATION METHOD
   8.1. MATERIALS AND METHODS/RESULTS
9. EXAMPLE: p-GlcNAc DEACETYLATION
10. EXAMPLE: p-GlcNAc BIOCOMPATIBILITY
    10.1. MATERIALS AND METHODS
       10.1.1. ELUTION TEST
       10.1.2. INTRAMUSCULAR IMPLANTATIONS
       10.1.3. INTRACUTANEOUS INJECTIONS
       10.1.4. SYSTEMIC INJECTIONS
    10.2. RESULTS
       10.2.1. ELUTION TEST
       10.2.2. INTRAMUSCULAR IMPLANTATIONS
       10.2.3. INTRACUTANEOUS TEST
       10.2.4. SYSTEMIC TEST
11. EXAMPLE: p-GlcNAc REFORMULATION
12. EXAMPLE: CELL ATTACHMENT TO p-GlcNAc
    12.1. MATERIALS AND METHODS
    12.2. RESULTS
13. EXAMPLE: p-GlcNAc/COLLAGEN HYBRIDS
    13.1. MATERIALS AND METHODS
    13.2. RESULTS
14. EXAMPLE: NMR CHARACTERIZATION OF PURE PREPARATIONS OF p-GlcNAc
    14.1. MATERIALS AND METHODS
    14.2. RESULTS
15. EXAMPLE: SYNTHESIS AND BIOLOGICAL CHARACTERIZATION OF CONTROLLED PORE SIZE THREE-DIMENSIONAL p-GlcNAc MATRICES
    15.1. MATERIALS AND METHODS
    15.2. RESULTS
16. EXAMPLE: CELL GROWTH ON THREE-DIMENSIONAL POROUS p-GlcNAc MATRICES
    16.1. MATERIALS AND METHODS
    16.2. RESULTS
17. EXAMPLE: p-GlCNAc SUCCESSFULLY REDUCES AND PREVENTS POST-SURGICAL-ADHESIONS
    17.1. MATERIALS AND METHODS
    17.2. RESULTS
18. EXAMPLE: BIODEGRADABILITY OF p-GlcNAc MATERIALS
    18.1. MATERIALS AND METHODS
    18.2. RESULTS
19. EXAMPLE: p-GlcNAc HEMOSTASIS STUDIES
    19.1. MATERIALS AND METHODS
    19.2. RESULTS
20. EXAMPLE: p-GlcNAc DRUG DELIVERY SYSTEMS
    20.1. MATERIALS AND METHODS
    20.2. RESULTS
       20.2.1. p-GlcNAc-LACTATE 5'FU
       20.2.2. p-GlcNAc-LACTATE MITO
       20.2.3. p-GlcNAc MEMBRANE 5'FU
    20.3. CONCLUSION
21. EXAMPLE: FURTHER p-GlcNAc DRUG DELIVERY SYSTEMS
    21.1. MATERIALS AND METHODS
    21.2. RESULTS
    21.3. CONCLUSION
22. EXAMPLE: WOUND. HEALING STUDIES
    22.1. MATERIALS AND METHODS
    22.2. RESULTS
23. EXAMPLE: TAXOL FORMULATION
    23.1. MATERIALS AND METHODS

INTRODUCTION

The present invention relates, first, to a purified, easily produced poly-p-β-1→4-N-acetylglucosamine (p-GlcNAc)

polysaccharide species. The p-GlcNAc of the invention is a polymer of high molecular weight whose constituent monosaccharide sugars are attached in a β-1→4 conformation, and which is free of proteins, and substantially free of single amino acids, and other organic and inorganic contaminants. In addition, derivatives and reformulations of p-GlcNAc are described. The present invention further relates to methods for the purification of the p-GlcNAc of the invention from microalgae, preferably diatom, starting sources. Still further, the invention relates to methods for the derivatization and reformulation of the p-GlcNAc. Additionally, the present invention relates to the uses of pure p-GlcNAc, its derivatives, and/or its reformulations.

BACKGROUND OF THE INVENTION

There exists today an extensive literature on the properties, activities, and uses of polysaccharides that consist, in part, of p-GlcNAc. A class of such materials has been generically referred to as "chitin", while deacetylated chitin derivatives have been referred to as "chitosan". When these terms were first used, around 1823, it was believed that chitin and chitosan always occurred in nature as distinct, well-defined, unique, and invariant chemical species, with chitin being fully acetylated and chitosan being fully deacetylated compositions. It was approximately a century later, however, before it was discovered that the terms "chitin" and "chitosan" are, in fact, very ambiguous. Rather than referring to well-defined compounds, these terms actually refer to a family of compounds that exhibit widely differing physical and chemical properties. These differences are due to the products' varying molecular weights, varying degrees of acetylation, and the presence of contaminants such as covalently bound, species-specific proteins, single amino acid and inorganic contaminants. Even today, the terms "chitin" and "chitosan" are used ambiguously, and actually refer to poorly defined mixtures of many different compounds.

For example, the properties of "chitins" isolated from conventional sources such as crustacean outer shells and fungal mycelial mats are unpredictably variable. Such variations are due not only to species differences but are also due to varying environmental and seasonal effects that determine some of the biochemical characteristics of the "chitin"-producing species. In fact, the unpredictable variability of raw material is largely responsible for the slow growth of chitin-based industries.

No reports exist today in the scientific literature describing the isolation and production, from material sources, of pure, fully acetylated p-GlcNAc, i.e., a product or products uncontaminated by organic or inorganic impurities. While McLachlan et al. (McLachlan, A. G. et al., 1965, Can. J. Botany 43:707–713) reported the isolation of chitin, subsequent studies have shown that the "pure" substance obtained, in fact contained proteins and other contaminants.

Deacetylated and partially deacetylated chitin preparations exhibit potentially beneficial chemical properties, such as high reactivity, dense cationic charges, powerful metal chelating capacity, the ability to covalently attach proteins, and solubility in many aqueous solvents. The unpredictable variability of these preparations, as described above, however, severely limits the utility of these heterogenous compounds. For example, the currently available "chitins" and "chitosans" give rise to irreproducible data and to unacceptably wide variations in experimental results. Additionally, the available preparations are not sufficiently homogenous or pure, and the preparation constituents are not sufficiently reproducible for these preparations to be acceptable for use in applications, especially in medical ones. Thus, although extremely desirable, true, purified preparations of chitin and chitosan, whose properties are highly reproducible and which are easily manufactured, do not currently exist.

SUMMARY OF THE INVENTION

The present invention relates, first, to an isolated, easily produced, pure p-GlcNAc species. The p-GlcNAc of the invention is a polymer of high molecular weight whose constituent monosaccharides are attached in a β-1→4 conformation, and which is free of proteins, substantially free of other organic contaminants, and substantially free of inorganic contaminants.

The importance of the present invention resides in the fact that the problem of unpredictable raw material variability has been overcome. It is, for the first time, possible to produce, by simple means, and on a commercial scale, biomedically pure, p-GlcNAc of high molecular weight and consistent properties. The material produced in the present invention is highly crystalline and is produced from carefully controlled, aseptic cultures of one of a number of marine microalgae, preferably diatoms, which have been grown in a defined medium.

The present invention further describes derivatives and reformulations of p-GlcNAc as well as methods for the production of such derivatives and reformulations. Such derivatizations may include, but are not limited to polyglucosamine and its derivatives, and such reformulations may include, but are not limited to membranes, filaments, nonwoven textiles, sponges, gels and three-dimensional matrices. Still further, the present invention relates to methods for the purification of the p-GlcNAc of the invention from microalgae, preferably diatom, sources.

Additionally, the present invention relates to the uses of the purified p-GlcNAc, its derivatives, and/or its reformulations. Among these uses are novel commercial applications relating to such industries as the biomedical, pharmaceutical, cosmetic and agricultural industries, all of which require starting materials of the highest degree of purity. For example, the p-GlcNAc materials of the invention may be formulated to exhibit controllable biodegradation properties, and, further, may be used as part of slow drug delivery systems, as cell encapsulation systems, and as treatments for the prevention of post-surgical adhesions; and for the induction of hemostasis. For example, the p-GlcNAc materials of the invention exhibit properties that make them ideally suited for a large number of biomedical applications. Some of these properties include but are not limited to: high purity and composition consistency; biocompatibility; controllable biodegradability; and, an ability to immobilize and encapsulate agents, such as therapeutic agents, and cells. These properties are useful, for example, in the formulation of biodegradable barrier devices, improved drug formulations and cell based therapeutics.

The biodegradable barriers of the invention include p-GlcNAc based materials used as devices, for example, as temporary barriers which become resorbed by the body. This category of products include, but is not limited to, devices that prevent the formation of surgical adhesions, stop bleeding, and promote wound healing. Such biodegradable barriers can further be used as surgical space fillers, periodontal barriers or for soft tissue augmentation.

Improved drug formulations of the invention include p-GlcNAc based materials designed to deliver drugs. These new drug formulations are an improvement over traditional drug formulations, in that the drug formulations of the invention provide, for example, increased effectiveness, reduced toxicity and improved bioavailability. These improved drug formulations can be used in combination with many therapeutic agents including, but not limited to, chemotherapeutic agents, such as antitumor agents, as well as antibiotics, antibacterials, antifungals and anti-inflammatory drugs.

Additionally, the present invention relates to cell based therapeutics using p-GlcNAc based materials as a matrix for the encapsulation of cells. For example, p-GlcNAc/cell encapsulations may be used for the implantation of insulin-producing cells in the treatment of diabetes or dopamine-producing cells for the treatment of Parkinson's disease. The p-GlcNAc cell encapsulations of the invention can also be used for the delivery of cells to regenerate tissue such as, for example, skin, cartilage and bone.

BRIEF DESCRIPTION OF THE FIGURES

FIG. 5A. NMR analysis of p-GlcNAc purified using the chemical/biological purification method as described in Section 5.3.2, below. Chart depicting peak amplitudes, areas, and ratios relative to reference controls. Ratio of total areas of peaks.

(FIG. 6A), 4190x; (FIG. 6B), 16,250x.

(FIG. 7B), 8150x.

(FIG. 8A), 5270x; (FIG. 8B), 16,700x.

(FIG. 10B), 1000x, (FIG. 10A), 10,000x.

(FIG. 11A), 1000x, (FIG. 11B), 10,000x.

FIG. 15. SEM micrographs of transformed mouse fibroblast cells grown on p-GlcNAc membranes. Magnification.

FIG. 21A–G. Three-dimensional p-GlcNAc matrices produced in various solvents. Specifically, the p-GlcNAc matrices were produced in distilled water (FIG. 21A, FIG. 21D), 10% methanol in distilled water (FIG. 21B), 25% methanol in distilled water (FIG. 21C), 10% ethanol in distilled water (FIG. 21E), 25% ethanol in distilled water (FIG. 21F) and 40% ethanol in distilled water (FIG. 21G). Magnification: 200x. A scale marking of 200 microns is indicated on each of these figures.

FIG. 26A–26C depict rats which have had prototype 1 (fully acetylated p-GlcNAc) membrane abdominally implanted, as described, below, in Section 18.1. FIG. 26A shows a rat at day 0 of the implantation; FIG. 26B shows a rat at day 14 post-implantation; FIG. 26C shows a rat at day 21 post-implantation. FIG. 26D–26E depict rats which have had prototype 3A (lyophilized and partially deacetylated p-GlcNAc membrane) abdominally implanted, as described, below, in Section 18.1. FIG. 26D shows a rat at day 0 of the implantation; FIG. 26E shows a rat at day 14 post-implantation.

DETAILED DESCRIPTION OF THE INVENTION

Presented below, is, first, a description of physical characteristics of the purified p-GlcNAc species of the invention, of the p-GlcNAc derivatives, and of their reformulations. Next, methods are described for the purification of the p-GlcNAc species of the invention from microalgae, preferably diatom, starting sources. Third, derivatives and reformulations of the p-GlcNAc, and methods for the production of such derivatives and reformulations are presented. Finally, uses are presented for the p-GlcNAc, p-GlcNAc derivatives and/or p-GlcNAc reformulations of the invention.

5.1. p-GlcNAc

Figure 1:
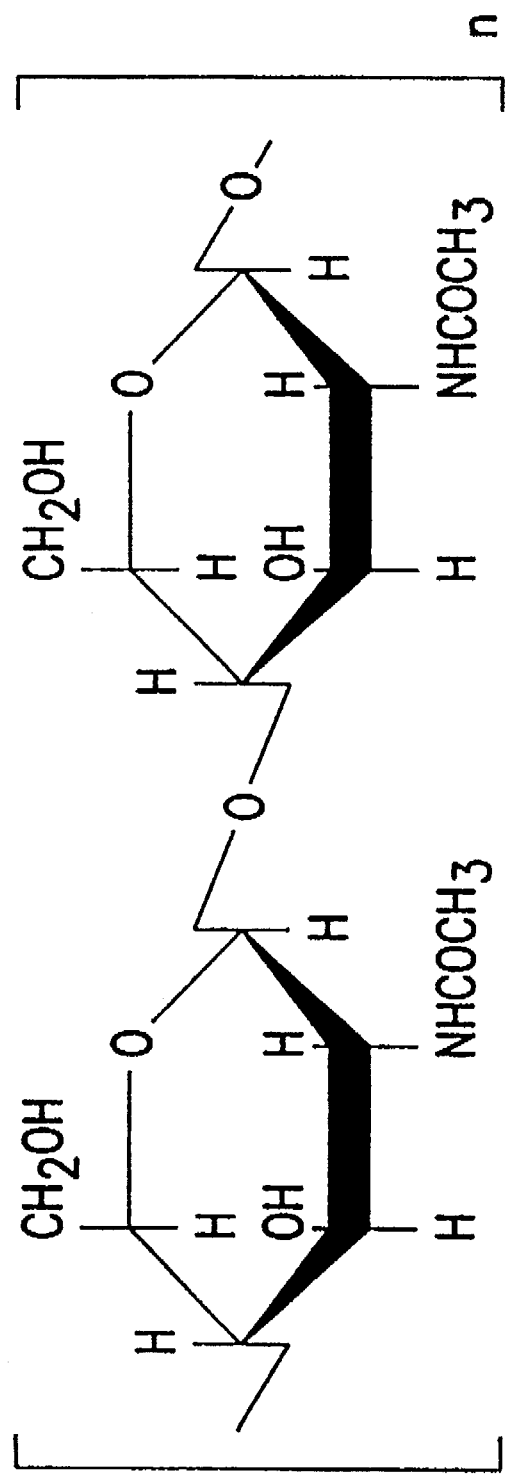
FIG. 1. Chemical structure of 100% p-GlcNAc. "n" refers to an integer ranging from about 4,000 to about 150,000, with about 4,000 to about 15,000 being preferred.

The p-GlcNAc polysaccharide species of the invention is a polymer of high molecular weight ranging from a weight average of about 800,000 daltons to about 30 million daltons, based upon gel permeation chromatography measurements. Such a molecular weight range represents a p-GlcNAc species having about 4,000 to about 150,000 N-acetylglucosamine monosaccharides attached in a β-1→4 configuration, with about 4,000 to about 15,000 N-acetylglucosamine monosaccharides being preferred (FIG. 1).

The variability of the p-GlcNAc of the invention is very low, and its purity is very high, both of which are evidenced by chemical and physical criteria. Among these are chemical composition and non-polysaccharide contaminants. First, chemical composition data for the p-GlcNAc produced using two different purification methods, both of which are described in Section 5.3, below, is shown in Table I below. As can be seen, the chemical composition of the p-GlcNAc produced by both methods is, within the bounds of experimental error, the same as the formula compositions of p-GlcNAc. Second, as is also shown in Table I, the p-GlcNAc produced is free of detectable protein contaminants, is substantially free of other organic contaminants such as free amino acids, and is substantially free of inorganic contaminants such as ash and metal ions (the p-GlcNAc of the invention may deviate up to about 2% from the theoretical values of carbon, hydrogen, nitrogen and oxygen for pure p-GlcNAc). Therefore, as used herein, the terms "substantially free of organic contaminants" and "substantially free of inorganic contaminants" refer to compositions of p-GlcNAc having the profiles for carbon, hydrogen, nitrogen and oxygen which deviate no more than about 2% from the theoretical values, and preferably, the p-GlcNAc of the invention contain a profile as exemplified in the Experimental Data on p-GlcNAc mats in Table I (allowing for the percent deviation). Further, the p-GlcNAc of the invention exhibits a very low percentage of bound water.

TABLE I

CHEMICAL ANALYSIS DATA (% by weight)
Theoretical Values for Pure p-GlcNAc:

| Carbon | 47.29 |
|---|---|
| Hydrogen | 6.40 |
| Nitrogen | 6.89 |
| Oxygen | 39.41 |
| Protein | 0.00 |

TABLE I-continued

Experimental Data on p-GlcNAc Mats:
(Number of experimental batches for each membrane type being greater than 30 for each membrane type)

| | MECHANICAL FORCE METHOD | | CHEMICAL/ BIOLOGICAL METHOD | |
|---|---|---|---|---|
| | Normalized [1] | % Dev. | Normalized [1] | % Dev. |
| Carbon | 47.21 ± 0.08 | −0.17 | 47.31 ± 0.11 | +0.04 |
| Hydrogen | 6.45 ± 0.08 | +0.78 | 6.34 ± 0.08 | −0.94 |
| Nitrogen | 6.97 ± 0.18 | +0.87 | 6.94 ± 0.16 | +0.73 |
| Oxygen | 39.55 ± 0.36 | +0.36 | 39.41 ± 0.10 | 0.00 |
| | Average Values | | Average Values | |
| Protein | 0.00 | | 0.00 | |
| Ash | 1.30 | | 0.98 | |
| Moisture | 2.0 | | 1.2 | |

[1] Raw analytical data have been normalized to account for ash and moisture content of the samples.

Figure 2:
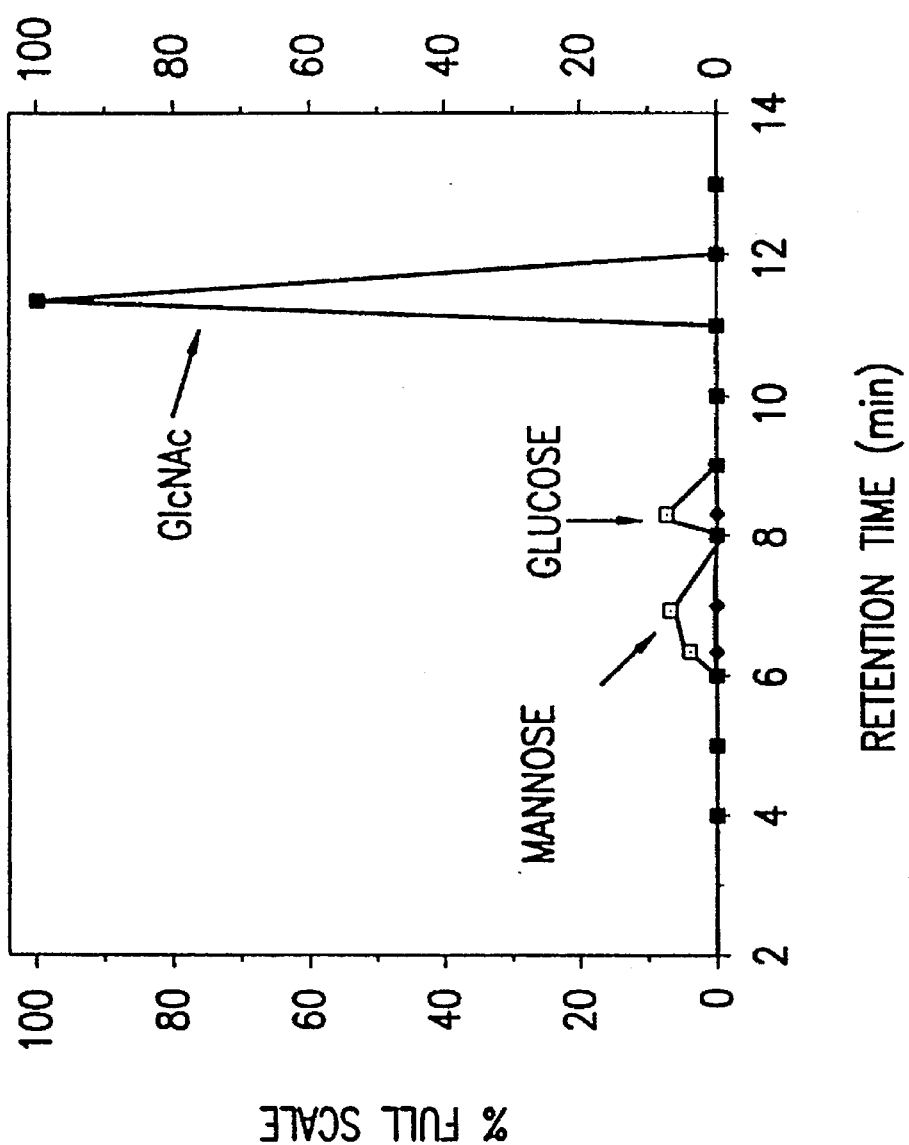
FIG. 2. Carbohydrate analysis of p-GlcNAc, Gas Chromatography-Mass Spectroscopy data. Solid squares represent p-GlcNAc purified using the acid treatment/ neutralization variation of the Chemical/Biological method, as described in Section 5.3.2, below.

The pure p-GlcNAc of the invention exhibits a carbohydrate analysis profile substantially similar to that shown in FIG. 2. The primary monosaccharide of the pure p-GlcNAc of the invention is N-acetylglucosamine. Further, the pure p-GlcNAc of the invention does not contain the monosaccharide glucosamine.

Figure 3A:
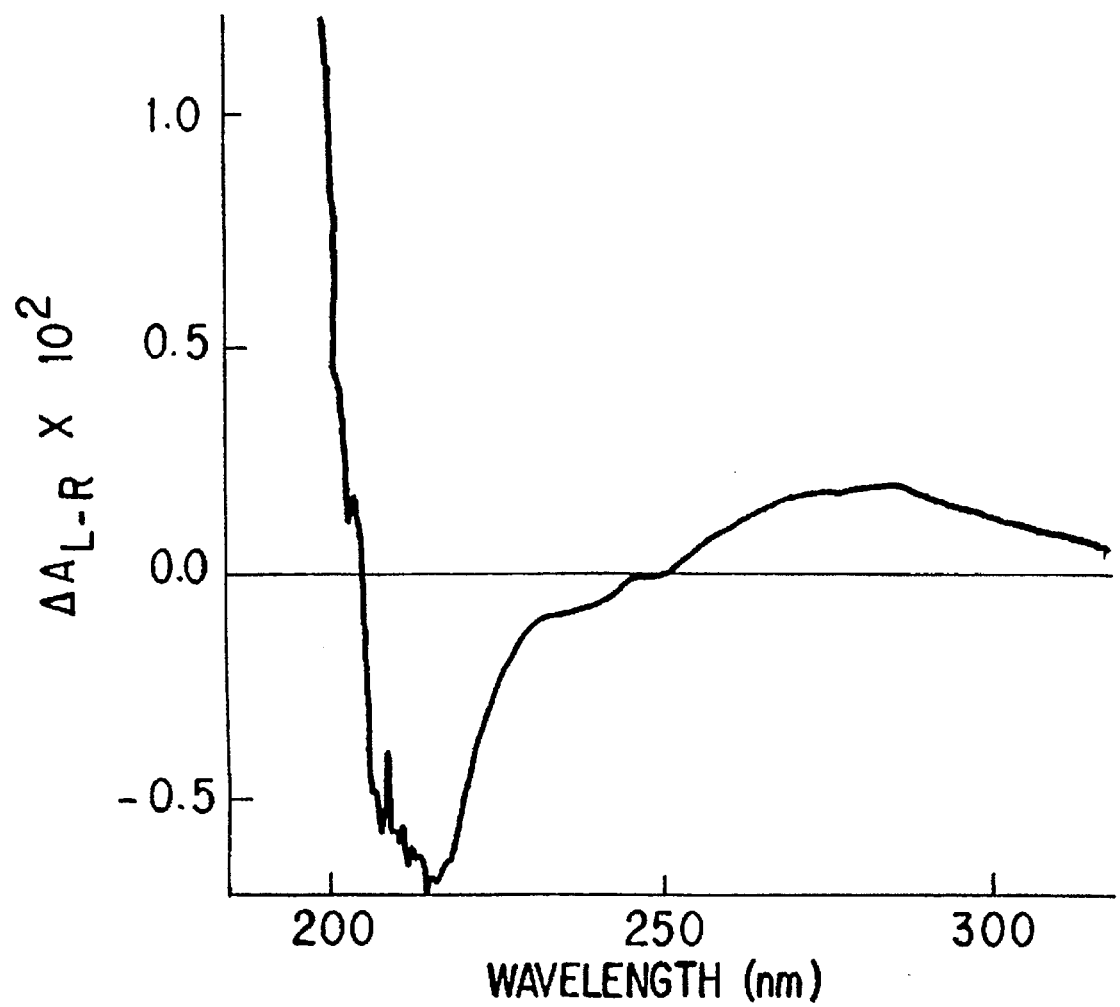
FIG. 3A. Circular dichroism spectra of solid membranes of pure p-GlcNAc.
Figure 4A:
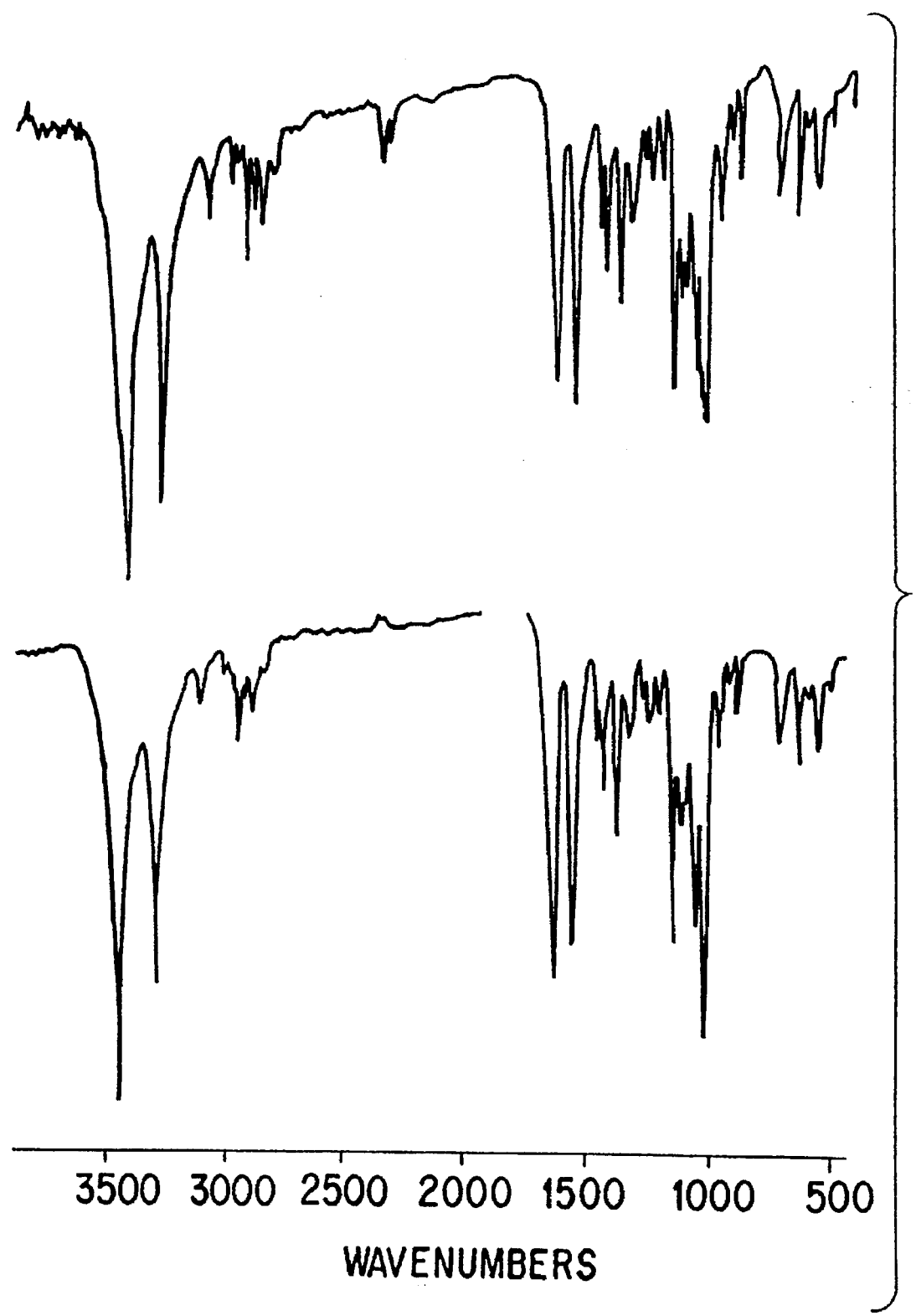
FIG. 4A. Infra-red spectra analyses of thin membranes of pure diatom p-GlcNAc prepared by the mechanical force purification method, top, and the chemical/biological purification method, bottom.
Figure 4B:
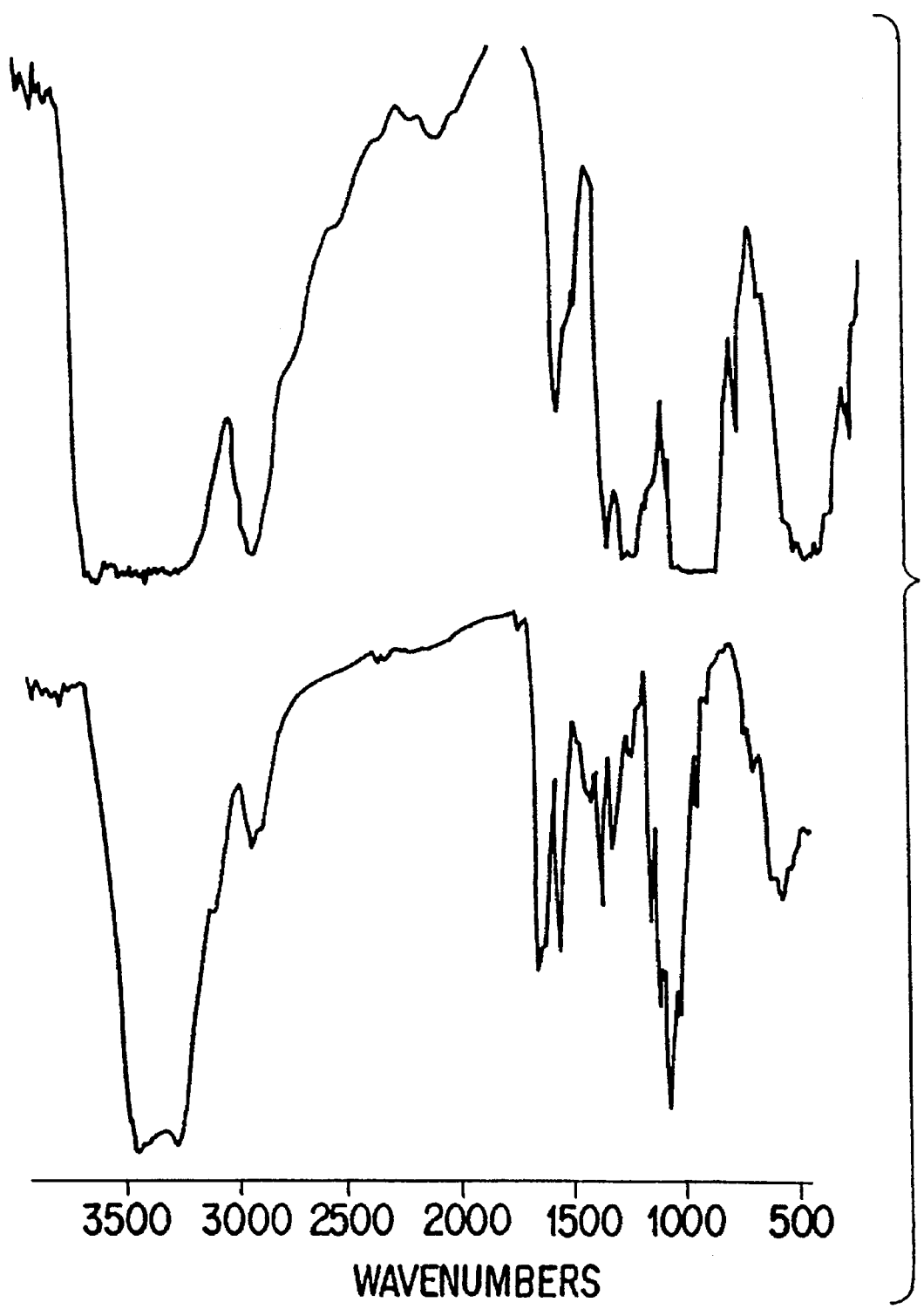
FIG. 4B. Infra-red spectra analyses of two preparations of commercial "chitin" cast into membranes according to the methods detailed in Section 5.5, below.
Figure 4C:
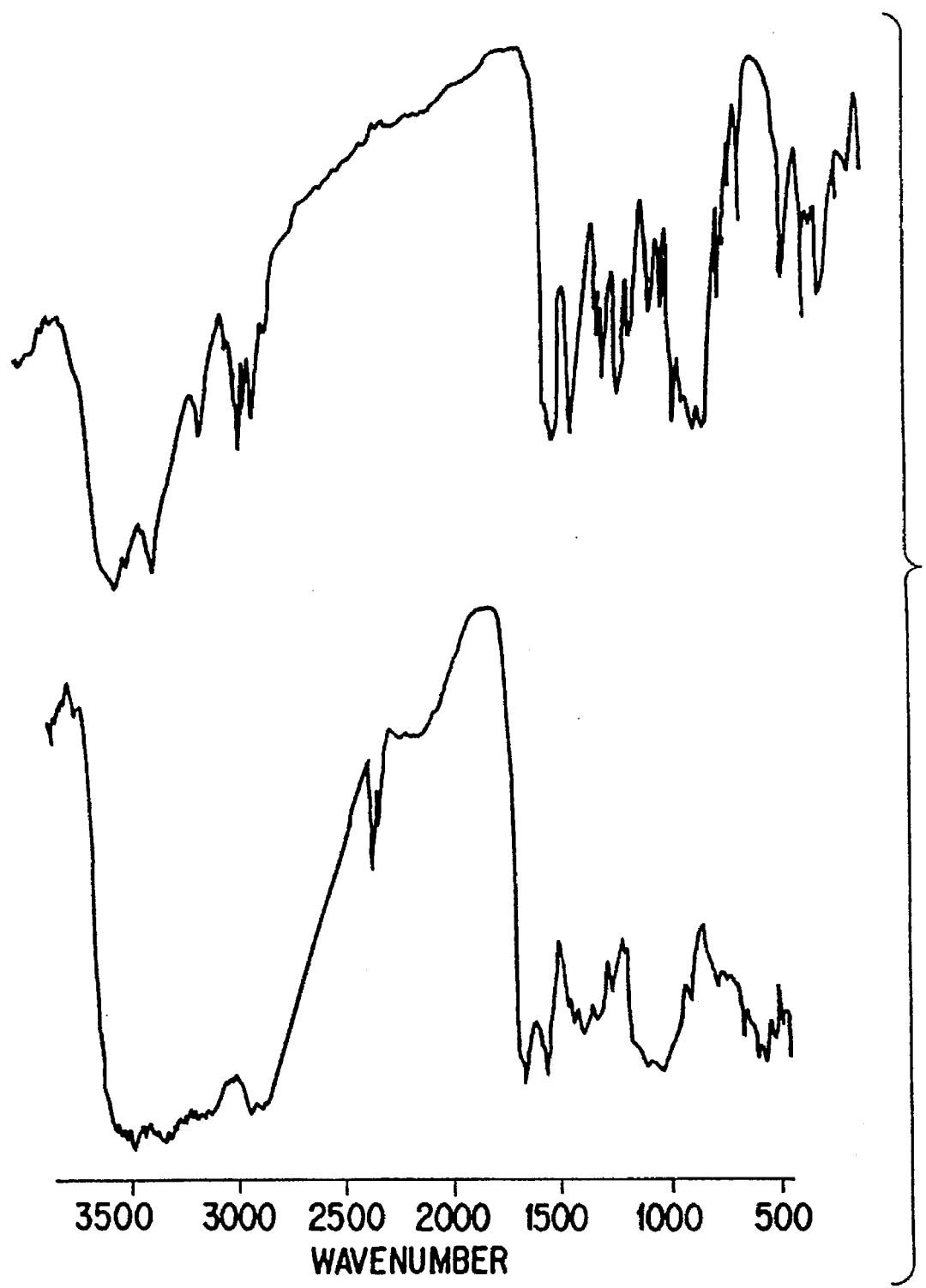
FIG. 4C. Infra-red spectra analyses of pure p-GlcNAc which was modified by heat denaturation (top) and by chemical deacetylation (bottom), according to the methods detailed in Section 5.4, below.
Figure 4D:
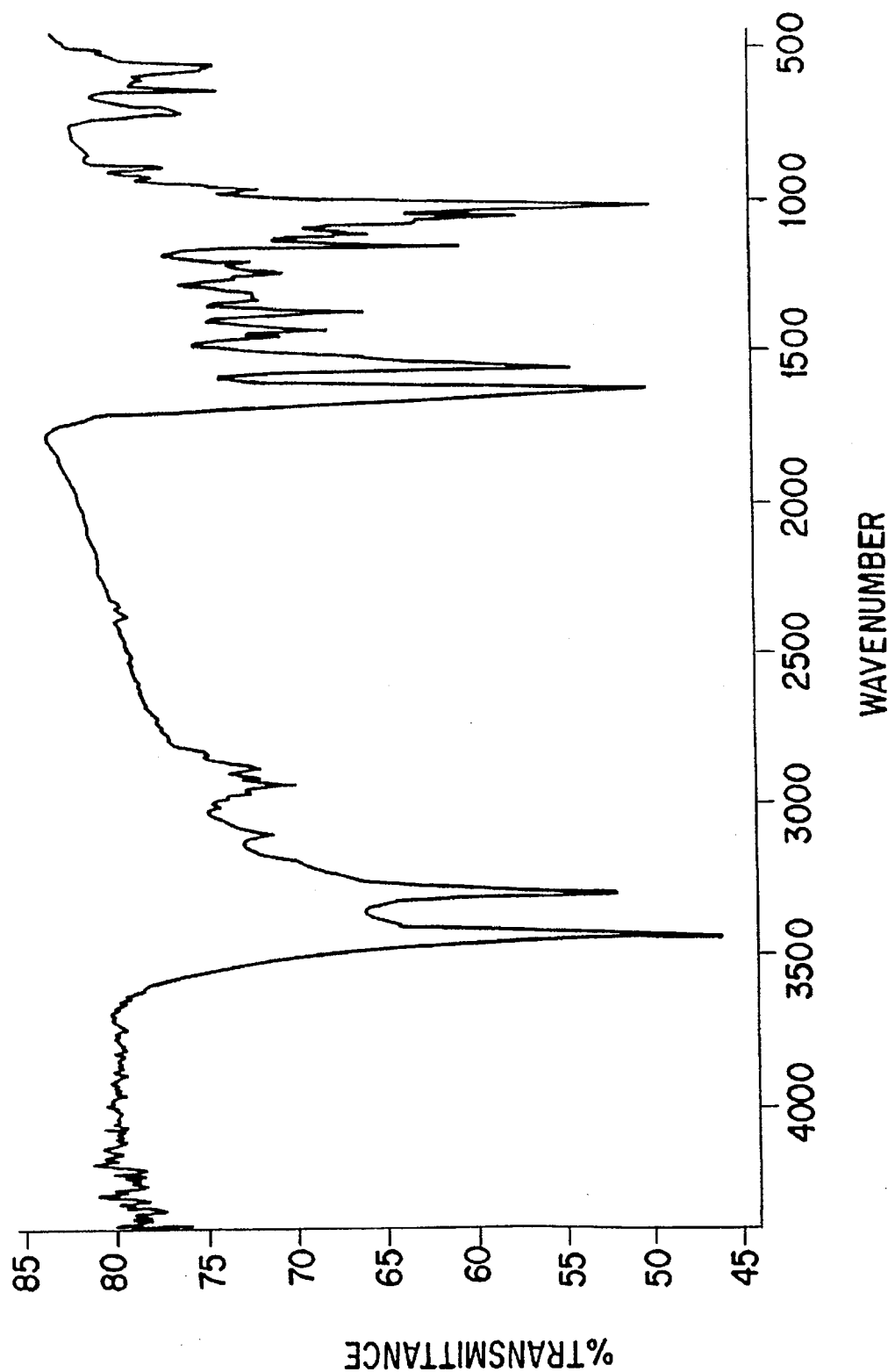
FIG. 4D. Infra-red spectrum analysis of a p-GlcNAc membrane derived from the diatom *Thalassiosira fluviatilis*, using the chemical/biological purification method, as detailed in Section 5.3.2, below.

The circular dichroism (CD) and sharp infra-red spectra (IR) of the p-GlcNAc of the invention are shown in FIGS. 3A, and FIGS. 4A and 4D, respectively, which present analyses of material produced using the methods described in Section 5.3, below. Such physical data corroborates that the p-GlcNAc of the invention is of high purity and crystallinity. The methods used to obtain the CD and IR data are described, below, in the Working Example in Section 6.

Figure 5B:
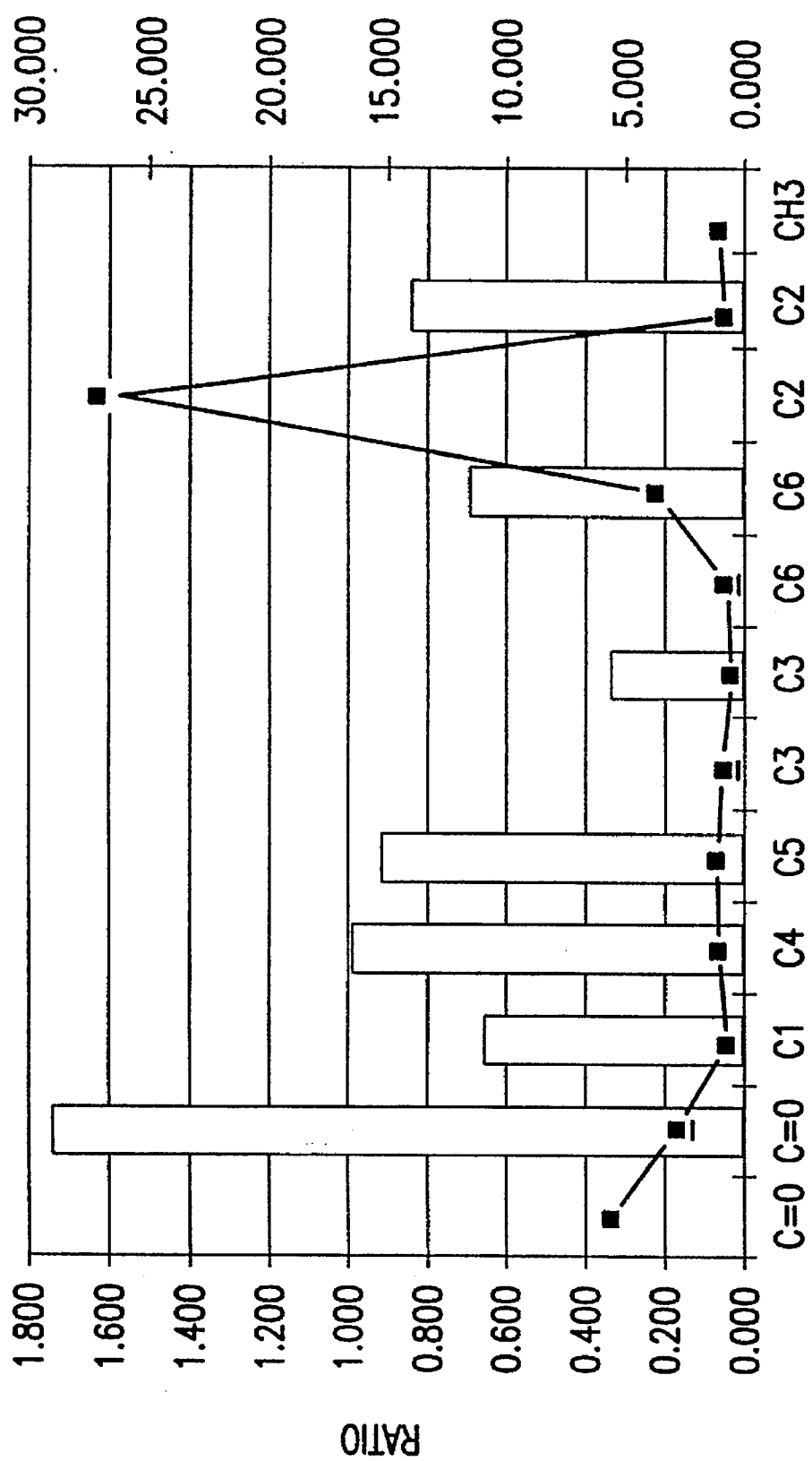
FIG. 5B. NMR analysis of p-GlcNAc purified using the chemical/biological purification method as described in Section 5.3.2. The graph depicts the ratios of total areas of peaks.
Figure 18:
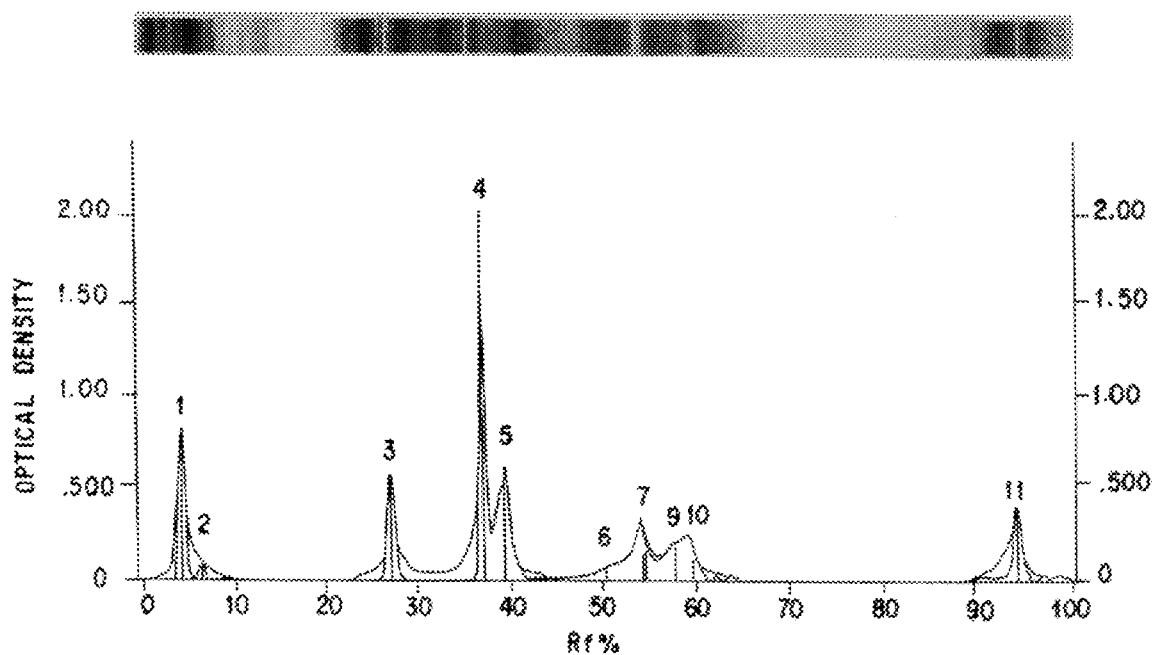
FIG. 18. Transformed NMR data curves, used to obtain areas for each carbon atom and to then calculate the CH3 (area) to C-atom(area) ratios.

NMR analysis of the pure p-GlcNAc of the invention exhibits a pattern substantially similar to that seen in FIGS. 5A, 5B, 18. Such an NMR pattern indicates not only data which is consistent with the p-GlcNAc of the invention being a fully acetylated polymer, but also demonstrates the lack of contaminating organic matter within the p-GlcNAc species.

The electron micrographic structure of the p-GlcNAc of the invention, as produced using the methods described in Section 5.3, below and demonstrated in the Working Examples presented, below, in Section 8 and 9, is depicted in FIGS. 6 through FIG. 9E.

The p-GlcNAc of the invention exhibits a high degree of biocompatability. Biocompatability may be determined by a variety of techniques, including, but not limited to such procedures as the elution test, intramuscular implantation, or intracutaneous or systemic injection into animal subjects. Briefly, an elution test (U.S. Pharmacopeia XXII, 1990, pp. 1415–1497; U.S. Pharmacopeia XXII, 1991, Supplement 5, pp. 2702–2703) is designed to evaluate the biocompatability of test article extracts, and assays the biological reactivity of a mammalian cell culture line which is sensitive to extractable cytotoxic articles (such as, for example, the L929 cell line) in response to the test article. The Working Example presented in Section 10, below, demonstrates the high biocompatability of the p-GlcNAc of the invention.

5.2. METHODS OF PRODUCING MICROALGAL SOURCES OF p-GtcNAc

5.2.1. MICROALGAL SOURCES OF p-GlcNAc

Figure 12A:
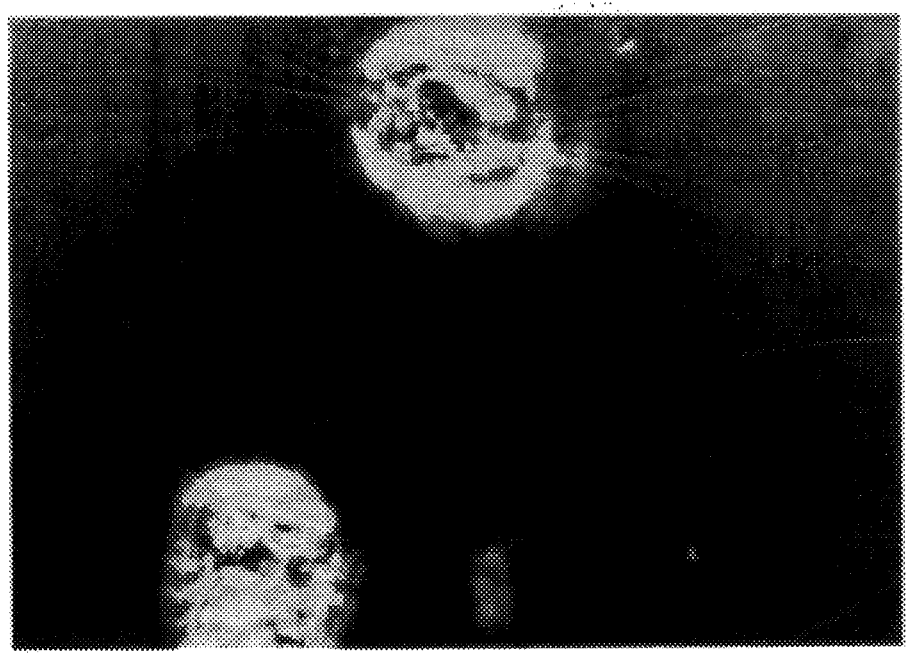
FIG. 12A–B. Photographs of diatoms. Note the p-GlcNAc fibers extending from the diatom cell bodies.
Figure 12B:
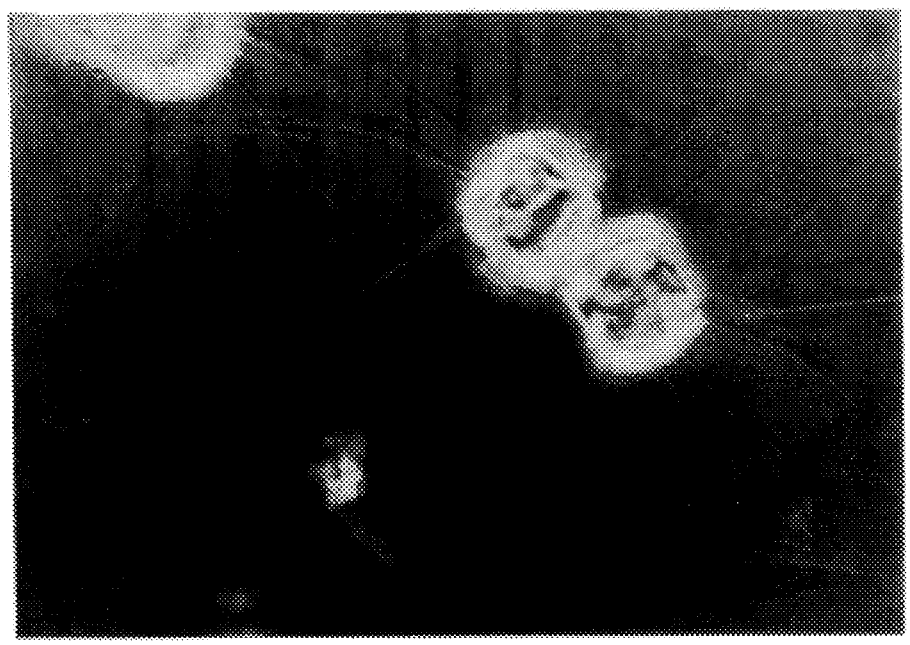

The p-GlcNAc of the invention is produced by, and may be purified from, microalgae, preferably diatoms. The diatoms of several genuses and numerous species within such genuses may be utilized as p-GlcNAc starting sources. Each of these diatoms produce p-GlcNAc. See FIG. 12A–B for photographs of such diatoms. The diatoms which may be used as starting sources for the production of the p-GlcNAc of the invention include, but are not limited to members of the *Coscinodiscus genus*, the *Cyclotella genus*, and the *Thalassiosira genus*, with the *Thalassiosira genus* being preferred. Among the *Coscinodiscus genus*, the species of diatom that may be used to produce the p-GlcNAc of the invention include, but are not limited to the *concinnus* and *radiatus* species. The diatoms among the *Cyclotella genus* which may be used include, but are not limited to the *caspia*, *cryptica*, and *meneghiniana species*. The Thalassiosira diatoms that may be utilized to produce the starting material for the p-GlcNAc of the invention include, but are not limited to the *nitzschoides, aestivalis, antarctica, deciphens, eccentrica, floridana, fluviatilis, gravida, guillardii, hyalina, minima, nordenskioldii, oceanica, polychorda, pseudonana; rotula, tubifera, tumida*, and *weissflogii species*, with the *fluviatilis* and *weissflogii species* being preferred. Diatoms such as those described above may be obtained, for example, from the culture collection of the Bigelow Laboratory for Ocean Sciences, Center for Collection of Marine Phytoplankton (McKown Point, West Boothbay Harbor, Me., 04575).

5.2.2. METHODS FOR GROWING DIATOMS

Any of the diatoms described in Section 5.2.1, above, may be grown by utilizing, for example, the methods described in this section. New diatom cultures are initiated by inoculating, under aseptic conditions, Nutrient Medium with an aliquot of a mature diatom culture. The Nutrient Medium must be free of all other microorganisms, therefore all materials, including water, organic components, and inorganic components used in the preparation of the Nutrient Medium must be sterile. In addition, it is mandatory that all procedures involved in this operation be conducted under strictly aseptic conditions, i.e., all containers, all transfers of substances from one vessel to another, etc. must be performed in a sterile environment. The quantity of Nutrient Medium to be prepared at one time should not exceed what is necessary to start a new culture. For example, Fernbach flasks which occupy approximately one square foot of surface may be used as vessels for the diatom cultures, and such vessels require one liter of Nutrient Medium for optimum growth of the diatom organism.

Preparation of the nutrient medium involves the following operations:
a) Acquisition and processing of seawater
b) Preparation of distilled and deionized water.
c) Preparation of primary nutrient stocks
d) Preparation of nutrient working stocks
e) Preparation of the final nutrient medium Filtered seawater may be obtained, for example, from the Marine Biology Laboratory (Woods Hole, Mass.). Seawater containers should be stored at 5° C. (+ or −2° C.). When required, the necessary volume of water may be filtered through a Buchner filtration unit, using a Supor-800 polyether sulfone filter membrane with 0.8 micron pore size (Gelman, Inc.). The seawater is then sterilized by autoclaving at, for example, 121° C. for at least about 15 minutes per liter. On completion of the sterilization process, the capped flasks are immediately cooled, preferably by transfer to a cold room capable of allowing the solutions to reach a temperature of approximately 5° C. (+ or −2° C.). When it is to be used, solutions are allowed to reach room temperature.

Tap water is distilled and deionized using standard equipment and procedures, and collected and stored in clean, securely capped, preferably glass, containers.

Listed below are formulas which may be followed in preparing the stock solutions necessary for the preparation of the Nutrient Medium. It is to be understood that while such formulas are to be used as guides, it is intended that routine variations of such formulas which contribute to the preparation of a Nutrient Medium capable of sustaining microalgal diatom growth sufficient for the p-GlcNAc preparative processes described here also be within the scope of the present invention.

I. Trace Metal Primary Stocks (TMPS)

a. 39 mM $CuSO_4 \cdot 5H_2O$ (copper [II] sulfate pentahydrate) (9.8g copper [II] sulfate/L)
b. 7.5 mM $ZnSO_4 \cdot 7H_2O$ (Zinc sulfate heptahydrate) (22 g zinc sulfate/L)
c. 42 mM $CoCl_2 \cdot 6H_2O$ (Cobalt [II] chloride hexahydrate) (10g cobalt [II] chloride/L)
d. 91 mM $MnCl_{12} \cdot 4H_2O$ (Manganese [II] chloride tetrahydrate) 18g manganese [II] chloride/L)
e. 26 mM $NaMoO_4 \cdot 2H_2O$ (Sodium molybdate dihydrate) 6.3 g sodium molybdate/L)
f. 1 mM $H_2SeO_3$ (Selenious acid) (0.129 g selenious acid/L).

Sterile filter each nutrient with a filter of no greater than 0.2 mm pore size.

II. Vitamin Primary Stocks (VPS)

a. 1 mg/ml Vitamin B12
b. 0.1 mg/ml Biotin

Sterile filter both stocks with a filter of no greater than 0.2 mm pore size.

III. Sodium Salts Working Stocks (SSWS)

a. Sodium nitrate working stock: 0.88M (75 g $NaNO_3$/L)
b. Sodium phosphate monobasic monohydrate working stock: 36.2 mM $NaH_2PO_4 \cdot H_2O$ (5 g $NaH_2PO_4 \cdot H_2O$/L)
c. Sodium metasilicate monohydrate working stock: 0.11M $Na_2SiO_3 \cdot 9H_2O$ (30 g $Na_2SiO_3 \cdot 9H_2O$/L) Sterile filter each of the SSWS with a filter of no greater than 0.2 mm pore size.

IV. Trace Metal Working Stocks (TMWS)

11.7 mM $Na_2EDTA$ (Ethylenediamine Tetraacetic acid, disodium salt dihydrate) (4.36 g/L)

11.7 mM $FeCl_3 \cdot 6H_2O$ (Iron [III] chloride hexahydrate) (3.15 g/L)

1 ml/L of each of the six primary trace metal stocks listed above.

Sterile filter with a filter of no greater than 0.2 mm pore size. Note that the trace metal working stock must be prepared fresh weekly.

Vitamin Working Stock (VWS)

1.0 µg/ml Biotin (1.0 ml primary Biotin Stock/100 ml)

1.0 µg/ml Vitamin B12 (0.1 ml Vitamin B12 primary stock/100 ml)

20 mg of Thiamine HCl (Thiamine hydrochloride/100 ml).

Sterile filter with a filter of no greater than 0.2 mm pore size. Note that a new Vitamin Working Stock should be prepared fresh weekly.

Described below are techniques which may be followed for the preparation of Nutrient Medium and for diatom culturing. It is to be understood that, in addition to these techniques, any routine variation in the formulas and/or procedures described herein which result in a Nutrient Medium and in procedures capable of sustaining diatom growth sufficient for the preparative processes described herein is intended to be within the scope of the present invention.

Nutrient Medium may be prepared, for example, as follows: To each liter of filtered and sterilized seawater may be added 1 ml of the $NaNO_3$ working stock, 1 ml of the $NaH_2PO_4$-$H_2O$ working stock, 1 ml of the Trace Metal working stock, and 1 ml of the $Na_2SiO_3 \cdot 9H_2O$ working stock. Simultaneously with the addition of $Na_2SiO_3 \cdot 9H_2O$, 2 mls of 1N HCl may be added and the solution may be shaken to mix. Next, 1.5 mls 1N NaOH may be added and the solution may again be shaken to mix. Finally, 0.5 ml of the Vitamin working stock may be added.

In order to grow a new diatom culture, 7 ml of a mature culture, (having a cell density within a range of about $1 \times 10^5$ to about $1 \times 10^6$ cells/ml.), may be transferred to a sterile container containing 100 ml of sterile Nutrient Medium, which may be prepared according to the methods described above. The inoculated culture may then be incubated for 8 days under the following conditions:

Temperature: 20 degrees Centigrade

Constant illumination.

Agitation: Gentle swirling of flasks once per day.

After 8 days of incubation, 80 ml of this incubated culture may be transferred, under sterile conditions, to 1000 ml of Nutrient Medium, which may, for example, be contained in a 2.8 L Fernbach flask, protected by a cotton wool plug covered by cheesecloth. Such a culture may be allowed to incubate and grow to the desired cell density, or alternatively, may be used to inoculate new diatom cultures. Once a culture reaches a desired cell density, the culture's p-GlcNAc fibers may be harvested, and the p-GlcNAc of the invention may be purified, using methods such as those described below in Section 5.3, below.

$CO_2$ may be dissolved in the culture solution in order to maintain a culture pH of approximately 7 to 8, with approximately 7.4 being preferred. The maintenance of such a neutral pH environment, greatly increases the p-GlcNAc yield that may be obtained from each diatom culture.

5.3. METHODS FOR ISOLATION, PURIFICATION, AND CONCENTRATION OF p-GlcNAc FIBERS

Presented in this Section are methods which may be utilized for the preparation of p-GlcNAc fibers from diatom cultures such as those described, above, in Section 5.2.

While each of the methods described below for the purification of p-GlcNAc from microalgae, preferably diatom, starting sources produces very pure, unadulterated, crystalline p-GlcNAc, each of the methods yields p-GlcNAc having specific characteristics and advantageous features. For example, the p-GlcNAc of the invention purified via the Mechanical Force method presented in Section 5.3.1, below, produces a p-GlcNAc membrane that provides a superior substrate for the attachment of cells to the p-GlcNAc. The second method, described below in Section 5.3.2, the Chemical/Biological method, produces a much higher average yield than the average p-GlcNAc yield produced by the Mechanical Force method. Additionally, the acid treatment/ neutralization variation described as part of the Chemical/ Biological method of Section 5.3.2, below, produces extremely long p-GlcNAc fibers, with some fibers being in excess of 100 µm, and containing molecules of the p-GlcNAc polymer of very high molecular weight, as high as 20–30 million daltons.

5.3.1. MECHANICAL FORCE METHOD FOR PREPARATION OF PURE p-GlcNAc

The p-GlcNAc fibers may be separated from diatom cell bodies by subjecting the contents of the culture to an appropriate mechanical force. Such a mechanical force may include, but is not limited to, a shear force generated by, for example, a colloid mill, an ultrasound device, or a bubble generator, or a cutting force generated by, for example, a Waring blender.

The resulting suspension of diatom cell bodies and p-GlcNAc fibers are then segregated. For example, the suspension may be subjected to a series of centrifugation steps which segregate the p-GlcNAc fibers from the cell bodies, yielding a clear supernatant exhibiting little, if any, visible flocculent material. A fixed angle rotor, and a temperature of about 10° C. are preferred for the centrifugation steps. The speed, duration, and total number of centrifugation steps required may vary depending on, for example, the specific centrifugation rotor being used, but the determination of the values for such parameters will be apparent to one of ordinary skill in the art.

The p-GlcNAc fibers in the supernatant may then be concentrated using techniques well known to those of skill in the art. Such techniques may include, but are not limited to suction and filtration devices.

Finally, the concentrated p-GlcNAc fibers are washed with, for example, distilled-deionized water, HCl and ethanol, or other appropriate solvents, preferably solvents, such as alcohols, in which both organic and inorganic materials dissolve.

The Working Example presented in Section 7, below, demonstrates the use of this method for the purification of p-GlcNAc.

5.3.2. CHEMICAL/BIOLOGICAL METHOD FOR PURIFICATION OF p-GlcNAc

In this method, p-GlcNAc fibers are separated from diatom cell bodies by subjecting them to chemical and/or biological agents as described in more detail below.

Diatom cultures may be treated with a chemical capable of weakening diatom cell walls, which leads to a release of the p-GlcNAc fibers without altering their structure. Such a chemical may include, but is not limited to, hydrofluoric acid (HF). Alternatively, a mature diatom culture may be treated with a biological agent capable of altering a biological process may be used to inhibit p-GlcNAc fiber synthesis, thus releasing the fibers already present. For example, such an agent may include, but is not limited to, polyoxin-D, an inhibitor of the enzyme N-acetylglucosaminyl-P-transferase.

The cell bodies and p-GlcNAc-containing fibers of diatom cultures treated with a member of the above described chemical or biological agents are then segregated. For example, the contents of treated diatom cultures may be allowed to settle such that the contents of the cultures are allowed to form two distinct layers. The upper layer will contain primarily the p-GlcNAc fibers, while the bottom layer will contain the cell bodies. The upper p-GlcNAc fiber-containing layer may be siphoned off, leaving behind the settled cellular material of the bottom layer.

The siphoned off p-GlcNAc fiber-containing layer may then be further purified to remove protein and other unwanted matter by treatment with a detergent that will not damage the p-GlcNAc fibers. Such a detergent may include, but is not limited to, sodium dodecyl sulfate (SDS).

When acid treatment, such as HF treatment, is used to separate p-GlcNAc fibers from diatom cell bodies, a step may be included for the dispersal of the fibers. Such a step may include, but is not limited to, the use of mechanical force for fiber dispersal, such as a step in which the fibers are subjected to the movements of an orbital shaker.

Alternatively, the acid-treated suspension may, in an optional step, be neutralized prior to further purification by detergent treatment. Such neutralization will, in general, change the pH of the suspension from approximately 1.8 to approximately 7.0, and may be accomplished by, for example, the addition of an appropriate volume of 1M Tris (pH 8.0) or the addition of an appropriate volume of sodium hydroxide (NaOH). Neutralization, in general, yields pure p-GlcNAc fibers of a substantially greater length than the other purification methods discussed herein.

The purified p-GlcNAc fibers may then be concentrated using techniques well known to those of skill in the art, such as by utilizing a suction and filtration device. Finally, the p-GlcNAc fibers are washed, in a series of steps with distilled-deionized water, HCl and ethanol, or other appropriate solvents, preferably solvents, such as alcohols, in which both organic and inorganic materials dissolve.

The Working Example presented, below, in Section 8 demonstrates the successful utilization of such a purification method.

5.4. DERIVATIZATION OF p-GlcNAc

Figure 13:
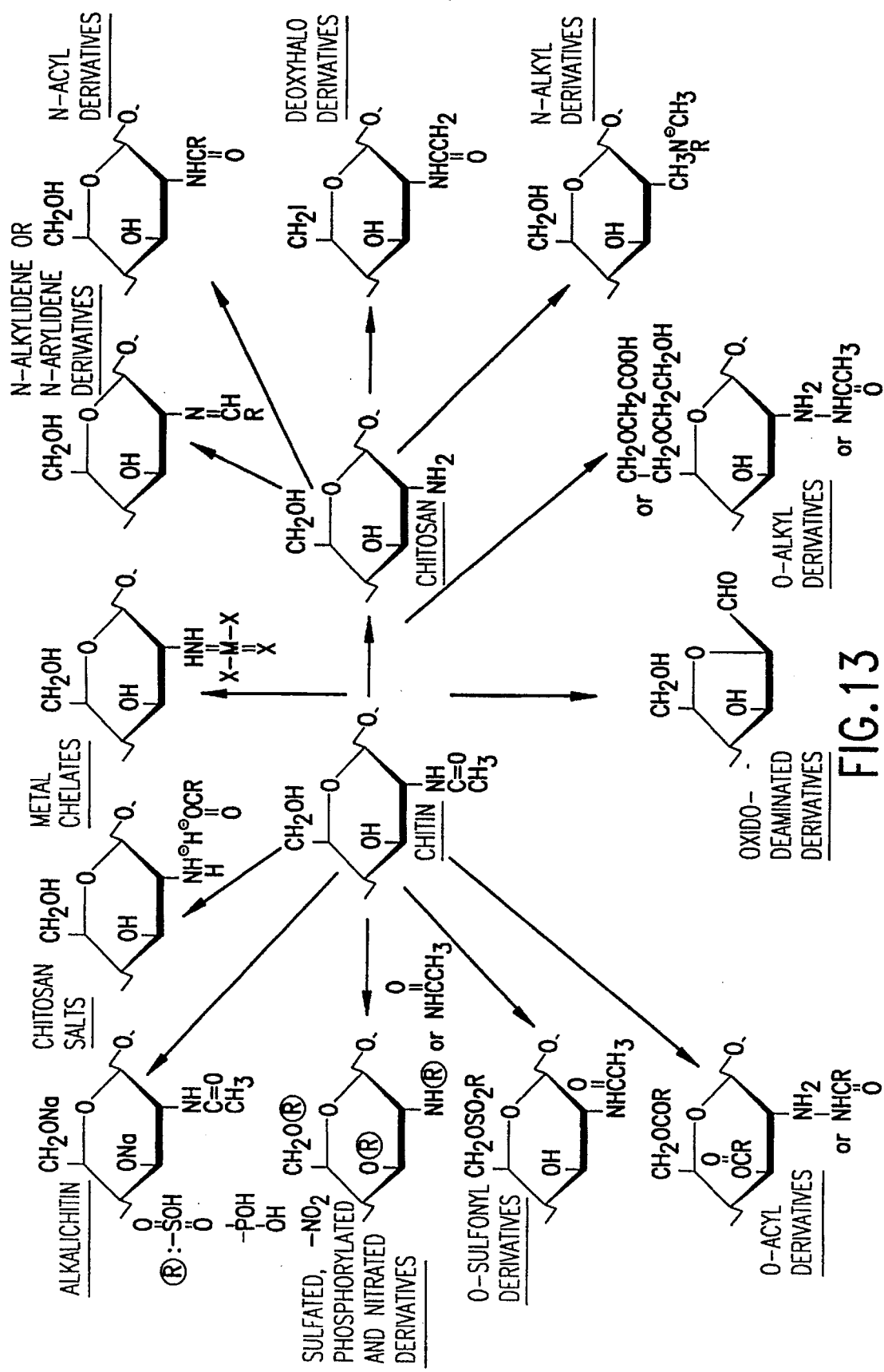
FIG. 13. Diagram depicting some of the possible p-GlcNAc and deacetylated p-GlcNAc derivatives of the invention. (Adapted from S. Hirano, "Production and Application of Chitin and Chitosan in Japan", in "Chitin and Chitosan", 1989, Skjak-Braek, Anthonsen, and Sanford, eds. Elsevier Science Publishing Co., pp. 37–43.)

The pure, fully acetylated p-GlcNAc of the invention may be derivatized, by utilizing a variety of controlled conditions and procedures, into a large range of different compounds. See FIG. 13 for a diagram depicting some of these compounds. Such derivatized compounds may include, but are not limited to, partially or completely deacetylated p-GlcNAc, which has been modified via chemical and/or enzymatic means, as described in further detail, below. Additionally, p-GlcNAc, or its deacetylated derivative, may be derivatized by being sulfated, phosphorylated, and/or nitrated. Further, as detailed below, O-sulfonyl, N-acyl, O-alkyl, N-alkyl, deoxyhalogen, and N-alkylidene and N-arylidene and other derivatives may be prepared from the p-GlcNAc or deacetylated p-GlcNAc of the invention. The deacetylated p-GlcNAc of the invention may also be used to prepare a variety of organic salts and/or metal chelates. Further, the p-GlcNAc, or a derivative thereof, of the invention may have attached to it, either covalently or non-covalently, any of a variety of molecules. Still further, the p-GlcNAc of the invention, or a derivative thereof, may be subjected to controlled hydrolysis conditions which yield groups of molecules having uniform and discrete molecular weight characteristics.

One or more of the monosaccharide units of the p-GlcNAc of the invention may be deacetylated to form a poly-β-1→4-N-glucosamine species. A poly-β-1→4-N-glucosamine species of the invention in which each of the monosaccharide units of the poly-β-1→4-N-acetylglucosamine species of the invention has been deacetylated will have a molecular weight of about 640,000 daltons to about 24 million daltons, with about 640,000 daltons to about 2.4 million daltons being preferred. A species with such a molecular weight range represents a species having about 4000 to about 150,000 glucosamine monosaccharides covalently attached in a β-1→4 configuration, with about 4,000 to about 15,000 glucosamine monosaccharides being preferred. At least one of the monosaccharide units of the poly-β-1→4-N-glucosamine species may remain acetylated, with about 25% to about 75% acetylation being preferred, and about 30% acetylation being most preferred.

The p-GlcNAc of the invention may be deacetylated by treatment with a base to yield glucosamines with free amino groups. This hydrolysis process may be carried out with solutions of concentrated sodium hydroxide or potassium hydroxide at elevated temperatures. To precisely control the extent of deacetylation and to avoid degradation of the main carbohydrate chain of the polysaccharide molecule, however, it is preferable that an enzymatic procedure utilizing a chitin deacetylase enzyme be used for p-GlcNAc deacylation. Such a deacetylase enzymatic procedure is well known to those of skill in the art and may be performed as in (U.S. Pat. No. 5,219,749), which is incorporated herein, by reference, in its entirety.

One or more of the monosaccharide units of the p-GlcNAc of the invention may be derivatized to contain at least one sulfate group, or, alternatively, may be phosphorylated or nitrated, as depicted below:

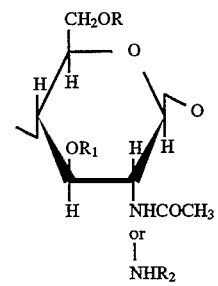

where, R and/or $R_1$, in place of a hydrogen, and/or $R_2$, in place of —$COCH_3$, may be a sulfate (—$SHO_3$), a phosphate (—$P(OH)_2$), or a nitrate (—$NO_2$) group.

Described below are methods by which such p-GlcNAc derivatives may be prepared. Before performing methods such as those described in this Section, it may be advantageous to first lyophilize, freeze in liquid nitrogen, and pulverize the p-GlcNAc starting material.

Sulphated p-GlcNAc derivatives may be generated, by, for example, a two step process. In the first step, O-carboxymethyl p-GlcNAc may be prepared from the p-GlcNAc and/or p-GlcNAc derivatives of the invention by, for example, utilizing techniques such as those described by Tokura et al. (Tokura, S. et al., 1983, Polym. J. 15:485). Second, the sulfation step may be carried out with, for example, N, N-dimethyl-formamide-sulfur trioxide, according to techniques well known to those of skill in the art, such as are described by Schweiger (Schweiger, R. G., 1972, Carbohydrate Res. 21:219). The resulting product may be isolated as a sodium salt.

Phosphorylated p-GlcNAc derivatives of the invention may be prepared, for example, by utilizing techniques well known to those of skill in the art, such as those described by Nishi et al. (Nishi, N. et al., 1986, in "Chitin in Nature and Technology, Muzzarelli et al., eds. Plenum Press, New York, pp. 297–299). Briefly, p-GlcNAc/methanesulfonic acid mixture may be treated with phosphorus pentoxide (in an approximately 0.5 to 4.0 molar equivalent) with stirring, at a temperature of about 0° C. to about 5° C. Treatment may be for about 2 hours. The resulting product may then be precipitated and washed using standard techniques well known to those of skill in the art. For example, the sample may be precipitated with a solvent such as ether, centrifuged, washed with a solvent such as ether, acetone, or methanol, and dried.

Nitrated p-GlcNAc derivatives may be prepared by utilizing techniques well known to those of skill in the art, such as those described by Schorigin and Halt (Schorigin, R. and Halt, E., 1934, Chem. Ber. 67:1712). Briefly, p-GlcNAc and/or a p-GlcNAc derivative may be treated with concentrated nitric acid to form a stable nitrated product.

One or more of the monosaccharide units of the p-GlcNAc of the invention may contain a sulfonyl group, as depicted below:

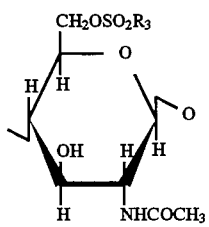

where $R_3$ may be an alkyl, an aryl, an alkenyl, or an alkynyl moiety. Such a derivative may be generated by well known methods such as the method described in Kurita et al. (Kurita, K. et al., 1990, Polym. Prep [Am. Chem. Soc., Div. Polym. Chem.] 31:624–625). Briefly, an aqueous alkali p-GlcNAc solution may be reacted with a chloroform solution of tosyl chloride, and the reaction may then be allowed to proceed smoothly at low temperatures.

One or more of the monosaccharides of the p-GlcNAc of the invention or its deacetylated derivative may contain one or more O-acyl groups, as depicted below:

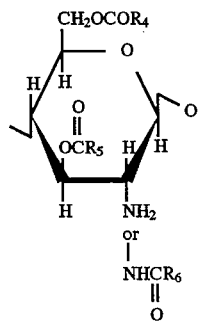

where $R_4$ and/or $R_5$, in place of hydrogen, may be an alkyl, an alkenyl, or an alkynyl moiety, and $R_6$ may be an alkyl, an alkenyl, or an alkynyl moiety. An example of such a derivative may be generated by well known methods such as those described by Komai (Komai, T. et al., 1986, in "Chitin in Nature and Technology", Muzzarelli et al., eds., Plenum Press, New York, pp. 497–506). Briefly, p-GlcNAc may be reacted with any of a number of suitable acyl chlorides in methanesulfonic acid to yield p-GlcNAc derivatives which include, but are not limited to, caproyl, capryl, lanoyl, or benzoyl derivatives.

One or more of the monosaccharides of the deacetylated p-GlcNAc of the invention may contain an N-acyl group, as depicted below:

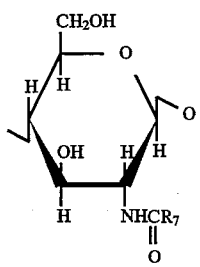

where $R_7$ may be an alkyl, an alkenyl, or an alkynyl moiety. Such a derivatization may be obtained by utilizing techniques well known to those of skill in the art, such as the technique described in Hirano et al. (Hirano, S. et al., 1976, Carbohydrate Research 47:315–320).

Deacetylated p-GlcNAc is soluble in a number of aqueous solutions of organic acids. The addition of selected carboxylic anhydrides to such p-GlcNAc-containing solutions, in aqueous methanolic acetic acid, results in the formation of N-acyl p-GlcNAc derivatives.

One or more of the monosaccharides of the deacetylated p-GlcNAc of the invention or of its deacetylated derivative, may contain an O-alkyl group, as depicted below:

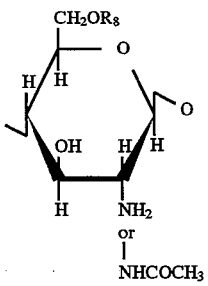

where $R_8$ may be an alkyl, and alkenyl, or a alkynyl moiety. Such a derivatization may be obtained by using techniques well known to those of skill in the art. For example, the procedure described by Maresh et al. (Maresh, G. et al., in "Chitin and Chitosan," Skjak-Braek, G. et al., eds., 1989, Elsevier Publishing Co., pp. 389–395). Briefly, deacetylated p-GlcNAc may be dispersed in dimethoxyethane (DME) and reacted with an excess of propylene oxide. The period of the reaction may be 24 hours, and the reaction takes place in an autoclave at 40° to 90° C. The mixture may then be diluted with water and filtered. The DME may be removed by distillation. Finally, the end-product may be isolated via lyophilization.

One or more of the monosaccharide units of the p-GlcNAc of the invention may be an alkali derivative, as depicted below:

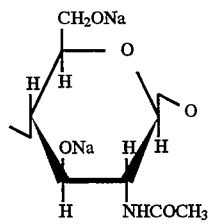

Such a derivative may be obtained by using techniques well known to those of skill in the art. For example, a method such as that described by Noguchi et al. (Noguchi, J. et al., 1969, Kogyo Kagaku Zasshi 72:796–799) may be utilized.

Briefly, p-GlcNAc may be steeped, under vacuo, in NaOH (43%, preferably) for a period of approximately two hours at about 0° C. Excess NaOH may then be removed by, for example, centrifugation in a basket centrifuge and by mechanical pressing.

One or more of the monosaccharide units of the deacetylated derivative of the p-GlcNAc of the invention may contain an N-alkyl group, as depicted below:

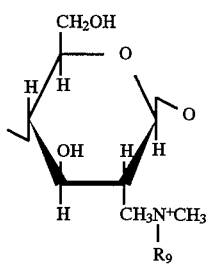

where $R_9$ may be an alkyl, an alkenyl, or an alkynyl moiety. Such a derivatization may be obtained by utilizing, for example, a procedure such as that of Maresh et al. (Maresh, G. et al., in "Chitin and Chitosan," Skjak-Brack, G. et al., eds. 1989, Elsevier Publishing Co., pp. 389–395), as described, above, for the production of O-alkyl p-GlcNAc derivatives.

One or more of the monosaccharide units of the deacetylated derivative of the p-GlcNAc of the invention may contain at least one deoxyhalogen derivative, as depicted below:

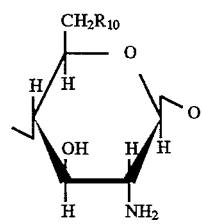

where $R_{10}$ may be F, Cl, Br, or I, with I being preferred. Such a derivative may be obtained by using techniques well known to those of skill in the art. For example, a procedure such as that described by Kurita et al. (Kurita, K. et al., 1990, Polym. Prep. [Am. Chem. Soc. Div. Polym. Chem.] 31:624–625) may be utilized. Briefly, a tosylated p-GlcNAc is made to react with a sodium halide in dimethylsulfoxide, yielding a deoxyhalogen derivative. p-GlcNAc tosylation may be performed by reacting an aqueous alkali p-GlcNAc solution with a chloroform solution of tosyl chloride. Such a reaction may proceed smoothly at low temperatures.

One or more of the monosaccharide units of the deacetylated derivative of the p-GlcNAc of the invention may form a salt, as depicted below:

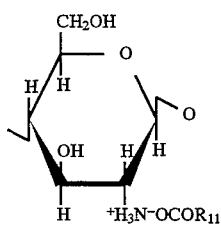

where $R_{11}$ may be an alkyl, an alkenyl, or an alkynyl moiety. Such a derivatization may be obtained by using techniques well known to those of skill in the art. For example, a procedure such as that described by Austin and Sennett (Austin, P. R. and Sennett, S., in "Chitin in Nature and Technology," 1986, Muzzarelli, R. A. A. et al., eds. Plenum Press, pp. 279–286) may be utilized. Briefly, deacetylated p-GlcNAc may be suspended in an organic medium such as, for example, ethyl acetate or isopropanol, to which may be added an appropriate organic acid such as, for example, formic, acetic, glycolic, or lactic acid. The mixture may be allowed to stand for a period of time (1 to 3 hours, for example). The temperature of reaction and drying may vary from about 12° to about 35° C., with 20° to 25° C. being preferred. The salts may then be separated by filtration, washed with fresh medium, and the residual medium evaporated.

One or more of the monosaccharide units of the deacetylated derivative of the p-GlcNAc of the invention may form a metal chelate, as depicted below:

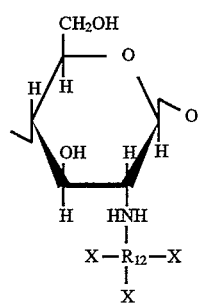

where $R_{12}$ may be a metal ion, particularly one of the transition metals, and X is the dative bond established by the nitrogen electrons present in the amino and substituted amino groups present in the deacetylated p-GlcNAc.

One or more of the monosaccharide units of the deacetylated derivative of the p-GlcNAc of the invention may contain an N-alkylidene or an N-arylidene group, as depicted below:

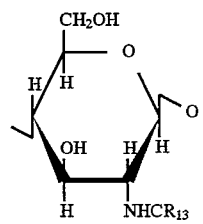

where $R_{13}$ may be an alkyl, an alkenyl, an alkynyl, or an aryl moiety. Such a derivatization may be obtained by using techniques well known to those of skill in the art. For example, a procedure such as that described by Hirano et al. (Hirano, S. et al., 1981, J. Biomed. Mat. Res. 15:903–911) may be utilized. Briefly, an N-substitution reaction of deacetylated p-GlcNAc may be performed with carboxylic anhydrides and/or arylaldehydes to yield acyl- and/or arylidene derivatives.

Further, the p-GlcNAc of the invention, or its deacetylated derivative, may be subjected to controlled hydrolysis conditions, which yield groups of molecules having uniform, discrete molecular weight and other physical characteristics. Such hydrolysis conditions may include, for example, treatment with the enzyme, lysozyme. p-GlcNAc may be exposed to lysozyme for varying periods of time, in order to control the extent of hydrolysis. In addition, the rate of hydrolysis may be controlled as a function of the extent to which the p-GlcNAc that is being lysozyme treated has been deacetylated. Deacetylation conditions may be as described earlier in this Section. The more fully a p-GlcNAc molecule has been deacetylated, between about 20 and about 90 percent deacetylated, the more fully the molecule will be hydrolyzed in a given time. Changes in physical characteristics, in addition to the lowering of molecular weight, may be elicited by hydrolysis and/or deacetylation treatments. Extensive hydrolysis causes liquefication of the p-GlcNAc. The results of a hydrolysis/deacetylation procedure are presented below in the Working Example of Section 9, below.

Further, heat denaturation may function to modify the crystalline structure of the p-GlcNAc. Such a modification of the p-GlcNAc product crystalline structure may advantageously affect, for example, the reactivity of the p-GlcNAc.

Further, a variety of molecules may be covalently or non-covalently functionally attached to the deacetylated derivatives of the p-GlcNAc of the invention. Such molecules may include, but are not limited to such polypeptides as growth factors, such as nerve growth factor, proteases, such as pepsin, hormones, or peptide recognition sequences such as RGD sequences, fibronectin recognition sequences, laminin, integrins, cell adhesion molecules, and the like. See, e.g., the compounds discussed, below, in Section 5.6.1.1. Covalent attachment of molecules to the exposed primary amines of deacetylated p-GlcNAc may be accomplished by, for example, chemical attachment utilizing bi-functional cross-linking reagents that act as specific length chemical spacers. Such techniques are well known to those of skill in the art, and may resemble, for example, the methods of Davis and Preston (Davis, M. and Preston, J. F. 1981, Anal. Biochem. 116:404–407) and Staros et al. (Staros, J. V. et al., 1986, Anal. Biochem. 156:220–222). Briefly, carboxylic residues on the peptide to be attached to the deacetylated or partially deacetylated p-GlcNAc of the invention may be activated and then crosslinked to the p-GlcNAc. Activation may be accomplished, for example, by the addition of a solution such as carbodiimide EDC (1-ethyl-3-(3-dimethylaminopropyl)carbodiimide) to a peptide solution in a phosphate buffer. Preferably, this solution would additionally contain a reagent such as sulpho-NHS (N-hydroxysulphosuccinimide) to enhance coupling. The activated peptide may be crosslinked to the deacetylated p-GlcNAc by mixing in a high pH buffer, such as carbonate buffer (pH 9.0–9.2).

The biological activity of the attached peptide (or any covalently attached molecule) can be maintained by varying the length of the linker molecule (e.g., the bi-functional crosslinking compound) utilized to attach the molecule to the p-GlcNAc of the invention. An appropriate linker length for a given molecule to be attached which will not alter the biological activity of the attached molecule can routinely be ascertained. For example, the biological, activity (e.g., a therapeutically effective level of biological activity) of a molecule which has been attached via a linker of a given length can be tested by utilizing well-known assays specific for the given molecule being attached.

Additionally, in order to maintain the biological activity of the molecule being attached, it may be necessary to utilize a linker which can be cleaved by an appropriate naturally occurring enzyme to release the peptide (or any covalently attached molecule).

As above, assays commonly employed by those of skill in the art may be used to test for the retention of the biological activity of the particular molecule being attached to ensure that an acceptable level of activity (e.g., a therapeutically effective level activity) is retained.

Alternatively, molecules such as those described above may be non-covalently attached to p-GlcNAc and its derivatives using techniques well known to those of skill in the art. For example, a molecule or molecules of choice may be mixed with suspensions of p-GlcNAc, with deacetylated or partially deacetylated p-GlcNAc solution, with a p-GlcNAc-lactate solution, with a deacetylated or partially deacetylated p-GtcNAc salt solution, or with any p-GlcNAc derivative solution. The mixtures can then be lyophilized. Molecules become bound to the p-GlcNAc matrices following lyophilization, presumably via hydrophobic, electrostatic and other non-covalent interactions. Such p-GlcNAc formulations are, therefore, very easy to produce. Further, such formulations can effectively be achieved with a wide variety of molecules having a broad spectrum of physical characteristics and water solubility properties, ranging from the most hydrophobic to the most hydrophilic. Upon attachment of the molecule or molecules, assays commonly employed by those of skill in the art to test the activity of the particular non-covalently attached molecule or molecules can be used to ensure that an acceptable level of activity (e.g., a therapeutically effective activity) is achieved with the attached molecule.

Encapsulation using the p-GlcNAc of the invention may be achieved using methods known in the art. For example, one method for achieving the p-GlcNAc encapsulation can involve the procedure outlined by Hwang et al. (Hwang, C. et al. in Muzzarelli, R. et al., eds., 1985, "Chitin in Nature and Technology", Plenum Press, pp. 389–396) which is incorporated by reference in its entirety.

Encapsulation can also be achieved, for example, by following a modification of the acid treatment/neutralization variation of the chemical/biological purification method presented, above, in Section 5.3.2. Rather than raising the pH of the p-GlcNAc solution to approximately neutral pH range (i.e., approximately 7.4), one may create a basic pH environment, by raising the pH to approximately 9.0 after the purification of the p-GlcNAc is completed. At a more basic pH, the structure of the p-GlcNAc of the invention, or a derivative thereof, assumes a more three-dimensional or "open" configuration. As the pH is lowered, the molecule's configuration reverts to a more compact, "closed" configuration. Thus, a compound or drug of interest may be added to a p-GlcNAc at a high pH, then the pH of the p-GlcNAc/drug suspension may be lowered, thereby "trapping" or encapsulating the drug of interest within a p-GlcNAc matrix.

Alternatively, hybrids comprising p-GlcNAc and/or p-GlcNAc derivatives may be formed. Such hybrids may contain any of a number of natural and/or synthetic materials, in addition to p-GlcNAc and/or p-GlcNAc derivatives. For example, hybrids may be formed of p-GlcNAc and/or p-GlcNAc derivatives plus one or more extracellular matrix (ECM) components. Such ECM components may include, but are not limited to, collagen, fibronectin, glycosaminoglycans, and/or peptidoglycans. Hybrids may also be formed of p-GlcNAc and/or p-GlcNAc derivatives plus one or more synthetic materials such as, for example, polyethylene. Such a p-GlcNac/polyethylene or p-GlcNac derivative/polyethylene hybrid may be made by thermally linking the hybrid components via, for example, autoclaving.

In the case of a collagen/p-GlcNAc hybrid, briefly, a p-GlcNAc suspension and a collagen suspension may be mixed and lyophilized, and crosslinked, preferably dehydrothermally crosslinked. The collagen species of such hybrids may be native or synthetic, and may be of human or non-human, such as bovine, for example, origin. p-GlcNAc/ collagen and/or p-GlcNAc derivative/collagen hybrid materials exhibit uniform properties, and form a porous matrix that may act, for example, as an efficient three-dimensional matrix for the attachment and growth of cells. The Working Example presented in Section 13, below demonstrates the formation, properties and usefulness of such a p-GlcNAc/ collagen hybrid.

Additionally, an iodo-p-GlcNAc derivative may be copolymerized with, for example, styrene, for the manufacture of novel plastic materials. Iodo-p-GlcNAc can be prepared by a process similar to that described by Kurita and Inoue (Kurita, K. and Inoue, S., 1989, in "Chitin and Chitosan", Skjak-Braek et al., eds., Elsevier Science Publishing Co., Inc., p. 365), via tosylation and iodination of p-GlcNAc. The iodo derivative of p-GlcNAc can then be dispersed in nitrobenzene and reacted with styrene, with tin (IV) chloride being used as a catalyst.

Hybrids comprising combinations of deacetylated p-GlcNAc and such compounds as, for example, heparin, sodium alginate, and carboxymethyl p-GlcNAc may be formulated using techniques such as those described herein. Such combinations may be formed or reformed into, for example, membranes and fibers.

Complexes of deacetylated p-GlcNAc with polyanions such as, for example, polyacrylic acid or pectin, possessing both positive and negative charges, may be formulated. The formation of such complexes may be accomplished according to a method similar to that described by Mireleg et al. (Mireles, C. et al., 1992, in "Advances in Chitin and Chitosan", Brine, C. J. et al., eds., Elsevier Publishers, Ltd.). Deacetylated p-GlcNAc and polyacrylic acid, carrageenan or pectin, for example, are dissolved in HCl and NaCl, respectively, and the reactant solutions, with equal pH, are mixed. This operation produces effective molecules possessing both positive and negative characteristics, useful, for example, in the immobilization of enzymes and therapeutic compounds.

Further, derivatives, such as partially deacetylated derivatives and carboxymethyl derivatives of the p-GlcNAc of the invention, can be used to coat liposomes to give them greater stability. Liposomes are artificially constructed microspheres of lipid bilayer useful, for example, for drug delivery. The compositions of present invention can be used to form negatively charged phospholipids bound to positively charged deacetylated p-GlcNAc enclosing an aqueous compartment. These constructions are designed to contain and deliver pharmaceuticals or other components more efficiently than would otherwise be possible by way of oral or other application. Such constructions can be produced by utilizing the p-GlcNAc compositions of the invention in conjunction with methods well known in the art. See, for example, the Dong and Rogers (Dong, C. and Rogers, J. A., 1991, Journal of Controlled Release, 17:217–224) which is incorporated by reference in its entirety.

Certain derivatizations of the p-GlcNAc of the invention, or of its derivatives, may be preferred for specific applications, which are described in Section 5.6, below. For example, sulfated, phosphorylated, and/or nitrated p-GlcNAc derivatives may be preferred as lipoprotein lipase activators. N-acyl p-GlcNAc derivatives may also be preferred for anticoagulants, in addition to being preferred for, for example, use in production of artificial blood vessels, antiviral compounds, anti-tumor (specifically, cancer cell aggregating compounds), dialysis and ultrafiltration membranes, and in the production of controlled release drug delivery systems. O-alkyl p-GlcNAc and its deacetylated derivatives may also be preferred in the production of controlled release drug delivery systems. N-alkyl p-GlcNAc derivatives may be preferred as antibacterial agents. Oxido deaminated derivatives may be preferred as anti-cancer agents, specifically their use in conjunction with immunotherapy for cancer cells. Deacetylated p-GlcNAc derivatives may be preferred as wound healing agents. N-alkylidene and N-arylidene p-GlcNAc derivatives may be preferred for the enzyme immobilization applications.

5.5. REFORMULATIONS

The p-GlcNAc of the invention, as well as its deacetylated derivatives and/or their derivatizations, such as those described, above, in Section 5.4, may be dissolved and subsequently reformulated into a variety of shapes and configurations.

Solution of the p-GlcNAc of the invention can be achieved by treatment with dimethyl acetamide (DMA)/ lithium chloride. p-GlcNAc may be readily dissolved by stirring in a DMA solution containing 5% LiCl (by weight of the DMA). Water soluble p-GlcNAc derivatives, such as p-GlcNAc salts, may be dissolved in water. P-GlcNAc which has been at least about 75% deacetylated may be put into solution in, for example, a mild acidic solution, such as 1% acetic acid. p-GlcNAc derivatives that are water-insoluble may be put into solution in organic solvents.

Derivatization of p-GlcNAc in DMA:LiCl with phenyl isocyanates may be used to produce carbanilates. Further, derivatization of p-GlcNAc in DMA:LiCl with toluene-p-sulphonylchloride may be used to produce toluene-p-sulfonate.

The p-GlcNAc of the invention, its deacetylated derivatives, and/or their derivatizations in solution may then be precipitated and reformulated into shapes which include, but are not limited to, mats, strings, microspheres, microbeads, membranes, fibers, powders, and sponges. Further, ultrathin (i.e., less than about 1 micron thick) uniform membranes may be formulated. Additionally, pharmaceutical formulations such as pills, tablets and capsules can be prepared.

Such reformulations may be achieved, by, for example, taking advantage of the fact that pure p-GlcNAc is insoluble in solutions such as water and alcohol, preferably ethanol. Introduction, by conventional means, such as by injection, for example, of the p-GlcNAc-containing DMA/LiCl mixture into such a water or alcohol, preferably ethanol, solution will bring about the reprecipitation, and therefore reformulation, of the dissolved p-GlcNAc. Such a pure p-GlcNAc reformulation is demonstrated in the Working Example presented, below, in Section 11. In the case of water soluble p-GlcNAc derivatives, reformulations may be achieved by reprecipitating in such organic solvents as, for example, ethyl acetate or isopropanol. Reformulations of p-GlcNAc which has been at least about 75% deacetylated may be achieved by reprecipitating in an alkaline solution. Water-insoluble p-GlcNAc derivatives may be reformulated by reprecipitation in aqueous solutions, such as, for example, water.

Deacetylated p-GtcNAc, in conjunction with oxidized cotton, may be formulated to produce p-GlcNAc/cotton hybrid materials improving the wet-strength of paper products. An oxidized cotton substrate can be approached closely by the deacetylated p-GlcNAc chain which has a flat ribbonlike shape, similar to that of cellulose. Such proximity maximizes the contribution of the van der Waals forces to the forces promoting adsorption, thus enhancing the wet-strength properties of the hybrid p-GlcNAc-cellulose materials.

p-GlcNAc membranes and three-dimensional p-GlcNAc matrices may be produced via methods which provide for the formation of controlled average pore sizes within either the membranes or the matrices. Pore size can be controlled in membranes and matrices by varying the amount of p-GlcNAc material used, and by the addition of certain solvents such as methanol or ethanol, with ethanol being preferred, in specific amounts, ranging from about 5% to about 40%, prior to the formation of membranes and/or matrices. In general, the greater the percentage of solvent, the smaller the average pore size formed will be. The Example presented, below, in Section 15, demonstrates the synthesis and characterization of such porous p-GlcNAc structures. Thus, the p-GlcNAc may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The p-GlcNAc may be used in place of, or in addition to, the excipients and fillers. Tablets may be coated using p-GlcNAc using methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

5.6. USES

The p-GlcNAc of the invention, as well as its deacetylated derivatives and their derivatizations, such as those described, above, in Section 5.4, and reformulations, such as those described above, in Section 5.5, have a variety of uses. For example, the non-toxic, non-pyrogenic, biodegradable, and biocompatible properties of the molecules of the invention, in addition to the advantageous properties of the p-GlcNAc and its derivatives, as described herein, lend themselves to applications in such diverse fields as agriculture, cosmetics, the biomedical industry, animal nutrition and health, and the food, chemical, photographic, and pharmaceutical industries.

5.6.1. BIOMEDICAL USES OF p-GlcNAc MATERIALS

5.6.1.1. DRUG IMMOBILIZATION/DELIVERY USES

Biomedical uses of p-GlcNAc material may include, for example, enzyme and/or drug immobilization/delivery methods. The p-GlcNAc/drug formulations of the invention can provide additional benefits to the known drug formulations, including, for example, increased effectiveness, reduced toxicity and improved bioavailability. Such p-GlcNAc/drug formulations can act as therapeutic agents which may include, but are not limited to, antitumor agents, antibiotics, antibacterials, antifungals, anti-virals and anti-inflammatory drugs.

The drug/p-GlcNAc compositions can be formulated, for example, by immobilizing a given drug by covalent or non-covalent attachment to, the p-GlcNAc or p-GlcNAc derivates of the invention. Techniques for covalent or non-covalent attachment are well known to those skilled in the art, and may be as described. The drug/p-GlcNAc compositions of the invention can also be formulated, for example, by encapsulating a given molecule within p-GlcNAc or an p-GlcNAc derivative. Encapsulation methods are described, above, in Section 5.4.

Upon attachment or encapsulation of the molecule, assays commonly employed by those of skill in the art may be utilized to test the activity of the particular molecule or molecules attached, thereby ensuring that an acceptable level of biological activity (e.g., a therapeutically effective activity) is retained by the attached molecule or encapsulated molecule.

p-GlcNAc/drug formulations and p-GlcNAc/drug encapsulations may be delivered to a patient via a variety of routes using standard procedures well known to those of skill in the art. For example, such delivery may be site-specific, oral, nasal, intravenous, subcutaneous, intradermal, transdermal, intramuscular or intraperitoneal administration. Both p-GlcNAc/drug formulations and p-GlcNAc/drug encapsulations may be formulated to function as controlled, slow release vehicles, as described in this Section, below.

With respect to site-specific delivery, administration methods may include, but are not limited to injection, implantation, arthroscopic, laparoscopic or similar means. p-GlcNAc membranes and/or gels as well as microspheres and sponges are preferred for such site-specific delivery methods.

There are numerous advantages in using the p-GlcNAc based drug delivery systems of the invention. Traditional drug administration by injection is commonly used with proteins and many other drugs. However, repeated doses lead to oscillating blood drug concentrations and affect patient comfort and compliance. Oral administration can be advantageous since it allows for a more varied load of the drug to be released and is less discomforting to the patient. However, proteins and other compounds are denatured and degraded in the stomach.

An improved oral administration, however, is achieved by the compound-containing p-GlcNAc molecules or p-GlcNAc compound encapsulations of the invention by providing a protective environment for the drug once administered. For example, the p-GlcNAc of the invention protects a compound, such as a protein, from the acidic and enzymatic environment of the stomach. The p-GlcNAc system releases the compound via diffusion and/or encapsulation degradation once it reaches the intestinal region, where it is effectively absorbed into the blood stream. These p-GlcNAc systems of the invention can be used, for example, to deliver proteins, such as, insulin, as well as many other compounds. Liposomes coated with p-GlcNAc derivatives or p-GlcNAc derivatives-alginate encapsulations are preferred for such oral delivery methods.

Upon introduction of the compound-containing p-GlcNAc and/or p-GlcNAc encapsulations into a patient, the p-GlcNAc of the invention biodegrades, such that the attached compounds are gradually released into the bloodstream of the patient, thus providing a method for controlled compound or drug delivery.

Deacetylated or partially deacetylated p-GlcNAc species may be produced having a predictable rate of biodegradability. For example, the percentage of deacetylation affects the rate at which the p-GlcNAc species degrades. Generally, the higher the percentage of deacetylation, the faster the rate of biodegradability and resorption will be. Thus, the degree of p-GlcNAc biodegradability and the in vivo rate of resorption may be controlled during the p-GlcNAc's production. Examples of the production and characterization of such p-GtcNAc materials are presented in Section 18, below. p-GlcNAc materials having such controllable biodegradability rates may be formulated into membranes, gels, sponges, microspheres, fibers, and the like. These p-GlcNAc products adhere and mold to tissues, both soft and hard tissues, in the human body with no need for suturing. The p-GlcNAc materials may, for example, be applied during general or minimally invasive surgery, such as laparoscopic surgery.

Compound-p-GlcNAc and p-GlcNAc encapsulations have a variety of applications as therapeutic drug delivery systems. Compounds which may be encapsulated within or attached to (covalently or non-covalently) the p-GlcNAc, or a derivative of the invention are, for example, antitumor compounds, antibiotics, antibacterials, antifungals, antivirals, small peptide and non-peptide molecules, vitamins and other health-related food additives. Anti-tumor drugs which can be attached to, or encapsulated within the p-GlcNAc of the invention include, but are not limited to, those listed in this Section, below.

Additionally, combinations of two or more molecules may be encapsulated within or attached to the p-GlcNAc of the invention to provide a synergistic effect. For example, anti-tumor agents such as thioguanine combined with cytosine arabinoside (ara-C) are contemplated for use in the invention as an improved treatment for acute nonlymphocytic leukemia. Other synergistic combinations include tamoxifen with cisplatin for breast cancer, and prostaglandins with cisplatin for breast and prostate cancer. Additionally, many other synergistic combinations of anti-cancer drugs, known to those of skill in the art, may be used with the p-GlcNAc and p-GlcNAc derivative formulations of the invention.

Further, gene therapy agents, such as anti-sense DNA and ribozyme systems may also be encapsulated within the p-GlcNAc or p-GlcNAc derivatives of the invention. Immunotherapeutic compounds (e.g., vaccines), such as tumor specific antigens, that can elicit an immune response (e.g., a cytotoxic T-lymphocyte response) against a specific tumor type (e.g., melanoma) can also be attached to, or encapsulated within the p-GlcNAc of p-GlcNAc derivatives of the invention by methods known in the art.

The drug delivery systems described herein are feasible for use with any anti-tumor drug. For example, the use of such anti-tumor drug delivery systems is demonstrated in the Example presented in Section 20, below. Such drugs are well known to those of skill in the art, and may be formulated into p-GlcNAc gels or membranes, for example, so as to provide site-specific slow-release delivery directly to the tumor or to the region vacated by the tumor following surgery. Such an immobilized slow-release p-GlcNAc drug product can act as an important initial defensive procedure after surgery. Such p-GlcNAc anti-tumor drug delivery systems are particularly useful in treating tumors which are totally or partially inaccessible through surgery, such as, for example, is the case with certain brain tumors.

Additionally, the use of p-GlcNAc/compound and p-GlcNAc encapsulations of the invention for the development of new anti-tumor drug formulations is desirable given that the p-GlcNAc polymer has chemical properties and characteristics making possible the formulation and delivery of some drugs that have heretofore been difficult to formulate and deliver. For example, taxol, a microtubule spindle inhibitor drug used to treat breast cancer, is hydrophobic and requires the addition of polyoxyethylated castor oil in order to solubilize it as a liquid infusion for intravenous delivery. The hydrophobic nature of taxol makes it an ideal compound for formulation with p-GlcNAc polymer materials for topical controlled release delivery. The Example presented in Section 23, below, presents such a p-GlcNAc/taxol formulation. Additional targets for p-GlcNAc anti-tumor systems include, but are not limited to, skin, GI tract, pancreatic, lung, breast, urinary tract and uterine tumors, and HIV-related Kaposi's sarcomas.

For example, anti-tumor drugs that may be formulated with the p-GlcNAc and p-GlcNAc encapsulation system of the invention include, but are not limited to, the following categories and specific compounds alkylating agents, antimetabolite agents, anti-tumor antibiotics, vinea alkaloid and epidophyllotoxin agents, nitrosoureas, enzymes, synthetics, hormonal therapeutic biologics and investigational drugs.

Such alkylating agents may include, but are not limited to nitrogen mustard, chlorambucil, cyclophosphamide, ifosfamide, melphalan, thiptepa and busulfan.

Antimetabolites can include, but are not limited to, methotrexate, 5-fluorouracil, cytosine arabinoside (ara-C), 5-azacytidine, 6-mercaptopurine, 6-thioguanine, and fludarabine phosphate. Antitumor antibiotics may include but are not limited to doxorubicin, daunorubicin, dactinomycin, bleomycin, mitomycin C, plicamycin, idarubicin, and mitoxantrone. Vinca alkaloids and epipodophyllotoxins may include, but are not limited to vincristine, vinblastine, vindesine, etoposide, and teniposide.

Nitrosoureas such as, but not limited to carmustine, lomustine, semustine and streptozocin. Enzymes can include, but are not limited to L-asparagine.

Synthetics can include, but are not limited to Dacrabazine, hexamethylmelamine, hydroxyurea, mitotane procabazine, cisplatin and carboplatin.

Hormonal therapeutics can include, but are not limited to corticosteriods (cortisone acetate, hydrocortisone, prednisone, prednisolone, methyl prednisolone and dexamethasone), estrogens, (diethylstibesterol, estradiol, esterified estrogens, conjugated estrogen, chlorotiasnene), progestins (medroxyprogesterone acetate, hydroxy progesterone caproate, megestrol acetate), antiestrogens (tamoxifen), aromastase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole).

Biologics can include, but are not limited to interferons, interleukins, tumor necrosis factor, and biological response modifiers.

Investigational Drugs can include, but are not limited to alkylating agents such as Nimustine AZQ, BZQ, cyclodisone, DADAG, CB10-227, CY233, DABIS maleate, EDMN, Fotemustine, Hepsulfam, Hexamethylmelamine, Mafosamide, MDMS, PCNU, Spiromustine, TA-077, TCNU and Temozolomide; antimetabolites, such as acivicin, Azacytidine, 5-aza-deoxycytidine, A-TDA, Benzylidene glucose, Carbetimer, CB3717, Deazaguanine mesylate, DODOX, Doxifluridine, DUP-785, 10-EDAM, Fazarabine, Fludarabine, MZPES, MMPR, PALA, PLAC, TCAR, TMQ, TNC-P and Piritrexim; antitumor antibodies, such as AMPAS, BWA770U, BWA773U, BWA502U, Amonafide, m-AMSA, CI-921, Datelliptium, Mitonafide, Piroxantrone, Aclarubicin, Cytorhodin, Epirubicin, esorubicin, Idarubicin, Iodo-doxorubicin, Marcellomycin, Menaril, Morpholino anthracyclines, Pirarubicin, and SM-5887; microtubule spindle inhibitors, such as Amphethinile, Navelbine, and Taxol; the alkyllysophospholipids, such as BM41-440, ET-18-OCH3, and Hexacyclophosphocholine; metallic compounds, such as Gallium Nitrate, CL286558, CL287110, Cycloplatam, DWA2114R, NK121, Iproplatin, Oxaliplatin, Spiroplatin, Spirogermanium, and Titanium compounds; and novel compounds such as, for example, Aphidoicolin glycinate, Ambazone, BSO, Caracemide, DSG, Didemnin, B, DMFO, Elsamicin, Espertatrucin, Flavone acetic acid, HMBA, HHT, ICRF-187, Iododeoxyuridine, Ipomeanol, Liblomycin, Lonidamine, LY186641, MAP, MTQ, Merabarone SK&F104864, Suramin, Tallysomycin, Teniposide, THU and WR2721;and Toremifene, Trilosane, and zindoxifene.

Antitumor drugs that are radiation enhancers are preferred for instances in which radiation therapy treatment is to be prescribed, either in lieu of, or following surgery. Examples of such drugs include, for example, the chemotherapeutic agents 5'-fluorouracil, mitomycin, cisplatin and its derivatives, taxol, doxorubicin, actinomycin, bleomycins, daunomycins, and methamycins.

Dose ranges for anti-tumor drugs may be lower than, equal to or greater than the typical daily doses prescribed for systemic treatment of patients. Higher doses may be tolerated in that the drugs are delivered locally at the site of a tumor, whereas other tissues, therefore, including blood cells, are not as readily exposed to the drugs. For example, dosages of 5'-FU equivalent to 50% of the standard dosages used to treat colorectal cancer with 5'-FU in humans (300–450 mg/m$^2$ i.v. daily for 5 days) resulted in an 80-90% reduction in volume of ectopic HT29 colon cancer tumor implants in scid mice. The use of the p-GlcNAc membrane as a drug delivery matrix for the administration of 5'-FU reduced the dosage required to dramatically reduce tumor volume by 50% as compared to intravenuous control animals. Details regarding this data can be found in Example 21, below.

Further, doses of such drugs are well known to those of skill in the art and can be easily found in such compendia as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publishers, THE CHEMOTHERAPY SOURCE BOOK, Williams and Wilkens Publishers, online services such as the Cancer Lit®, U.S. National Cancer Institute database, as well as reports of pharmacological studies such as "A MultiCenter Randomized Trial of Trial of Two Doses of Taxol" Nabholtz, J. M., Gelmon, K., Bontenbal, M. et al. Medical Education Services Monograph—1994 Bristol-Myers Squibb Company Publication; "Randomized Trial of Two Doses of Taxol in Metastatic Breast Cancer: An Interim Analysis" Nabholtz, J. M., Gelmon, K., Bontenbal, M., et al. 1993, Proc. Am. Clin. Oncol., 12:60. Abstract 42 Alternatively, such doses can be routinely determined by using standard techniques well known to those of skill in the art such as, for example, those described, below, at the end of this Section.

Certain anti-tumor agents are vesicants, including dactinomycin, daunomycin, doxorubicin, estramustine, mechlorethamine, mitomycin C, vinblastine, vincristine and videsine; while certain anti-tumor drugs are irritants, including carmustine, decarbazine, etoposide, mithrmycin, streptozocin and teniposide. Vesicants and irritants cause adverse side-effects including extravasation and irritation of tissues with pain, redness, swelling, and other symptoms. Further, tissue necrosis can result from some of the side effects. The p-GlcNAc membrane and gel materials of the invention used for the topical, controlled release of anti-tumor drugs have wound healing properties. Normal tissues that are in contact with vesicant or irritant anti-tumor drugs delivered by the p-GlcNAc membrane and gel formulations of the invention are, therefore, not as readily damaged and will heal faster due to the active healing effects of the p-GlcNAc component of the anti-tumor drug-containing p-GlcNAc and p-GlcNAc-drug encapsulations of the invention.

The compound-containing p-GlcNAc and p-GlcNAc-compound encapsulations of the invention may, additionally, be used for the treatment of infections. For such an application, antibiotics, either water soluble or water insoluble, may be immobilized/formulated in p-GlcNAc based materials, such as, for example, gels and membranes. Antibiotics are well known to those of skill in the art, and include, for example, penicillins, cephalosporins, tetracyclines, ampicillin, aureothicin, bacitracin, chloramphenicol, cycloserine, erythromycin, gentamicin, gramacidins,.kanamycins, neomycins, streptomycins, tobramycin, and vancomycin Doses of such drugs are well known to those of skill in the art, and may, alternatively, routinely be determined using standard techniques well known to those of skill in the art, such as, for example, are described, below, at the end of this Section.

Such p-GlcNAc antibiotic products may be used to treat bacterial infections that occur either externally, e.g., on skin, scalp, dermal ulcers or eyes, or internally, e.g, localized infections of the brain, muscles, abdomen. A prominent application is for treatment of HIV-related opportunistic infections.

The compound-containing p-GlcNAc and p-GlcNAc-compound encapsulation systems of the invention may be formulated with anti-inflammatory drugs to control dysfunctional activity of the inflammatory and immune processes. For example, p-GlcNAc may be formulated with non-steroidal anti-inflammatory drugs (NSAIDs) and used to the reduction of local pain and inflammation induced by diseases such as rheumatoid arthritis, osteoarthritis and systemic lupus, to name a few. The localized delivery of such NSAIDs using the p-GlcNAc gel or membrane/drug delivery systems of the invention may serve to reduce NSAID side effects, which may include gastric irritation, azotemia, platelet disfunction and liver function abnormalities. NSAIDs are well known to those of skill in the art and include inhibitors of cycloxygenase, such as aspirin, etodolac, fenoprofen and naproxen. Other anti-inflammatory drugs may be utilized as part of the compound-containing p-GlcNAc and p-GlcNAc encapsulation systems of the invention, such as, for example, inhibitors of lipid inflammatory mediators, such as leucotrienes. Doses for such drugs are well known to those of skill in the art, and may, alternatively, routinely be determined using standard techniques well known to those of skill in the art, such as, for example, are described, below, at the end of this Section.

The compound-containing p-GlcNAc and p-GlcNAc-compound encapsulation systems of the invention may additionally be formulated with antifungal agents, using techniques described above, for the treatment of specific fungal diseases. Antifungal agents are well known to those of skill in the art, and may include, for example, amphotericin, anisomycin, antifungone, blastomycin, griseofulvins, and nystatin. Doses of such drugs are well known to those of skill in the art, and may, alternatively, routinely be determined using standard techniques well known to those of skill in the art, such as, for example, are described, below, at the end of this Section.

The compound-containing p-GlcNAc and p-GlcNAc-compound encapsulation systems of the invention may also be formulated with antiprotozoal agents, using techniques described above, for the treatment of specific protozoal infections. Antiprotozoal agents are well known to those of skill in the art, and may include, for example, antiamoebin, antiprotozin, monomycin, paromomycin and trichomycin. Doses of such drugs are well known to those of skill in the art, and may, alternatively, routinely be determined using standard techniques well known to those of skill in the art, such as, for example, are described, below, at the end of this Section.

The compound-containing p-GlcNAc and p-GlcNAc-compound encapsulation systems of the invention may be formulated with spermicidal compounds, using techniques such as those described, above, to produce effective contraceptives. Appropriate spermicides are well known to those of skill in the art. Doses of such spermicides are well known to those of skill in the art, and may, alternatively, routinely be determined using standard techniques well known to those of skill in the art, such as, for example, are described, below, at the end of this Section.

The compound-containing p-GlcNAc and p-GlcNAc-compound encapsulation systems of the invention may, still further, be formulated using therapeutic protein agents. Such formulations may be produced using, for example, techniques such as those described above. By utilizing such p-GlcNAc therapeutic protein systems, it is possible to deliver specific proteins directly to desired target sites and to effect slow release of the proteins at such sites. Examples of possible proteins include, but are not limited to insulin, monoclonal antibodies, breast cancer immunotoxin, tumor necrosis factor, interferons, human growth hormone, lymphokines, colony stimulating factor, interleukins and human serum albumin. Doses of such therapeutic protein agents are well known to those of skill in the art and may be found in pharmaceutical compedia such as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publ., THE CHEMOTHERAPY SOURCE BOOK, Williams and Wilkens Publishers, and may, alteratively, routinely be determined using standard techniques well known to those of skill in the art, such as, for example, are described, below, at the end of this Section.

The compound-containing p-GlcNAc and p-GlcNAc-compound encapsulation delivery systems of the invention can also be formulated as nutritional and vitamin supplements.

Because the p-GlcNAc materials of the invention are themselves immunoneutral, in that they do not elicit an immune response in humans, such p-GlcNAc devices, as described above, comprising p-GlcNAc membranes, 3D porous matrices and/or gels that harbor immobilized drugs, may deliver such drugs in a manner that there is no immune response. Certain additional materials, such as natural alginates and synthetic polymers, may be used in some cases to construct such devices in combination with the p-GlcNAc material. For instance, a polymeric delayed-release drug delivery system can be manufactured in a manner similar to that suggested by A. Polk (Polk, A. et al., 1994, J. of Pharmaceutical Sciences, 83(2):178–185). In such a procedure, deacetylated p-GlcNAc is reacted with sodium alginate in the presence of calcium chloride to form microcapsules containing the drug to be delivered and released under appropriate conditions and over a certain lapse of time.

The therapeutically effective doses of any of the drugs or agents described above, in conjunction with the p-GtcNAc-based systems described herein, may routinely be determined using techniques well known to those of skill in the art. A "therapeutically effective" dose refers to that amount of the compound sufficient to result in amelioration of symptoms of the processes and/or diseases described herein.

Toxicity and therapeutic efficacy of the drugs can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.6.1.2. p-GlcNAc CELL ENCAPSULATION USES p-GlcNAc encapsulated cells may be formulated, and such p-GlcNAc encapsulated cells may be administered to a patient, via standard techniques well known to those of skill in the art. See, for example, the techniques described, above, in Section 5.6.1.1. Alternatively, see, for example, Aebisher et al. (Aebisher, P. et al., in "Fundamentals of Animal Cell Encapsulation and Immobilization", 1993, CRC Press, pp. 197–224), Yoshioke et al., (Yoshioke, T. et al., 1990, Biotechnol. Bioeng. 35:66) and U.S. Pat. No. 4,749,620, each of which is incorporated herein by reference in its entirety. Cells may be encapsulated by, on, or within p-GlcNAc or partially deacetylated p-GlcNAc membranes, three-dimensional p-GlcNAc porous matrices, or p-GlcNAc gels.

Three-dimensional matrices can be seeded with cells and used in certain applications without further encapsulation.

Alternatively, cells can be encapsulated into microspheres or droplets of p-GlcNAc-based polymer gels such as, for example, a p-GlcNAc-lactate polyelectrolyte polymer (a polycationic polymer). Gels, droplets or microspheres into which cells have been encapsulated may then be coated with a second polyelectrolyte of opposite charge (e.g., with a polyanion, such as an alginate) to form an outer capsule which provides immuno-isolation for the encapsulated cells, thus reducing the risk of immune rejection by the host organism.

Additionally, cells entrapped in p-GlcNAc gels, three-dimensional p-GlcNAc matrices, or both, can be loaded into thermoplastic capsules in yet another method of formulation. Thermoplastic-based capsules can also be utilized to provide immuno-protection for implanted cells in a host organism. Such thermoplastic capsules are made of materials such as hydroxyethyl methylacrylate-methylmethacrylate copolymer (HEMA-MMA). Thermoplastic-derived microcapsules are formed, for example, by the coextrusion of a solution of HEMA-MMA in polyethylene glycol and the cell-containing p-GlcNAc matrix and/or gel medium, into an appropriate organic solvent such as hexadecane. See, for example, the method described by Aebisher et al. (Aebisher, P. et al., in "Fundamentals of Animal Cell Encapsulation and Immobilization", 1993, CRC Press, pp. 197–224).

The p-GlcNAc cell encapsulations have a variety of applications. First, they may be utilized for the delivery of therapeutic compounds, synthesized and secreted by cells attached to and encapsulated in the membranes, matrices or gels.

For example, and not by way of limitation, the p-GlcNAc/cell encapsulations may be used for delivery of insulin in the treatment of diabetes, nerve growth factor for the treatment of Alzheimer's disease, factor VIII and other clotting factors for the treatment of hemophilia, dopamine for the treatment of Parkinson's disease, enkephalins via adrenal chromaffin cells for the treatment of chronic pain, dystrophin for the treatment of muscular dystrophy, and human growth hormone for the treatment of abnormal growth. For example, dopamine-producing adrenal chromaffin cells may be encapsulated for the treatment of Parkinson's Disease and for the relief of chronic pain. Also, pancreatic islet cells may be encapsulated for the treatment of insulin-dependent diabetes mellitus. Further, the p-GlcNAc/cell encapsulations may be used for delivery of the above peptides and proteins, or other peptides and proteins, as gene products in vivo for use in gene therapies. For example, using recombinant DNA techniques, a gene for which a patient is deficient could be placed under the control of viral or tissue specific promotor. The recombinant DNA construct containing the gene could be used to transform or transfect a host cell which is cloned and then clonally expanded and is engineered so as to secrete the said gene product then encapsulated into the p-GlcNAc/cell encapsulations of the invention and used to deliver the gene product as a therapy.

Additionally, such encapsulated cells may act to compensate for the loss of a specific organ or tissue and/or may be used to augment the reduced function of such a specific tissue or organ of the body. For example, encapsulated liver cells may be used to augment reduced liver function, and may, for example, be utilized as a temporary measure prior to the administration of a liver transplant. As another example, encapsulated thyroid, parathyroid or pancreas cells may be administered to compensate for the loss of these glands.

Because the p-GlcNAc materials of the invention are themselves immunoneutral, as they do not elicit an immune response in humans, it is possible to engineer and construct devices consisting of p-GlcNAc membranes, three-dimensional porous p-GlcNAc matrices and/or p-GlcNAc gels that harbor attached cells which can deliver cell-based therapeutics in a manner such that the cells are immuno-isolated, i.e., no anti-cell host immune response is elicited. Certain additional materials, such as, for example, natural alginates and synthetic polymers, may be used to construct such devices in addition to the p-GlcNAc material itself.

p-GlcNAc/cell encapsulation compositions may additionally be utilized for the delivery of cells to seed tissue regeneration. Applications of specific cell types encapsulated for the seeding of cell growth leading to tissue regeneration at the site of an injury may include, but are not limited to regeneration of skin, cartilage, nerves, bone, tendon, ligaments, liver and blood vessels. The tissue regeneration applications of cells encapsulated in p-GlcNAc materials are advantageous, in part, because of the ability of the p-GlcNAc material to adhere to injured tissue, to provide a substrate for mammalian cell growth, and to undergo bioresorption coincident with the growth of new healthy tissue during the tissue regeneration process at the site of injury.

5.6.1.3. UTILIZING p-GlcNAc MATERIALS FOR THE PREVENTION OF POST-SURGICAL-ADHESIONS

Additionally, p-GlcNAc membranes may be used to provide a biodegradable, biocompatible mechanical barrier to prevent post-surgical adhesions. The Example presented in Section 17, below, demonstrate such a p-GlcNAc application. Solid p-GlcNAc or p-GlcNAc derivatives formulated into membranes or sponges may be utilized for such an application. Preferred membranes are thin, generally less than about 1 mm in thickness. Preferable p-GlcNAc derivatives are p-GlcNAc derivatives which have been about 50–80% deacetylated. Such p-GlcNAc derivatives will generally be resorbed approximately 7–21 days post-implantation.

Liquid p-GlcNAc derivatives are also suitable for use in the prevention of post-surgical adhesions. Preferable liquid p-GlcNAc derivatives for such an application are deacetylated p-GlcNAc salt derivatives and carboxymethyl p-GlcNAc derivatives. A p-GlcNAc derivative which is particularly preferred for the prevention of post-surgical adhesions is a p-GlcNAc-lactate derivative, especially a p-GlcNAc-lactate gel derivative. As used herein, the term p-GlcNAc-lactate means that the lactic acid moiety is functionally attached to a partially or fully deacetylated poly-$\beta$-1→4-N-acetylglucosamine of the invention. Such p-GlcNAc-lactate derivatives may be formulated using propylene glycol and water, as, for example, described in Section 17.1. p-GlcNAc-lactate derivatives may be produced having high and low viscosities, which allows for the ability to tailor the p-GlcNAc used to the specific indication of interest. For example, it may be useful to use a p-GlcNAc product having a lower viscosity for delivery through a syringe or via a spray, while it may be desirable to use a p-GlcNAc product having a higher viscosity, and therefore greater lubrication properties, when the indication is an orthopedic one.

For the prevention of post-surgical adhesions, solid p-GlcNAc formulations are suitable for clearly circumscribed wound sites. Such p-GlcNAc formulations should be applied following the surgical procedure and the material should completely cover the traumatized tissue. It can be applied either in conjunction with either general or minimally invasive (e.g., laparoscopic) surgical procedures. The solid p-GlcNAc formulations can be cut and applied using standard surgical procedures and instrumentation well known to those of skill in the art.

The liquid p-GlcNAc formulations can be applied, for the prevention of post-surgical adhesions, in larger areas prone to form such postoperative adhesions. The p-GlcNAc-lactate gel, for example, can be applied before the surgical procedure to provide additional lubrication and thus reduce the amount of traumatized tissue. Alternatively, the liquid p-GlcNAc formulation, such as p-GlcNAc-lactate, can be applied following the surgical procedure to form a physical barrier to prevent postoperative adhesion formation.

The p-GlcNAc material can be painted, sprayed or dropped from a syringe device onto the wounded site. In laparoscopic procedures, low viscosity materials can, for example, be delivered with standard suction irrigation devices. Higher viscosity materials will require pressure to reach its target. The pressure can be provided by a compressed gas powered piston or a syringe type device.

The amount of liquid p-GlcNAc formulation, such as the p-GlcNAc-lactate gel formulation, required for prevention of post-surgical adhesions is proportional to the extent of the traumatized tissue. The p-GlcNAc material administered should be applied in the range of 0.1 ml to 1.5 ml per sq. cm of surface area.

Various animal models which are known in the art can be used to test the post-surgical adhesion formulations of the invention. These include, but are not limited to, the Rat cecum model (Harris, E. W., et al., 1992, Journal of Investigative Surgery, 5:260; and the Rabbit uterine horn model (Diamond, M. P., et al., 1987, Microsurgery, 8:197.

5.6.1.4. BIODEGRADABLE p-GlcNAc BARRIERS p-GlcNAc materials having a controllable rate of biodegradation may be useful as, for example barriers having a variety of applications. For example, such barriers may be utilized to promote hemostasis. The successful use of such a hemostatic p-GlcNAc application is demonstrated in the Example presented, in Section 19, below. Additionally, p-GlcNAc-based material, such as thick gels, sponges, films and membranes may be used for such hemostatic applications. The p-GlcNAc based materials, when applied directly to bleeding surfaces, arrest bleeding by providing a mechanical matrix that promotes clotting. The p-GlcNAc based materials adhere to the site of application and seal the boundaries of the wound. This reduces the amount of blood loss, protects the forming clot and facilitates the clotting process.

The preferred solid materials for such an application are deacetylated p-GlcNAc membranes and sponges. The preferred thick gels can be formulated from water plus soluble derivatives like deacetylated p-GlcNAc salts and carboxymethyl p-GlcNAc derivatives. The thick gels of the invention should have a viscosity of 50,000 cps or greater. For example, and not by way of limitation, one formulation of such a gel is presented in Example 17.1 in formulating p-GlcNAc-lactate as a gel.

Applications for the hemostatic agents described above include, but are not limited to, uses in diagnostic procedures such as biopsy wounds in, for example, liver and kidney; in trauma wounds, for example, spleen, liver and blood vessel injuries; in standard and minimally invasive surgical procedures, for example, endometriosis surgery and operations on the gallbladder; in soft and hard tissue wound repair, for example, skin wounds and burn healing; in surgical procedures, in particular, for splenic wounds; and for blood vessel puncture diagnostic and treatment procedures such as catheterization and balloon angioplasty procedures.

The solid p-GlcNAc based materials of the invention can be applied using standard surgical procedures, and can be used with both standard and minimally invasive surgical interventions. The thick gels of the invention can be delivered, for example, by extrusion from a syringe type device or in combination with a membrane or film. The membrane or film can be manufactured from a p-GlcNAc based material or other natural or synthetic materials.

In connection with the blood vessel puncture procedures mentioned above, the hemostatic agents of the invention may be applied at the time when a catheter sheath is being removed from a blood vessel. A device that detects the removal of the catheter sheath from the blood vessel can be developed using electronic or mechanical systems that monitor chemical, physical or other differences between the tissue inside and outside of the vessel. For example, the differential in fluid dynamics or heat dissipation can be detected when a probe is removed from the vessel; at that point a signal is sent to initiate the application of the hemostatic agent.

Further, p-GlcNAc materials may be utilized to provide periodontal barriers for the separation of soft and hard tissue during the repair process following periodontal surgery in order to promote uniform tissue repair, to provide biodegradable contact lenses, corneal shields or bone grafts, to provide surgical space fillers, to promote soft tissue augmentation, particularly in the skin for the purpose of reducing skin wrinkles, and as urinary sphincter augmentation, for the purpose of controlling incontinence.

5.6.1.5. OTHER BIOMEDICAL USES OF p-GlcNAc MATERIALS

Other biomedical uses of p-GlcNAc materials include, for example, the use of such materials as cell culture substrates. For example, as shown in the Working Example presented in Section 12, below, the p-GlcNAc of the invention acts as a very efficient substrate for mammalian cells grown in culture. Further, three-dimensional configurations of p-GlcNAc may be used as medium components which will allow three-dimensional cell culture growth.

The cell substrate capabilities of the p-GlcNAc of the invention may also be utilized in vivo. Here, the p-GlcNAc of the invention, or a derivative thereof, as described herein, may act to facilitate tissue regeneration (e.g., regeneration of connective tissue covering teeth near the gum line, vascular grafts, ligament, tendon, cartilage, bone, skin, nerve tissues). The p-GlcNAc molecules of the invention may, therefore, for example, have extensive plastic surgery applications.

Deacetylated p-GlcNAc is preferred for use as a sealant of vascular grafts. Deacetylated p-GlcNAc derivatives such as N-carboxymethyl and N-carboxybutyl deacetylated p-GlcNAc are preferred as tissue regeneration reagents. N-carboxymethyl deacetylated p-GlcNAc may, for example, be inoculated into the cornea to induce neovascularization.

Further biomedical applications of the p-GlcNAc of the invention or of its derivatives, as described herein, may involve the molecules' use in wound dressing, wound healing ointments, and surgical sutures, sponges, and the like. Such promotion of wound healing and reduction of scarring is illustrated, below, in examples 17 and 22. These properties are useful in stimulating tissue repair, and accelerates, strengthen and improve the quality of healing. p-GlcNAc based materials may be used for injury related or surgically induced wounds in both soft and hard tissue. For example, such wounds include venous stasis ulcers, burn healing and surgical wounds in the eye or other tissues where quality of healing or fibrosis may be important.

Still further, such molecules may be used, for example, in the treatment of osteoarthritis, in the reduction of blood serum cholesterol levels, as anti-viral agents, as antibacterial agents, as immunomodulators, as anticoagulants, as dialysis and ultrafiltration membranes, as anti-tumor agents, as contact lens material, and as oral adsorbents for uremic toxins when administered to kidney failure patients. Microcrystalline p-GlcNAc suspensions or water soluble p-GlcNAc derivatives are preferred for the treatment of arthritis, by, for example, injection directly into arthritic joints.

p-GlcNAc has additional applications as a component of artificial or donor skin. For example, p-GlcNAc, preferably as non-woven p-GlcNAc films, may be applied to split thickness skin donor sites, over, for example, donor dermis.

Deacetylated p-GlcNAc to which a protease, such as pepsin, has been attached may be used for the controlled digestion of proteins in contact with such p-GlcNAc/protease compounds.

5.6.2. AGRICULTURAL USES OF p-GlcNAc MATERIALS

The p-GlcNAc of the invention or its derivatives may be used in various agricultural applications, as well. Such applications include, but are not limited to insecticide, fungicide, bactericide, and nematocide applications. N-carboxymethyl deacetylated p-GlcNAc derivatives are preferred for use as effective bacteriostatic reagents. N-alkyl p-GlcNAc derivatives may be preferred for fungicide applications. Additionally, the molecules of the invention may be used in various soil treatment applications, including, but not limited to, fertilizer compositions. Further, controlled release of agrochemicals may be achieved by entrapping such chemicals via the immobilization, encapsulation, and other methods described, above, in this Section. Additionally, analogs of, for example, Rhizobium nodulation factors and/or nitrogen fixation inducers may be immobilized onto, and administered via, the p-GlcNAc and/or p-GlcNAc derivatives of the invention.

5.6.3. NUTRITION/FOOD INDUSTRY USES OF p-GlcNAc MATERIALS

The p-GlcNAc of the invention and its derivatives as described herein additionally have applications in the fields of animal and human nutrition. For example, the molecules of the invention may be used as feed ingredients Techniques such as those described, above, in this Section, may be used in the production of controlled release products in animal systems. Additionally, the biomedical applications described above may be utilized in animal systems by incorporating routine modifications well known to those of ordinary skill in the art.

Food industry applications of the p-GlcNAc of the invention and of its derivatives, as described herein, may include, but are not limited to anticholesterol (i.e., hypocholesterolemic compounds), fat-binding compounds, emulsifiers, carriers, preservatives, seasonings, and food texturizers, in addition to fruit coatings, and food packaging products. For example, in terms of cholesterol and fat binding, p-GlcNAc derivatives exhibit strong binding activity towards lipids. Deacetylated and appropriately hydrolyzed p-GlcNAc derivatives also bind to lipids and dietary cholesterol. (Vahouny, G. V., 1983, Journal of Clinical Nutrition 38:278–284). It is possible that p-GlcNAc exerts a hypocholestrolemic effect by forming micelles with cholesterol and lipids, causing them eventually to be excreted (Hirano, S., 1990, in, "The International Symposium on Chitin Derivatives in Life Sciences").

5.6.4. COSMETIC USES OF p-GlcNAc MATERIALS

Cosmetic applications of the p-GlcNAc of the invention may include, but are not limited to, the production of products for hair and skin care. Skin care products may include, for example, cosmetics utilizing deacetylated p-GlcNAc salts, carboxymethyl p-GlcNAc-containing products, and cosmetic packs containing deacetylated p-GlcNAc and such derivatives as hydroxypropyl-, N-succinyl-, and quaternary p-GlcNAc derivatives. Hair products may include, for example, carboxymethyl p-GlcNAc-containing products, and film-forming p-GlcNAc derivatives.

5.6.5. CHEMICAL ENGINEERING APPLICATIONS OF p-GlcNAc MATERIALS

The p-GlcNAc of the invention and its derivatives have a variety of applications that are useful in the chemical engineering industry. For example, p-GlcNAc may be used as a coupling agent for adhesion of metals to polymers, membranes formed by glycol p-GlcNAc may be used in desalination applications, and membranes formed by other p-GlcNAc derivatives may be used for transport of halogen ions. Other applications may include the production of flame retardants, and the manufacture of metal chelating compounds and compounds capable of removing trace and heavy metals from liquids as well as water-soluble industrial pollutants, such as PCBs, for example. p-GlcNAc and/or p-GlcNAc derivatives may be used in photographic applications. For example, the ability of p-GlcNAc and/or p-GlcNAc derivatives to chelate metals, such as silver halides, may be utilized by contacting photographic solutions to recast mats, such as thin membranes, of p-GlcNAc and/or p-GlcNAc derivatives.

6. EXAMPLE: PHYSICAL CHARACTERIZATION OF PREPARATIONS OF PURE p-GlcNAC

Presented in this Example, are circular dichroism (CD) and infra-red spectra (IR) analyses of p-GlcNAC and deacetylated p-GlcNAC membranes.

6.1. MATERIALS AND METHODS p-GlcNAC and commercial "chitin" preparations:

The p-GlcNAc used in the CD studies was prepared using the Mechanical Force purification method described, above, in Section 5.3.1.

Commercial "chitin" was purchased from NovaChem, Ltd., PO Box 1030 Armdale, Halifax, Nova Scotia, Canada, B3L 4K9.

The p-GlcNAC membranes used in the IR studies were prepared by either the Mechanical Force purification method as described, above, in Section 5.3.1, or by the Chemical/Biological purification method, as described, above, in Section 5.3.2, as indicated.

The commercial "p-GlcNAc" preparations were cast into membranes by dissolving in a dimethylacetamide solution containing 5% lithium chloride, and layering onto distilled, deionized water until membranes precipitated.

p-GlcNAC derivatives and treatments:The Deacetylated p-GlcNAC used in both the CD and IR studies was prepared by treatment of the p-GlcNAC with 50% NaOH at 60° C. for 2 hours. The heat-denatured p-GlcNAC membranes used in the IR studies were modified by boiling in 0.2 mM EDTA for 3 minutes. p-GlcNAc was autoclaved for 30 minutes at 122° C.

CD techniques: Solid state CD techniques were carried out essentially according to Domard (Domard, A., 1986, Int. J. Macromol. 8:243–246).

6.2. RESULTS

6.2.1. CD ANALYSIS

Figure 3B:
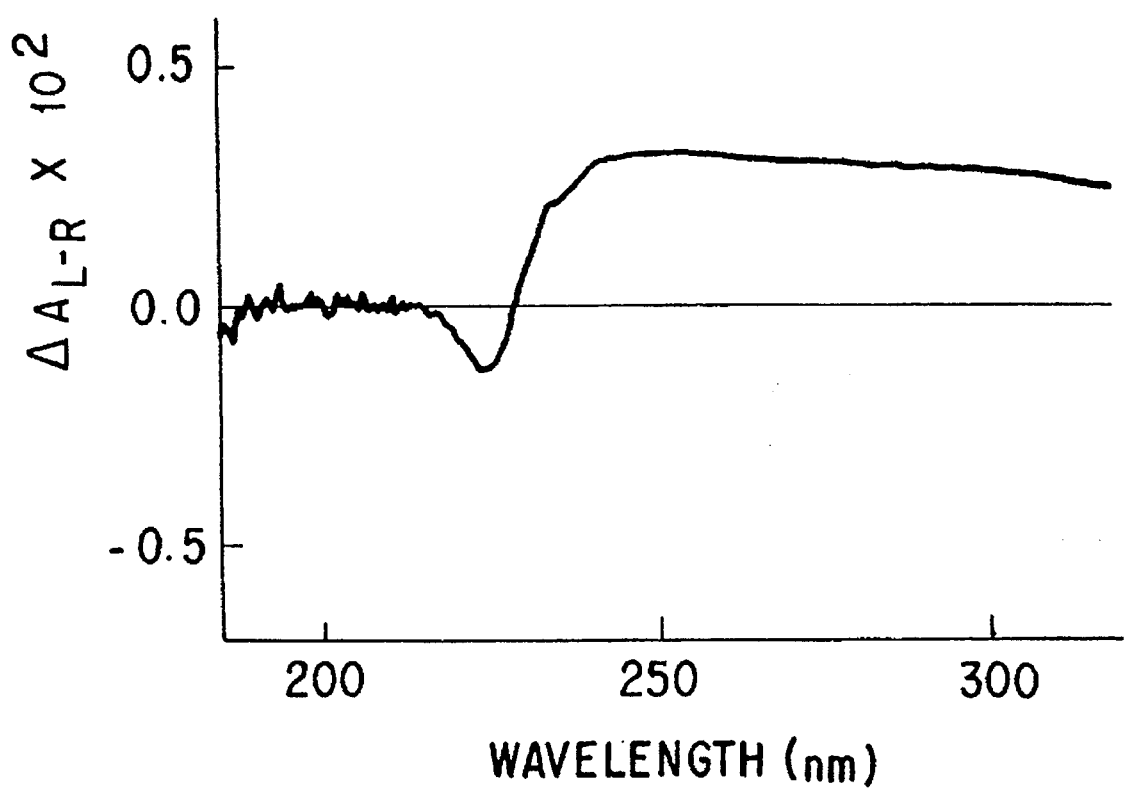
FIG. 3B. Circular dichroism spectra of solid membranes of Deacetylated p-GlcNAc. The disappearance of the 211 nm minimum and 195 nm maximum observed in pure p-GlcNAc (FIG. 3A) indicates complete deacetylation under the conditions used, as described in Section 5.4 below.

In the CD spectra obtained from untreated p-GlcNAc (FIG. 3A), the expected $n-\pi^*$ and $\pi-\pi^{**}$ optically active electronic transitions (220–185 nM) were observed due to the presence of the carbonyl group in the acetyl moiety of p-GlcNAc. Such peaks are completely absent in the CD spectrum obtained from the deacetylated p-GlcNAc product, as shown in FIG. 3B.

6.2.2. IR SPECTRA ANALYSIS

The IR spectra obtained in this study are consistent with the chemical structure of p-GlcNAc. Additionally, the sharp definition of each IR peak is indicative of the presence of an ordered and regular (i.e., pseudocrystalline) structure in the p-GlcNAc fibers. See FIG. 4A for the IR spectrum of p-GlcNAc purified via the Mechanical Force purification method, and FIG. 4D for the IR spectrum of p-GlcNAc purified via the Chemical/Biological method. For comparison, see FIG. 4B, which demonstrates the IR spectrum of a commercial "chitin" preparation.

Figure 4E:
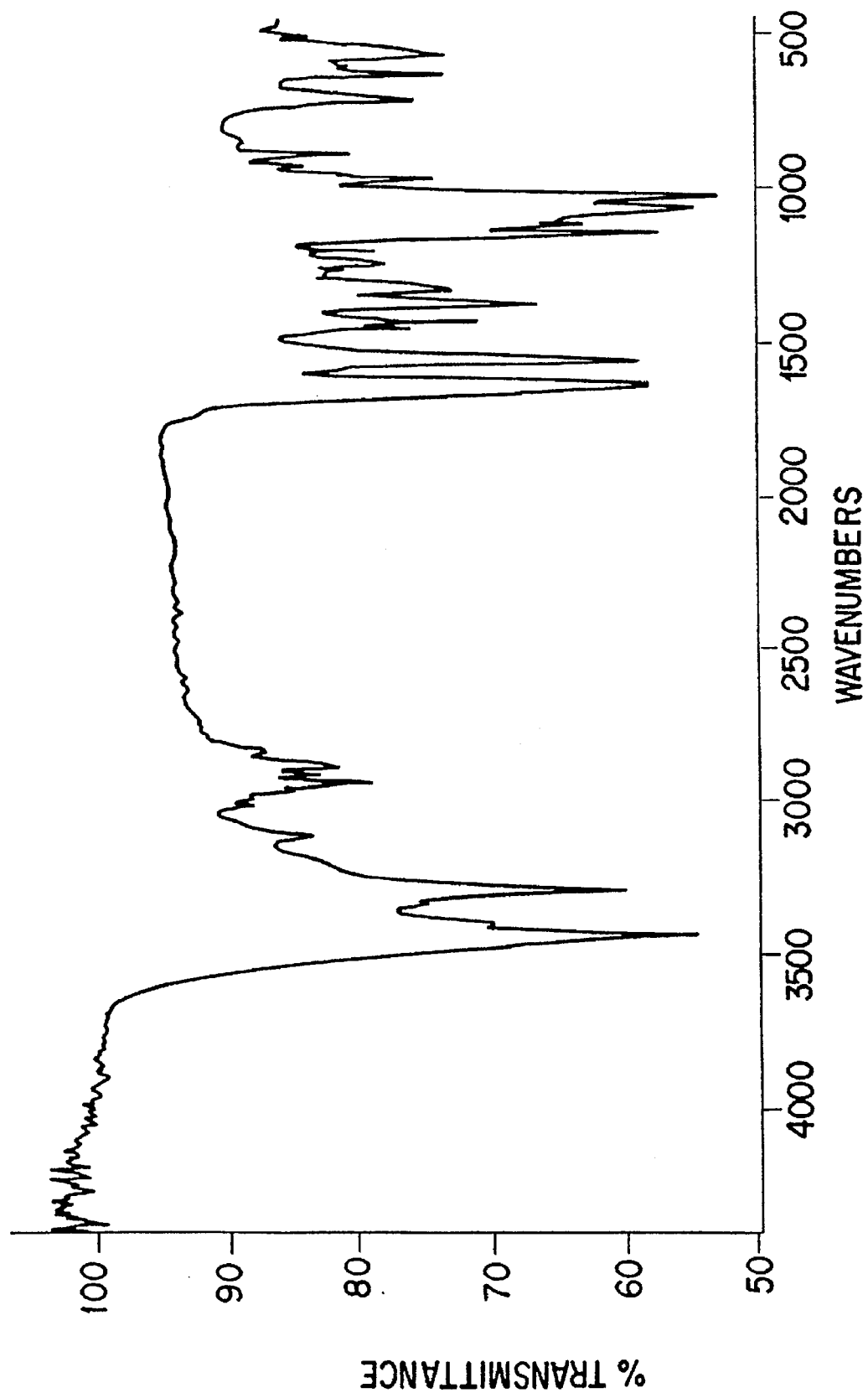
FIG. 4E. Infra-red spectrum analysis of a p-GlcNAc membrane prepared by the mechanical force purification method, as described in Section 5.3.1, below, following autoclaving.

The IR spectrum obtained from the autoclaved p-GlcNAc material (FIG. 4E) does not differ visibly from the IR spectrum observed in FIG. 4A. This data indicates that the p-GlcNAc material may be sterilized by autoclaving with no loss of polymer structure.

7. EXAMPLE: PURIFICATION OF p-GlcNAC USING THE MECHANICAL FORCE PURIFICATION METHOD

In this section, p-GlcNAC was purified using the Mechanical Force technique described above, in Section 5.3.1.

7.1. MATERIALS AND METHODS/RESULTS

Diatom culture conditions: The diatom species *Thalassiosira fluviatilis* was grown in culture according the procedures described, above, in Sections 5.1 and 5.2.

SEM procedures: The SEM techniques used here are as those described, below, in Section 12.1.

p-GlcNAc Purification procedure:p-GlcNAc was purified from the diatom culture by utilizing the Mechanical Force technique described above, in Section 5.3.1. Specifically, the p-GlcNAc fibers were separated from the diatom cell bodies by subjecting the contents of the culture to three short bursts of top speed mixing motion in a Waring blender. Total time of the three bursts was about one second. The resulting suspension was centrifuged at 3500 rpm in a Sorvall GS-4 fixed angle rotor, for 20 minutes at about 10° C. The supernatant was decanted, and centrifuged again, this time at 4000 rpm, in a Sorvall GS-4 fixed angle rotor for 20 minutes at about 10° C. Once again, the supernatant was decanted and centrifuged at 4000 rpm at 10° C. The final supernatant of the third centrifugation was clear, with little, if any, visible flocs floating in the liquid. The clear supernatant was decanted into a Buchner filtration unit equipped with a Supor-800 polyether sulfone filter membrane with 0.8μm pore size (Gelman, Inc.), suction was then applied and the liquid was filtered from the fiber suspension, allowing the fibers to be collected on the membrane. The collected fibers were washed with 1 liter of distilled, deionized $H_2O$ at 70° C. When almost all of the water had been drained, fibers were washed, with suction, with 1 liter of 1 N HCl at 70° C. When most of the acid solution had been drained, the fibers were washed with 1 liter of distilled, deionized $H_2O$ at 70° C., using suction. When most of the wash water had been drained, the fibers were washed with 1 liter of 95% ethanol at room temperature, and vacuum was applied. The filter membrane on which the white fiber membrane had been collected was then removed from the filtration unit and the membrane and its membrane support was dried in a drying oven at 58° C. for 20 minutes, after which the membrane and its support was placed in a desiccator for 16 hours.

Figure 6A:
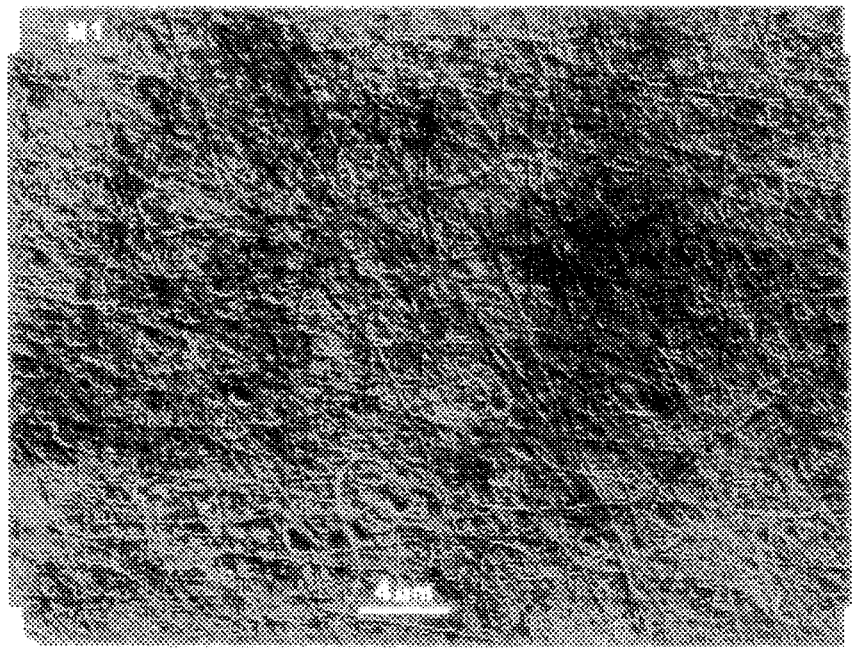
FIG. 6A–B. Transmission electron micrographs (TEM) of a p-GlcNAc membrane prepared by the mechanical force purification method as described in Section 5.3.1, below. Magnification.
Figure 6B:
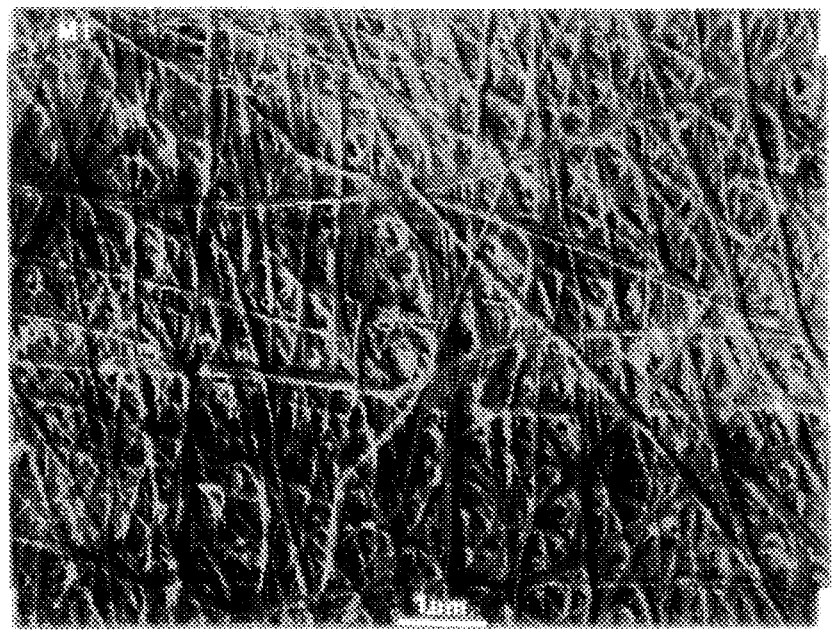

Following this purification procedure, the yield of p-GlcNAc from a 1000 ml culture was 6.85 milligrams per liter of diatom culture. SEM photographs of the membrane formed by the collection of the p-GlcNAC fibers via this technique is shown in FIG. 6.

8. EXAMPLE: PURIFICATION OF p-GlcNAC USING THE BIOLOGICAL/CHEMICAL PURIFICATION METHOD

In this section, p-GlcNAC was purified using two of the Chemical/Biological techniques described above, in Section 5.3.2. Briefly, p-GlcNAC was purified via HF treatment, in one case, and via acid treatment/neutralization in the second case.

8.1. MATERIALS AND METHODS/RESULTS

Diatom culture conditions: The diatom species *Thalassiosira fluviatilis* was grown in a culture according to the procedures described, above, in Sections 5.1 and 5.2.

SEM procedures: The techniques utilized in this study were as described, below, in Section 12.1.

Figure 7A:
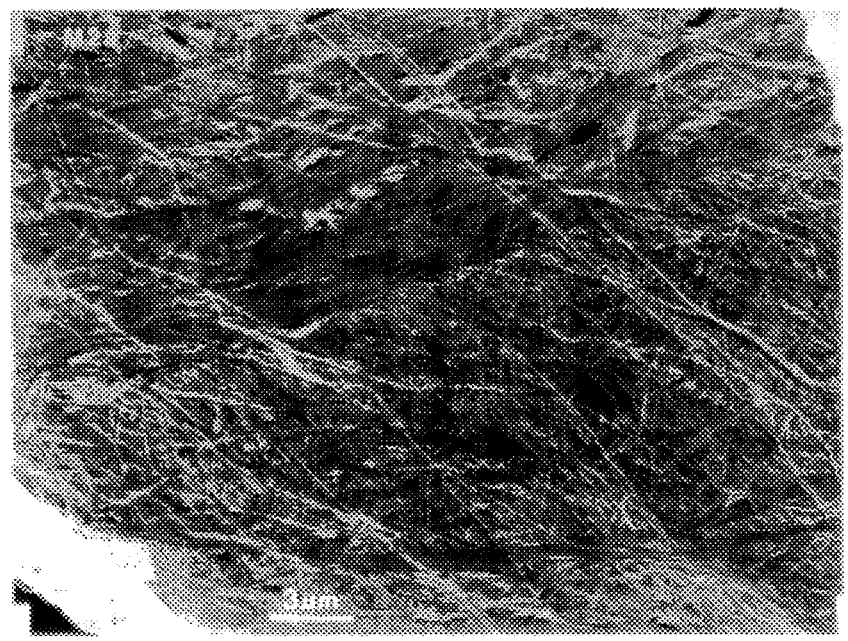
FIG. 7A–B. Transmission electron micrographs (TEM) of a p-GlcNAc membrane by HF treatment as described in the discussion of the chemical/biological purification method in Section S.3.2, below. Magnification:, (FIG. 7A), 5270x.
Figure 7B:
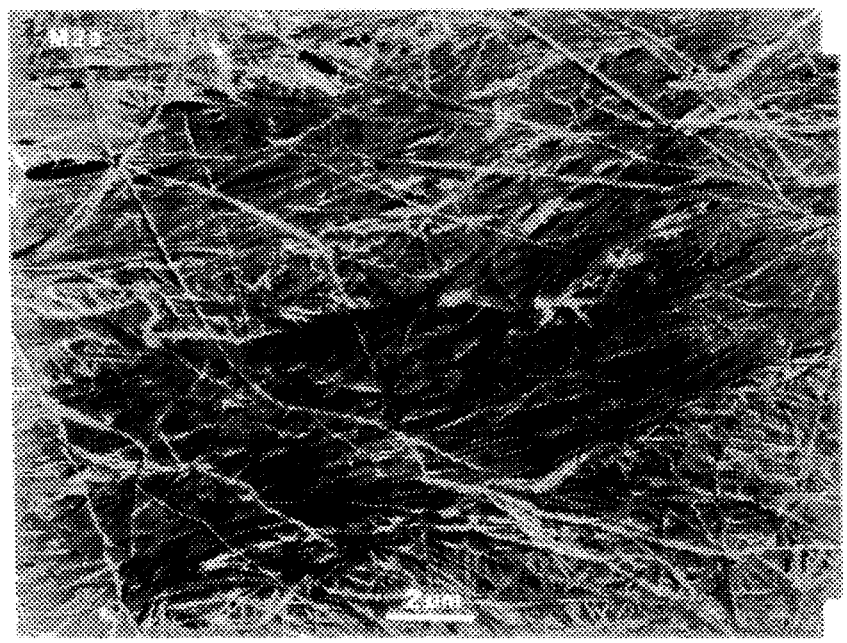
Figure 8A:
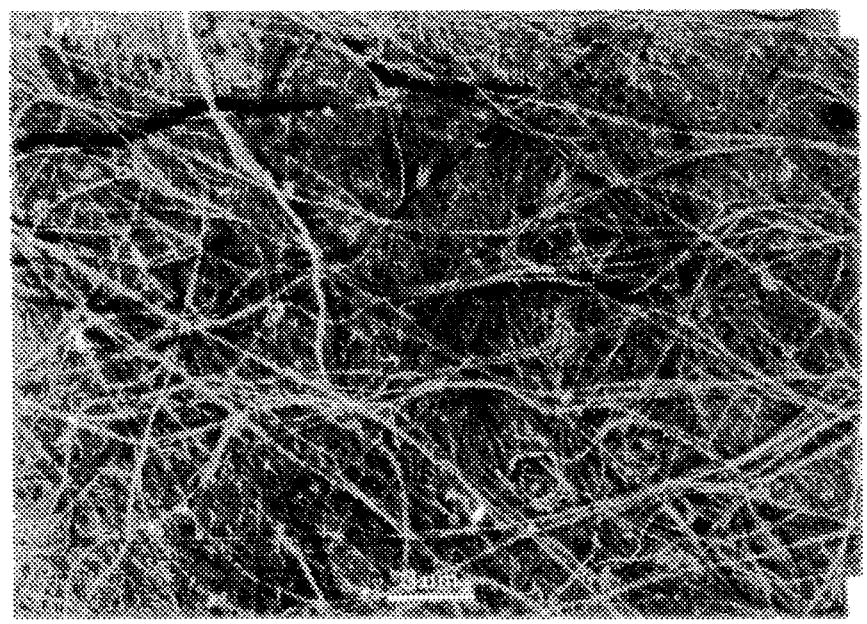
FIG. 8A–B. Transmission electron micrographs (TEM) of a p-GlcNAc membrane prepared by the acid treatment/ neutralization variation of the chemical/biological purification method, as described in Section 5.3.2, below. Magnification.
Figure 8B:
Figure 9A:
FIG. 9A. Scanning electron micrograph depicting a p-GlcNAc membrane prepared by the acid treatment/ neutralization variation of the chemical/biological purification method as described in Section 5.3.2, below. Magnification: 200x.
Figure 9B:
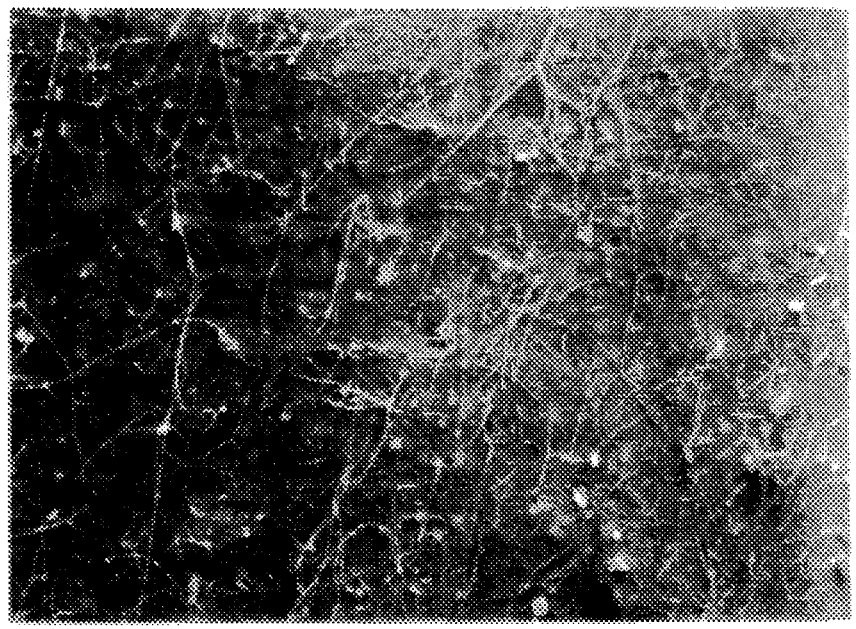
FIG. 9B. Scanning electron micrograph depicting a p-GlcNAc membrane prepared by the acid treatment/ neutralization variation of the chemical/biological purification method as described in Section 5.3.2, below. Magnification: 1000x.
Figure 9C:
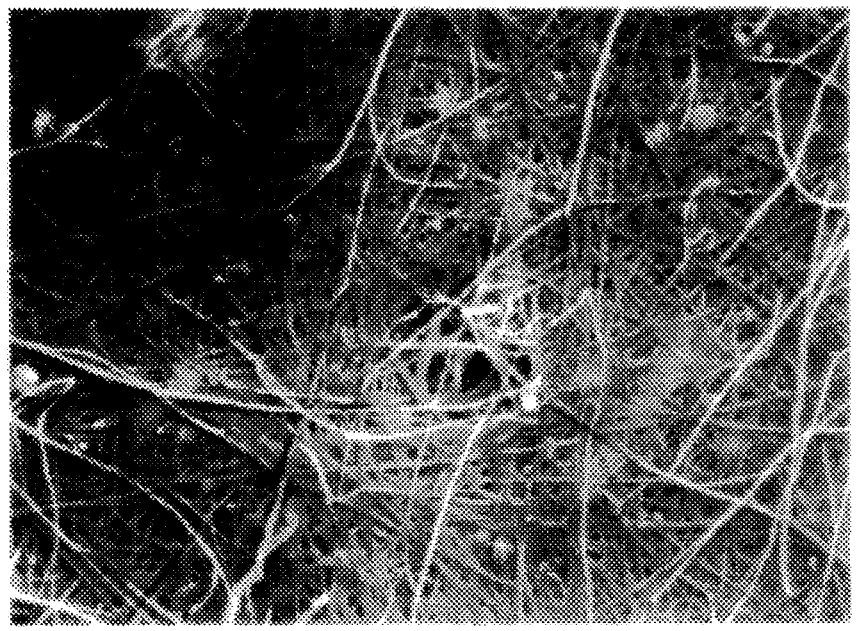
FIG. 9C. Scanning electron micrograph depicting a p-GlcNAc membrane prepared by the acid treatment/ neutralization variation of the chemical/biological purification method as described in Section 5.3.2, below. Magnification: 5000x.
Figure 9D:
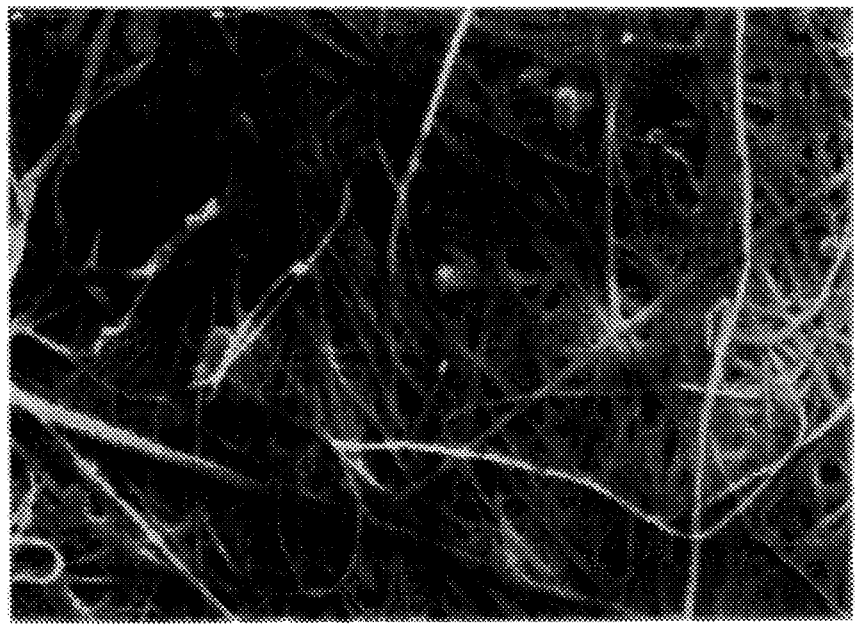
FIG. 9D. Scanning electron micrograph depicting a p-GlcNAc membrane prepared by the acid treatment/ neutralization variation of the chemical/biological purification method as described in Section 5.3.2, below. Magnification: 10,000x.
Figure 9E:
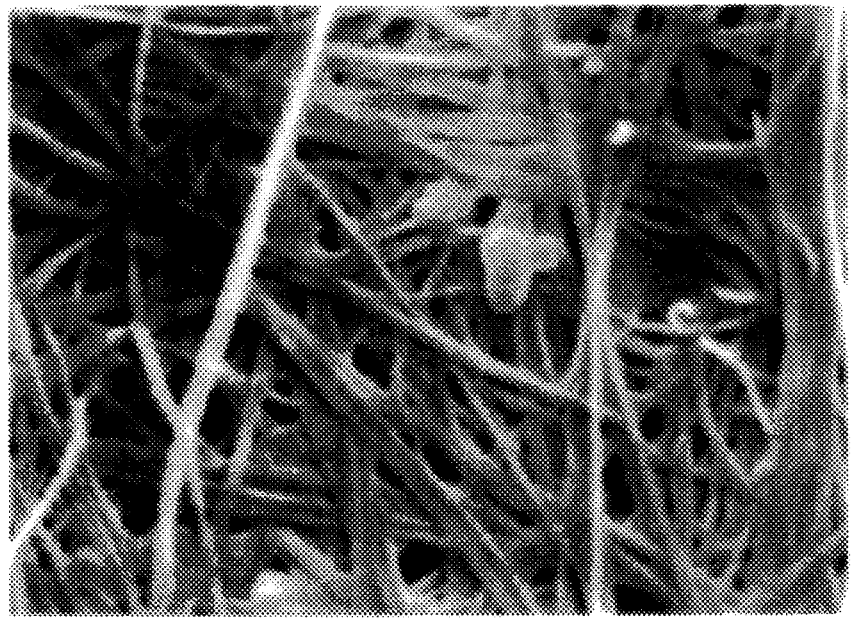
FIG. 9E. Scanning electron micrograph depicting a p-GlcNAc membrane prepared by the acid treatment/ neutralization variation of the chemical/biological purification method as described in Section 5.3.2, below. Magnification: 20,000x.

Purification procedure: First, p-GlcNAc was purified by HF treatment, the results of which are shown in FIG. 7. Specifically, under a fume hood, 2.42 ml of a 49% (29N) HF solution was added to the diatom contents of the culture, at room temperature, for each 1000 ml of the volume of the original cell culture, resulting in a 0.07 M HF solution. The mixture was then shaken vigorously for about 30 seconds, causing persistent foam to appear over the liquid. The container was allowed to stand undisturbed for 5–6 hours to allow heavy particulates to settle. At the end of this time, a layer of foam had formed, while the liquid itself was divided into two strata: first, a narrow, very dark green layer resting on the bottom of the container below a second, much lighter colored grayish-green and murky phase which represented perhaps 85–90% of the total volume of liquid. The foam layer was carefully siphoned off, using a capillary glass tube and vacuum suction. The grayish cloudy supernatant was then siphoned off, with care being taken not to disturb the dark bottom layer, which consisted mainly of settled cell bodies, and was transferred to a separate plastic container. The grayish cloudy supernatant was allowed to stand undisturbed for an additional 16 hours. The liquid was initially almost colorless, light grey, but not transparent. After 16 hours settling time, a small amount of foam remained on top of the main body of liquid and a small amount of green matter had settled on the bottom of the container. The liquid was lighter in color, but still not transparent. The foam on top of the liquid was siphoned off as before. The main body of liquid was then carefully siphoned off, leaving behind the small amount of settled green material at the bottom of the container. The liquid which had thus been isolated, contained the majority of the p-GlcNAc fibers and some impurities.

To remove proteins and other unwanted matter liberated by the diatoms during the preceding steps in the procedure from the fiber-containing liquid, the suspension of fibers and cell remnants was washed with sodium dodecyl sulfate (SDS). Specifically, the necessary volume of a 20% SDS solution was added to make the final concentration of the liquid 0.5% SDS by volume. The container holding the liquid was sealed, secured in a horizontal position on a shaking machine, and agitated for 24 hours at about 100 shakes a minute. Soon after shaking began, large flocs of white p-GlcNAc fibers appeared in the suspension, and a considerable amount of foam accumulated in the head space of the containers. At the end of the SDS washing, the contents of the containers were transferred to a Buchner filtration equipment provided with a Supor-800 polyether sulfone filter membrane, with 0.8 micron pore size (Gelman, Inc.). The liquid was filtered with suction, and the p-GlcNAc fibers in the liquid were collected on the filter membrane.

The p-GlcNAc fibers collected on the filter membrane were then washed further. First, the fibers were washed with hot (70° C.) distilled, deionized H₂O, using three times the volume of the original suspension. With a water jet using distilled, deionized H₂O, the white fiber clumps collected on the filter membrane of the Buchner filter were transferred to a Waring blender, and the fiber clumps were disintegrated with about 10 short mixing bursts. The suspension of disintegrated fibers was transferred to a Buchner filter funnel equipped with a polyether sulfone filter membrane as described above, and the liquid was removed under suction. The collected fibers were washed with 1000 ml of hot (70° C.) 1N HCl solution, and subsequently further washed with 1000 ml hot (70° C.) distilled, deionized H₂O. Finally, the fibers were washed with 1000 ml 95% ethanol at room temperature, and filtered to dryness. The fiber membrane and the filter membrane supporting the fiber membrane were then dried in a drying oven at 58° C. for 20 minutes. The membrane and membrane support was then placed in a desiccator for 16 hours. The membrane was then carefully detached from the filter membrane.

Second, p-GlcNAc was purified by using the acid treatment/neutralization method described, above, in Section 5.3.2. Specifically, the p-GlcNAc was processed as described earlier in this Section, until prior to the SDS wash step, at which point the solution was neutralized to a pH of approximately 7.0 by the addition of a 2.9M Tris solution. The p-GlcNAc yield from this particular purification procedure was 20.20 milligrams per liter of diatom culture, although, on average, approximately 60 milligrams per liter diatom culture are obtained. SEM micrographs of membranes formed during the purification procedure are shown in FIGS. 8A–B and 9A–9E.

9. EXAMPLE: p-GlcNAc DEACETYLATION

Figure 11A:
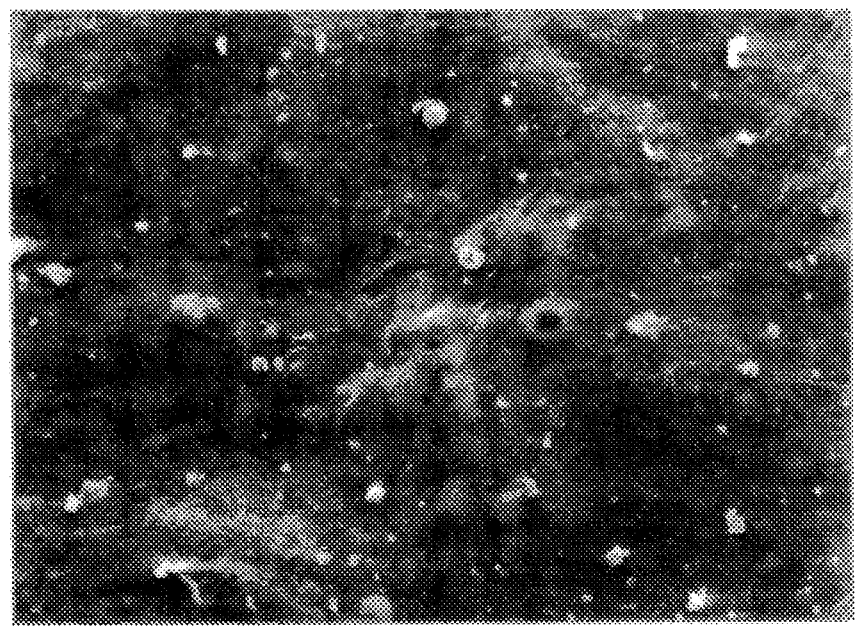
FIG. 11A–B. Scanning electron micrographs of a deacetylated p-GlcNAc mat. Magnification.
Figure 11B:

A p-GlcNAc membrane was suspended in an aqueous 50% NaOH solution. The suspension was heated at 80° C. for 2 hours. The resulting deacetylated membrane was dried and studied by scanning electron microscopy, as shown in FIG. 11A—B.

10. EXAMPLE: p-GlcNAc BIOCOMPATIBILITY

In this Example, it is demonstrated that the p-GlcNAc of the invention exhibits no detectable biological reactivity, as assayed by elution tests, intramuscular implantation in rabbits, intracutaneous injection in rabbits, and systemic injections in mice.

10.1. MATERIALS AND METHODS

10.1.1. ELUTION TEST

Conditions for the elution test conformed to the specifications set forth in the U.S. Pharmacopeia XXII, 1990, pp. 1415–1497 and to U.S. Pharmacopeia XXII, Supplement 5, 1991, pp. 2702–2703.

Cell culture: Mouse fibroblast L929 cell line (American Type Culture Collection Rockville, Md.; ATCC No. CCL1; NCTC clone 929) was utilized. A 24 hour confluent monolayer of L929 cells was propagated in complete Minimum Essential Medium (MEM).

p-GlcNAc: a solid membrane of p-GlcNAc which had been prepared according to the Mechanical Force method of purification described, above, in Section 5.3.1, was extracted in 20 ml serum-supplemented MEM as per U.S. Pharmacopeia XXII (1990) requirements.

Controls: Natural rubber was used as a positive control, and silicone was used as a negative control. Controls were tested in the same manner as the test article, p-GlcNAc.

Extracts: Extracts were prepared at 37° C., in a humidified atmosphere containing 5% carbon dioxide, for 24 hours. Extracts were evaluated for a change in pH, and adjustments were made to bring the pH to within +/–0.2 pH units of the original medium. Adjustments were made with HCl to lower the extract pH or with NaHCO₃ to raise the extract pH. Extracts were sterile filtered by passage through a 0.22 micron filter, prior to being applied to the cell monolayer.

Dosing: 3 mls of p-GlcNAc or control extracts were used to replace the maintenance medium of cell cultures. All extracts were tested in duplicate.

Evaluation Criteria: Response of the cell monolayer was evaluated either visually or under a microscope. The biological reactivity, i.e., cellular degeneration and/or malformation, was rated on a scale of 0 to 4, as shown below. The test system is suitable if no signs of cellular reactivity (Grade 0) are noted for the negative control article, and the positive control article shows a greater than mild reactivity (Grade 2). The test article (i.e., p-GlcNAc) meets the biocompatibility test if none of the cultures treated with the test article show a greater than mild reactivity.

| Grade | Reactivity | Description of Reactivity Zone |
|---|---|---|
| 0 | None | Discrete intracytoplasmic granules; No cell lysis |
| 1 | Slightly | Not more than 20% of the cells are round, loosely attached, and without intra-cytoplasmic granules; occasional lysed cells are present |
| 2 | Mild | Not more than 50% of the cells are round and devoid of intracytoplasmic granules; extensive cell lysis and empty areas between cells |
| 3 | Moderate | Not more than 70% of the cell layers contain rounded cells and/or are lysed |

| Grade | Reactivity | Description of Reactivity Zone |
|---|---|---|
| 4 | Severe | Nearly complete destruction of the cell layers |

10.1.2. INTRAMUSCULAR IMPLANTATIONS

Animals: Healthy, New Zealand White Rabbits, male and female, (Eastern Rabbit Breeding Laboratory, Taunton, Me.) were used. Rabbits were individually housed using suspended stainless steel cages. Upon receipt, animals were placed in quarantine for 8 days, under the same conditions, as for the actual test. Hardwood chips (Sani-chips™, J. P. Murphy Forest Products, Montvale, N.J.) were used as non-contact bedding under cages. The animal facility was maintained at a temperature of 68° +/−3° F., with a relative humidity at 30–70%, a minimum of 10–13 complete air exchanges per hour, and a 12-hour light/dark cycle using full spectrum fluorescent lights. Animals were supplied with commercial feed (Agway ProLab, Waverly, N.Y.) under controlled conditions and municipal tap water ad libitum. No known contaminants were present in the feed, bedding, or water which would be expected to interfere with the test results. Animals selected for the study were chosen from a larger pool of animals. Rabbits were weighted to nearest 10 g and individually identified by ear tattoo.

p-GlcNAc: The p-GlcNAc used was as described, above, in Section 10.1.1.

Implantation Test: Two rabbits were used for each implantation test. On the day of the test, the animal skin on both sides of the spinal column was clipped free of fur. Each animal was anesthetized to prevent muscular movement. Using sterile hypodermic needles and stylets, four strips of the test p-GlcNAc (1 mm ×1 mm ×10 mm) were implanted into the paravertebral muscle on one side of the spine of each of two rabbits (2.5 to 5 cm from the midline, parallel to the spinal column., and about 2.5 cm from each other). In a similar fashion, two strips of the USP negative control plastic RS (1 mm ×1 mm ×10 mm) were implanted in the opposite muscle of each animal. Animals were maintained for a period of 7 days. At the end of the observation period, the animals were weighed and euthanized by an injectable barbiturate, Euthanasia-5 (Veterinary Laboratories, Inc., Lenexa, Kans.). Sufficient time was allowed to elapse for the tissue to be cut without bleeding. The area of the tissue surrounding the center portion of each implant strip was examined macroscopically using a magnifying lens. Hemorrhaging, necrosis, discolorations and infections were scored using the following scale: 0=Normal, 1=Mild, 2=Moderate, and 3=Severe. Encapsulation, if present, was scored by first measuring the width of the capsule (i.e., the distance from the periphery of the implant to the periphery of the capsule) rounded to the nearest 0.1 mm. The encapsulation was scored as follows:

| Capsule Width | Score |
|---|---|
| None | 0 |
| up to 0.5 mm | 1 |
| 0.6–1.0 mm | 2 |
| 1.1–2.0 mm | 3 |
| Greater than 2.0 mm | 4 |

The differences between the average scores for the p-GlcNAc and the positive control article were calculated. The test is considered negative if, in each rabbit, the difference between the average scores for each category of biological reaction for the p-GlcNAc and the positive control plastic implant sites does not exceed 1.0; or, if the difference between the mean scores for all categories of biological reaction for each p-GlcNAc article and the average score for all categories for all the positive control plastic implant sites does not exceed 1.0, for not more than one of four p-GlcNAc strips.

10.1.3. INTRACUTANEOUS INJECTIONS

Animals: New Zealand white rabbits were used and maintained as described, above, in Section 10.1.2.

p-GlcNAc: A solid membrane of p-GlcNAc which had been prepared according to the mechanical force method of purification described, above, in Section 5.3.1, was placed in an extraction flask, to which 20 ml of the appropriate medium were added. Extractions were performed by heating to 70° C. for 24 hours. Following this procedure, extracts were cooled to room temperature. Each extraction bottle was shaken vigorously prior to administration.

Intracutaneous Test: On the day of the test, animals were clipped free of fur on the dorsal side. A volume of 0.2 ml of each p-GlcNAc extract was injected intracutaneously at five sites on one side of each of two rabbits. More than one p-GlcNAc extract was used per rabbit. At five sites on the other side of each rabbit, 0.2 ml of the corresponding control was injected. Injection sites were observed for signs of erythema, edema, and necrosis at 24, 48, and 72 hours after injection. Observations were scored according to the Draize Scale for the Scoring Skin Reaction (USP Pharmacopeia XXII, 1990, 1497–1500; USP Pharmacopeia XXII, Supplement 5, 1991, 2703–2705) as shown in Table II, below:

TABLE II

| Draize Scale for Scoring Skin Reactions | |
|---|---|
| | Value |
| Erythema and Eschar Formation | |
| No erythema | 0 |
| Very slight erythema (barely perceptible) | 1 |
| Well defined erythema | 2 |
| Moderate to severe erythema | 3 |
| Severe erythema (beet redness) to slight eschar formation (injuries in depth) | 4 |
| Total possible erythema score = 4 | |
| Edema Formation | |
| No edema | 0 |
| Very slight edema (barely perceptible) | 1 |
| Slight edema (edges are well defined by definite raising) | 2 |
| Moderate edema (raised approximately 1 mm and extending beyond area of exposure) | 3 |
| Severe edema (raised more than 1 mm and extending beyond area of exposure) | 4 |
| Total possible edema score = 4 | |

All erythema and edema scores at 24, 48, and 72 hours were totaled separately and divided by 12 (i.e., 2 animals ×3 scoring periods ×2 scoring categories) to determine the overall mean score for the p-GlcNAc versus the corresponding control. Animals were weighed at the end of the observation period and euthanized by injection of a barbiturate, Euthanasia-5 (Veterinary Laboratories, Inc., Lenexa, Kans.). The results of the test are met if the difference between the p-GlcNAc and the control means reaction scores (erythema/edema) is 1.0 or less.

10.1.4. SYSTEMIC INJECTIONS

Animals: Albino Swiss mice (Mus musculus), female, (Charles River Breeding Laboratories, Wilmington, Mass.) were used. Groups of 5 mice were housed in polypropylene cages fitted with stainless steel lids. Hardwood chips (Sanichips™, J. P. Murphy Forest Products, Montvale, N.J.) were used as contact bedding in the cages. The animal facility was maintained as a limited access area. The animal rooms were kept at a temperature of 68 +/–3° F., with a relative humidity of 30–70%, a minimum of 10–13 complete air exchanges per hour, and a 12 hour light/dark cycle using full spectrum fluorescent lights. Mice were supplied with commercial feed and municipal tap water ad libitum. There were no known contaminants present in the feed, bedding, or water which would be expected to interfere with the test results. Animals selected for the study were chosen from a larger pool of animals. Mice were weighed to the nearest 0.1 g and individually identified by ear punch.

p-GlcNAc: The samples used were as described, above, in Section 10.1.1. Extracts were prepared according to the procedures described in Section 10.1.3, above.

Systemic Injection Test: Groups of 5 mice were injected with either p-GlcNAc extract or a corresponding control article, in the same amounts and by the same routes as set forth below:

| Test Article or Control Article Extracts | Dosing Route | Dose/Kg | Injection Rate |
|---|---|---|---|
| 0.9% Sodium Chloride Injection, USP (0.9% NaCl) | Intravenous | 50 ml | 0.1 ml/sec |
| 1 in 20 Alcohol in 0.9% Sodium Chloride Injection USP (EtOH:NaCl) | Intravenous | 50 ml | 0.1 ml/sec |
| Polyethylene Glycol 400 (PEG 400) | Intraperitoneal | 10 g | — — |
| Cottonseed Oil (CSO) | Intraperitoneal | 50 ml | — — |

Extracts of the p-GlcNAc prepared with PEG 400, and the corresponding control, were diluted with 0.9% NaCl, to obtain 200 mg of PEG 400 per ml. For the Intracutaneous Test, PEG 400 was diluted with 0.9% NaCl to obtain 120 mg of PEG 400 per ml.

The animals were observed immediately after injection, at 24 hours, 48 hours, and 72 hours after injection. Animals were weighed at the end of the observation period and euthanized by exposure to carbon dioxide gas. The requirements of the test are met if none of the animals treated with the p-GlcNAc shows a significantly greater biological reactivity than the animals treated with the control article.

10.2. RESULTS

10.2.1. ELUTION TEST

The response of the cell monolayer to the p-GlcNAc test article was evaluated visually and under a microscope. No cytochemical stains were used in the evaluation. No signs of cellular biological reactivity (Grade 0) were observed by 48 hours post-exposure to the negative control article or to the p-GlcNAc. Severe reactivity (Grade 4) was noted for the positive control article, as shown below in Table III:

TABLE III

REACTIVITY GRADES

| Time | p-GlcNAc | | Control Articles | | | |
| | | | Negative | | Positive | |
| | A | B | A | B | A | B |
|---|---|---|---|---|---|---|
| 0 Hours | 0 | 0 | 0 | 0 | 0 | 0 |
| 24 Hours | 0 | 0 | 0 | 0 | 4 | 4 |
| 48 Hours | 0 | 0 | 0 | 0 | 4 | 4 |

The p-GlcNAc of the invention, therefore, passes requirements of the elution test for biocompatibility, and, thus, is non-cytotoxic.

10.2.2. INTRAMUSCULAR IMPLANTATIONS

Both rabbits (A and B) tested increased in body weight and exhibited no signs of toxicity. See Table IV for data. In addition, there were no overt signs of toxicity noted in either animal. Macroscopic evaluation of the test and control article implant sites showed no inflammation, encapsulation, hemorrhage, necrosis, or discoloration. See Table IV for results. The test, therefore, demonstrates that the p-GlcNAc assayed exhibits no biological reactivities, in that, in each rabbit, the difference between the average scores for all of the categories of biological reaction for all of the p-GlcNAc implant sites and the average score for all categories for all the control implant sites did not exceed 1.0.

TABLE IV

IMPLANTATION TEST
(Macroscopic Observations)
Test Article: p-GlcNAc
Animal Species: Rabbit

| TISSUE SITE: | T1 | T2 | T3 | T4 | TEST AVERAGE | C1 | C2 | CONTROL AVERAGE |
|---|---|---|---|---|---|---|---|---|
| Animal #: A | | | | | | | | |
| Inflammation | 0 | 0 | 0 | 0 | 0 | 0 | 0 | 0 |
| Encapsulation | 0 | 0 | 0 | 0 | 0 | 0 | 0 | 0 |
| Hemorrhage | 0 | 0 | 0 | 0 | 0 | 0 | 0 | 0 |
| Necrosis | 0 | 0 | 0 | 0 | 0 | 0 | 0 | 0 |
| Discoloration | 0 | 0 | 0 | 0 | 0 | 0 | 0 | 0 |
| Total | 0 | 0 | 0 | 0 | | 0 | 0 | |
| MEAN SCORE: (total/5) | 0 | 0 | 0 | 0 | | 0 | 0 | |
| AVERAGE CONTROL VALUE: 0 | | | | | | | | |
| Animal #: B | | | | | | | | |
| Inflammation | 0 | 0 | 0 | 0 | 0 | 0 | 0 | 0 |
| Encapsulation | 0 | 0 | 0 | 0 | 0 | 0 | 0 | 0 |
| Hemorrhage | 0 | 0 | 0 | 0 | 0 | 0 | 0 | 0 |
| Necrosis | 0 | 0 | 0 | 0 | 0 | 0 | 0 | 0 |
| Discoloration | 0 | 0 | 0 | 0 | 0 | 0 | 0 | 0 |
| Total | 0 | 0 | 0 | 0 | | 0 | 0 | |
| MEAN SCORE: (total/5) | 0 | 0 | 0 | 0 | | 0 | 0 | |
| AVERAGE CONTROL VALUE: 0 | | | | | | | | |

10.2.3. INTRACUTANEOUS TEST

All of the animals increased in weight. See Table V for data. There were no signs of erythema or edema observed at any of the p-GlcNAc or control article sites. Overt signs of toxicity were not observed in any animal. Because the difference between the p-GlcNAc and control article mean reaction scores (erythema/edema) was less than 1.0, the p-GlcNAc meets the requirements of the intracutaneous test. See Table VI for results. Therefore, as assayed by this test, the p-GlcNAc demonstrates no biological reactivity.

TABLE V

Intracutaneous and Implant Tests
Body Weights and Clinical Observations
Test Article: p-GlcNAc
Animal Species: Rabbit

| Group | Animal # | Sex | Body Weight (Kg) Day 0 | Body Weight (Kg) Day 3 | Weight Change | Signs of Toxicity* |
|---|---|---|---|---|---|---|
| 0.9% NaCl & CSO | 23113 | Male | 2.51 | 2.55 | 0.04 | None |
| 0.9% NaCl & CSO | 23114 | Female | 2.43 | 2.46 | 0.03 | None |
| EtOH: NaCl & PEG 400 | 23115 | Male | 2.47 | 2.50 | 0.03 | None |
| EtOH: NaCl & PEG 400 | 23116 | Female | 2.59 | 2.63 | 0.04 | None |

TABLE V-continued

Intracutaneous and Implant Tests
Body Weights and Clinical Observations
Test Article: p-GlcNAc
Animal Species: Rabbit

| Group | Animal # | Sex | Body Weight (Kg) Day 0 | Body Weight (Kg) Day 7 | Weight Change | Signs of Toxicity* |
|---|---|---|---|---|---|---|
| Implant | A | Male | 2.74 | 2.80 | 0.06 | None |
|  | B | Female | 2.66 | 2.74 | 0.08 | None |

*Summary of Observations Day 0 Through Day 7 (Implant) and Day 0 through Day 3 (Intracutaneous).

TABLE VI

INTRACUTANEOUS TEST DRAIZE SCORES
Test Article: p-GlcNAc
(T = test, C = control)
Animal Species: Rabbit

| Animal ID # | Vehicle | T-1 | C-1 | T-2 | C-2 | T-3 | C-3 | T-4 | C-4 | T-5 | C-5 | Time: | T | C |
|---|---|---|---|---|---|---|---|---|---|---|---|---|---|---|
| NaCl Extract |||||||||||||||
| 23113 | NaCl | 0/0 | 0/0 | 0/0 | 0/0 | 0/0 | 0/0 | 0/0 | 0/0 | 0/0 | 0/0 | 24 hr. | 0/0 | 0/0 |
|  |  | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 | 0/0 |  | 0/0 | 0/0 |
| 23114 | NaCl | 0/0 | 0/0 | 0/0 | 0/0 | 0/0 | 0/0 | 0/0 | 0/0 | 0/0 | 0/0 | 24 hr. | 0/0 | 0/0 |
|  |  | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 | 0/0 |  | 0/0 | 0/0 |
| CSO Extract |||||||||||||||
| 23113 | CSO | 0/0 | 0/0 | 0/0 | 0/0 | 0/0 | 0/0 | 0/0 | 0/0 | 0/0 | 0/0 | 24 hr. | 0/0 | 0/0 |
|  |  | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 | 0/0 |  | 0/0 | 0/0 |
| 23114 | CSO | 0/0 | 0/0 | 0/0 | 0/0 | 0/0 | 0/0 | 0/0 | 0/0 | 0/0 | 0/0 | 24 hr. | 0/0 | 0/0 |
|  |  | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 | 0/0 |  | 0/0 | 0/0 |
| NaCl/EtOH Extract |||||||||||||||
| 23115 | NaCl | 0/0 | 0/0 | 0/0 | 0/0 | 0/0 | 0/0 | 0/0 | 0/0 | 0/0 | 0/0 | 24 hr. | 0/0 | 0/0 |
|  | EtOH | 0/0 | 0/0 | 0/0 | 0/0 | 0/0 | 0/0 | 0/0 | 0/0 | 0/0 | 0/0 | 48 hr. | 0/0 | 0/0 |

TABLE VI-continued

INTRACUTANEOUS TEST DRAIZE SCORES
Test Article: p-GlcNAc
(T = test, C = control)
Animal Species: Rabbit

| Animal ID # | Vehicle | T-1 | C-1 | T-2 | C-2 | T-3 | C-3 | T-4 | C-4 | T-5 | C-5 | Time: | Averages T | C |
|---|---|---|---|---|---|---|---|---|---|---|---|---|---|---|
| | | 0/0 | 0/0 | 0/0 | 0/0 | 0/0 | 0/0 | 0/0 | 0/0 | 0/0 | 0/0 | 72 hr. | 0/0 | 0/0 |
| | Total | 0/0 | 0/0 | 0/0 | 0/0 | 0/0 | 0/0 | 0/0 | 0/0 | 0/0 | 0/0 | | 0/0 | 0/0 |
| 23116 | NaCl | 0/0 | 0/0 | 0/0 | 0/0 | 0/0 | 0/0 | 0/0 | 0/0 | 0/0 | 0/0 | 24 hr. | 0/0 | 0/0 |
| | EtOH | 0/0 | 0/0 | 0/0 | 0/0 | 0/0 | 0/0 | 0/0 | 0/0 | 0/0 | 0/0 | 48 hr. | 0/0 | 0/0 |
| | | 0/0 | 0/0 | 0/0 | 0/0 | 0/0 | 0/0 | 0/0 | 0/0 | 0/0 | 0/0 | 72 hr. | 0/0 | 0/0 |
| | Total | 0/0 | 0/0 | 0/0 | 0/0 | 0/0 | 0/0 | 0/0 | 0/0 | 0/0 | 0/0 | | 0/0 | 0/0 |
| | | | | | | PEG Extract | | | | | | | | |
| 23115 | PEG | 0/0 | 0/0 | 0/0 | 0/0 | 0/0 | 0/0 | 0/0 | 0/0 | 0/0 | 0/0 | 24 hr. | 0/0 | 0/0 |
| | | 0/0 | 0/0 | 0/0 | 0/0 | 0/0 | 0/0 | 0/0 | 0/0 | 0/0 | 0/0 | 48 hr. | 0/0 | 0/0 |
| | | 0/0 | 0/0 | 0/0 | 0/0 | 0/0 | 0/0 | 0/0 | 0/0 | 0/0 | 0/0 | 72 hr. | 0/0 | 0/0 |
| | Total | 0/0 | 0/0 | 0/0 | 0/0 | 0/0 | 0/0 | 0/0 | 0/0 | 0/0 | 0/0 | | 0/0 | 0/0 |
| 23116 | PEG | 0/0 | 0/0 | 0/0 | 0/0 | 0/0 | 0/0 | 0/0 | 0/0 | 0/0 | 0/0 | 24 hr. | 0/0 | 0/0 |
| | | 0/0 | 0/0 | 0/0 | 0/0 | 0/0 | 0/0 | 0/0 | 0/0 | 0/0 | 0/0 | 48 hr. | 0/0 | 0/0 |
| | | 0/0 | 0/0 | 0/0 | 0/0 | 0/0 | 0/0 | 0/0 | 0/0 | 0/0 | 0/0 | 72 hr. | 0/0 | 0/0 |
| | Total | 0/0 | 0/0 | 0/0 | 0/0 | 0/0 | 0/0 | 0/0 | 0/0 | 0/0 | 0/0 | | 0/0 | 0/0 |

10.2.4. SYSTEMIC TEST

All of the mice treated with the p-GlcNAc extract or the control article increased in weight. See Table VII for data. In addition, there were no overt signs of toxicity observed in any p-GlcNAc or control animal. See Table VI for results. It is concluded, therefore, that none of the p-GlcNAc test animals showed a significantly greater biological reactivity than the animals treated with the control article.

TABLE VII

ANIMAL WEIGHTS AND CLINICAL OBSERVATIONS

| Group | Sex | Dose (ml) | Animal # | Body Weight (g) Day 0 | Day 3 | Weight Change | Signs of Toxicity* |
|---|---|---|---|---|---|---|---|
| NaCl:EtOH Test | Female | 1.03 | I. | 20.6 | 22.8 | 2.2 | None |
| 50 ml/kg | Female | 1.06 | II. | 21.1 | 23.4 | 2.3 | None |
| | Female | 1.02 | III. | 20.4 | 22.6 | 2.2 | None |
| | Female | 1.11 | IV. | 22.2 | 24.5 | 2.3 | None |
| | Female | 1.05 | V. | 21.0 | 23.2 | 2.2 | None |
| | | | Mean | 21.1 | 23.3 | | |
| | | | SD +/− | 0.7 | 0.7 | | |
| NaCl:EtOH Control | Female | 1.04 | VI. | 20.7 | 23.2 | 2.5 | None |
| 50 ml/kg | Female | 1.04 | VII. | 20.8 | 23.5 | 2.7 | None |
| | Female | 1.02 | VIII. | 20.3 | 22.3 | 2.0 | None |
| | Female | 0.91 | IX. | 18.2 | 20.6 | 2.4 | None |
| | Female | 0.94 | X. | 18.7 | 20.9 | 2.2 | None |
| | | | Mean | 19.7 | 22.1 | | |
| | | | SD +/− | 1.2 | 1.3 | | |
| PEG Test | Female | 1.02 | XI. | 20.3 | 22.7 | 2.4 | None |
| 10 ml/kg | Female | 0.96 | XII. | 19.2 | 21.4 | 2.2 | None |
| | Female | 0.95 | XIII. | 18.9 | 21.6 | 2.7 | None |
| | Female | 1.05 | XIV. | 20.9 | 22.7 | 1.8 | None |
| | Female | 0.94 | XV. | 18.7 | 21.2 | 2.5 | None |
| | | | Mean | 19.6 | 21.9 | | |
| | | | SD +/− | 1.0 | 0.7 | | |
| PEG Control | Female | 1.01 | XVI. | 20.1 | 22.3 | 2.2 | None |
| 10 g/kg | Female | 0.99 | XVII. | 19.8 | 22.0 | 2.2 | None |
| | Female | 1.10 | XVIII. | 22.0 | 24.3 | 2.3 | None |
| | Female | 1.07 | XIX | 21.4 | 23.6 | 2.2 | None |
| | Female | 1.03 | XX. | 20.6 | 22.4 | 1.8 | None |
| | | | Mean | 20.8 | 22.9 | | |
| | | | SD +/− | 0.9 | 1.0 | | |

*Summary of observations — 0, 4, 24, 48, and 72 h after injection

11. EXAMPLE: p-GlcNAc REFORMULATION

Figure 10A:
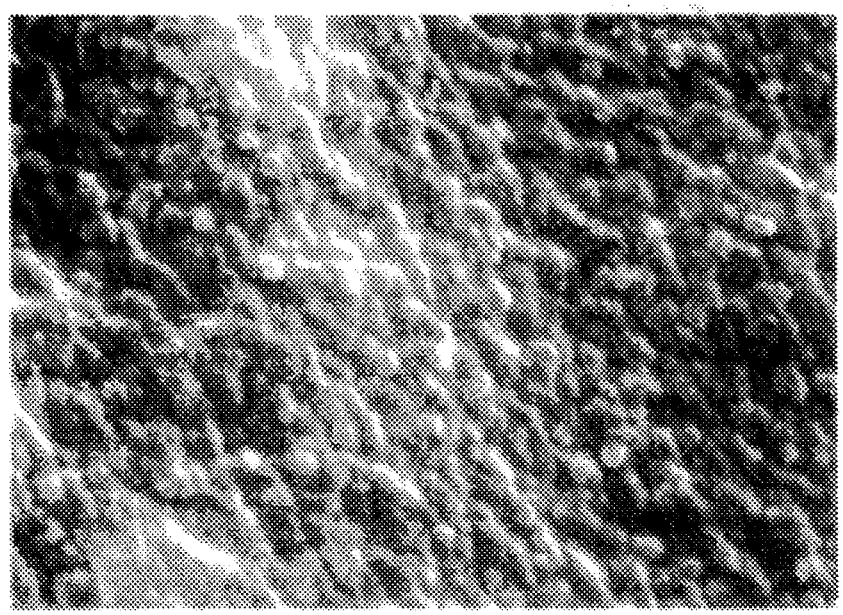
FIG. 10A–B. Scanning electron micrographs of a pure p-GlcNAc membrane made from material which was initially produced using the cell dissolution/neutralization purification method described in Section 5.3, below, dissolved in dimethylacetamide/lithium chloride, and reprecipitated in $H_2O$ into a-mat, as described below in Section 5.5. Magnification.
Figure 10B:
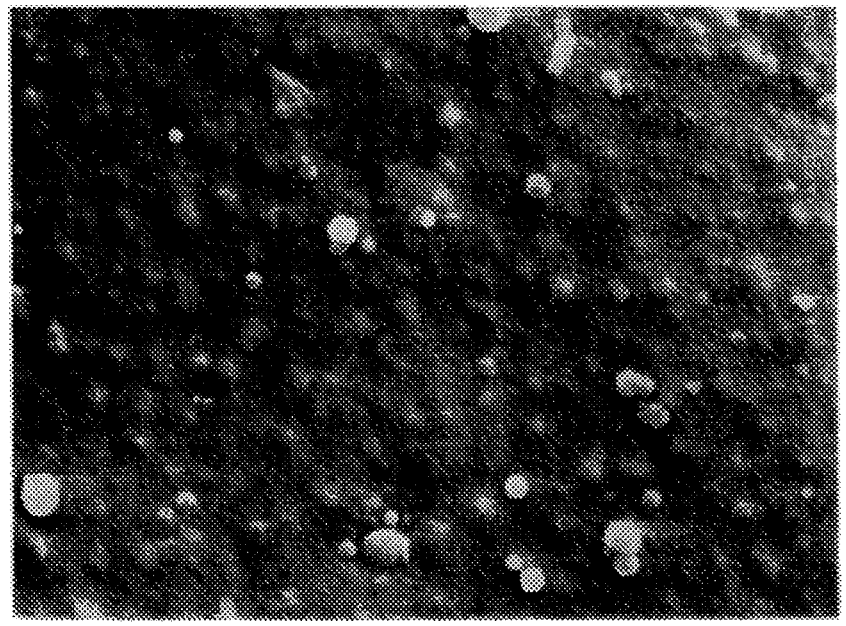

In the Working Example presented in this Section, a p-GlcNAc membrane (16.2 mg) was dissolved in 1 ml of a dimethylacetamide solution containing 5% LiCl. The p-GlcNAc-containing solution was placed in a syringe and extruded into 50 ml of pure water to precipitate a fiber. The resulting fiber was studied with scanning electron microscopy, as shown in FIG. 10A–B.

12. EXAMPLE: CELL ATTACHMENT TO p-GlcNAc

In this working example, it is demonstrated that p-GlcNAc represents an efficient substrate for cell attachment and growth in culture.

12.1. MATERIALS AND METHODS

Cells: The transformed mouse 3T3 fibroblast cell line was used, and was grown in DMEM supplemented with 10 fetal bovine serum (FBS).

p-GlcNAc membranes: p-GlcNAc was prepared according to the methods described, above, in Sections 5.3.1 and 8.

p-GlcNAc membranes were initially stuck to a #1 (18 mm) Corning cover glass using one drop of water, and were attached by autoclaving at 121° C. for 30 minutes. Membranes prepared in this manner were then placed in culture wells of 6 well culture plates.

Cell counts: Cell numbers were determined in media by direct counting with a hemocytometer, and on matrix by first rinsing membranes with fresh medium DMEM+10% FBS) followed by treatment with trypsin (10%, at 37° C. for 5 minutes) prior to counting.

SEM operating conditions: A Zeiss 962 instrument was utilized with an accelerating voltage of 10 kv, and a working distance of 15 mm. Polaroid type 55 p/n (u4) was utilized at various magnifications, as indicated. Sample coat:carbon coat (100 Å) & 100 Å aupd.

Specimen preparation: For primary fixation, the culture growth medium was replaced with 2% glutaraldehyde in Eagle's DMEM without serum. Several changes were performed to ensure a complete transition from growth media to fixative. Fixation proceeded for 0.5 hours at room temperature. Cover slips were transferred to fresh vials containing 2% Glutaraldehyde in 0.1 M Na Cacodylate at pH 7.2 with 0.1 M Sucrose and fixed for a further 1.5 hours at room temperature.

Dehydration, CPD, Mount and Sputter Coating:

Samples were rinsed in 0.1 M Na Cacodylate pH 7.2, and cover slips were transferred to a CPD holder. Dehydration was performed in ethanol series (30%, 50%, 75%, 85%, 95% and 3×100%, 5 mins each), and samples were critical point dried. Cover slips were then mounted on A1 stubs, carbon coated, using vacuum evaporator (@ 100 Å) and sputter coated with 100 Å AuPd.

Figure 14:
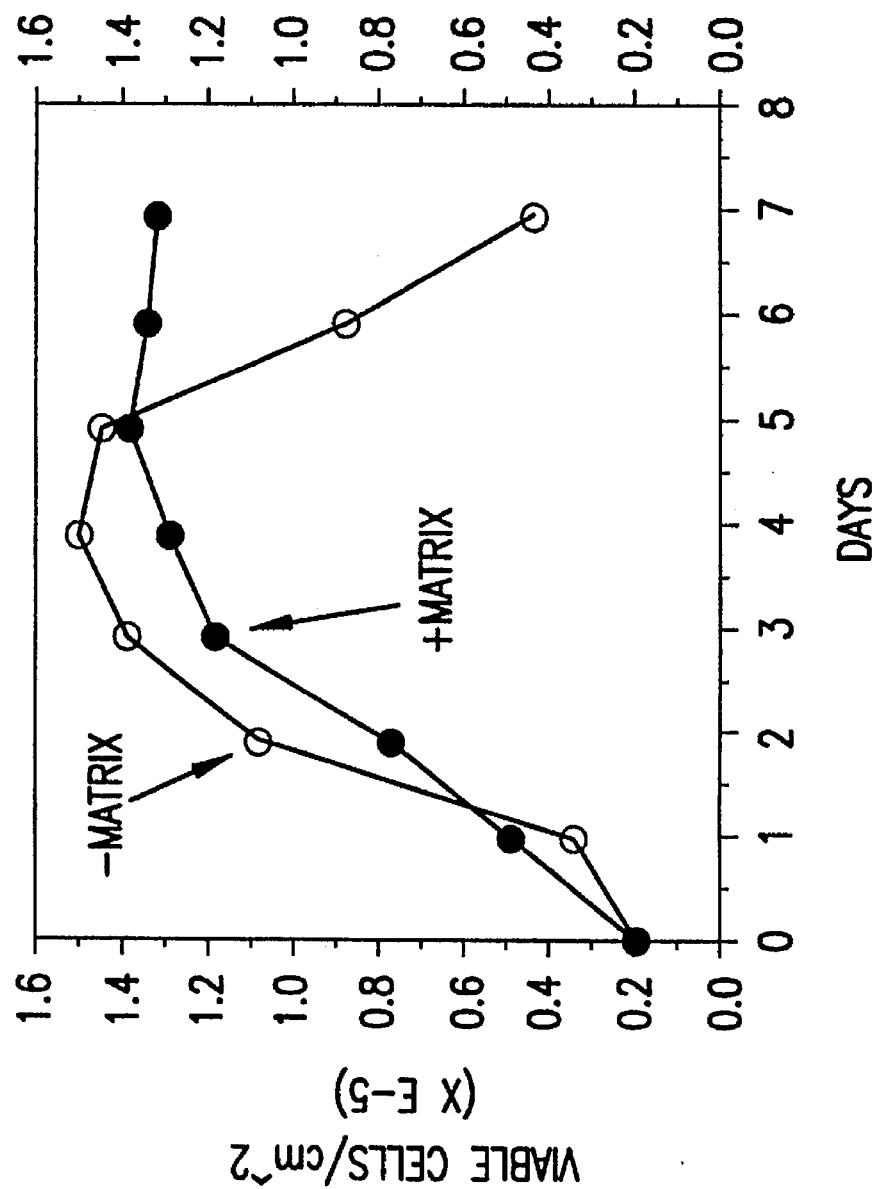
FIG. 14. Cell viability study of cells grown in the presence or absence of p-GlcNAc membranes. Closed circle (●): cells grown on p-GlcNAc matrix; open circles (○): cells grown in absence of matrix.

12.2. RESULTS p-GlcNAc membranes were tested for an ability to form a substrate on which cells may be grown in culture. Mouse fibroblast cells were grown in wells in the presence or absence of p-GlcNAc membranes and cell counts were taken daily to assay the viability of cultures. The results of one such series of cell counts is shown in FIG. 14. As indicated, by day 5 after plating, only the wells containing p-GlcNAc membranes were able to continue to sustain viable cells, demonstrating that p-GlcNAc membranes are capable of acting as efficient substrates for the continued growth of cells in culture.

Figure 15A:
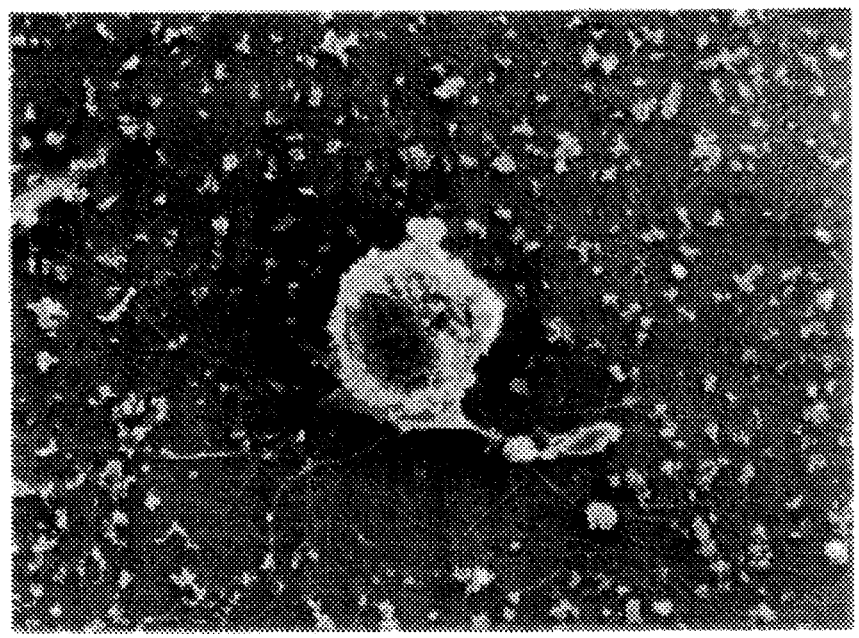
(FIG. 15A), 1000x.
Figure 15B:
(FIG. 15B), 3000x.

Further, the SEM micrographs depicted in FIG. 15A–B show healthy cells strongly attached to p-GlcNAc membranes.

13. EXAMPLE: p-GlcNAc/COLLAGEN HYBRIDS

Presented in this Working Example is the formation and characterization of a p-GlcNAc/collagen hybrid material.

13.1. MATERIALS AND METHODS

Materials: Bovine Type I collagen was used in preparation of the hybrids described in this study. p-GlcNAc was prepared according to the mechanical force method described, above, in Section 5.3.2.

Hybrid preparation: Collagen (10 milligrams/ml) and p-GlcNAc (0.25 milligrams/ml) aqueous suspensions were mixed, in different ratios, frozen in liquid $N_2$ (−80° C.), held at −9° C. for 4 hours, and lyophilized. Material was dehydrothermally cross-linked under vacuum (approximately 0.030 Torr) at 60° C. for 3 days.

Cell Culture: Mouse 3T3 fibroblast cells were grown on the collagen/p-GlcNAc hybrids produced. Standard culturing procedures were followed, and SEM micrographs were taken after 8 days in culture.

13.2. RESULTS

Figure 16A:
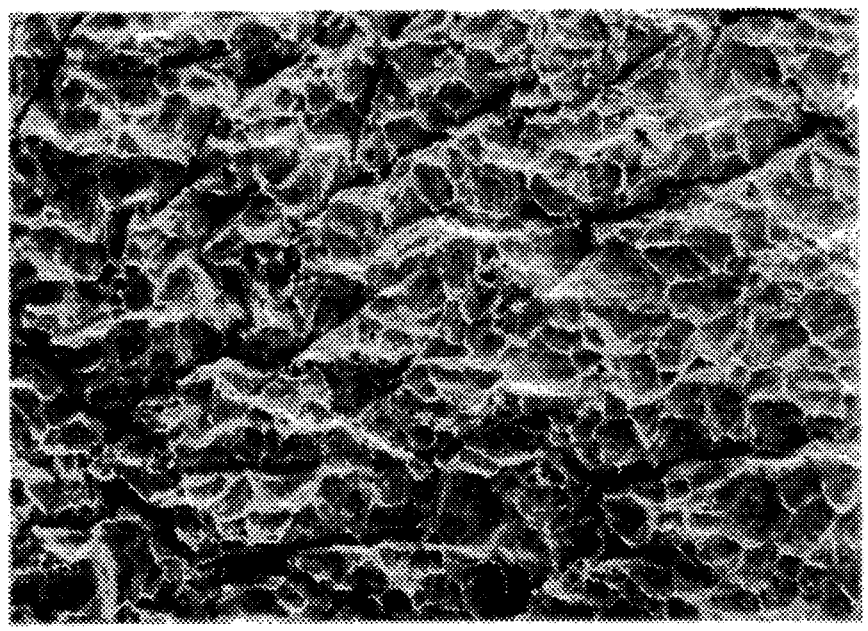
FIG. 16A. Scanning electron micrograph (SEM) of a collagen-only control material prepared according to the method described, below, in Section 13.1. Magnification 100x.
Figure 16B:
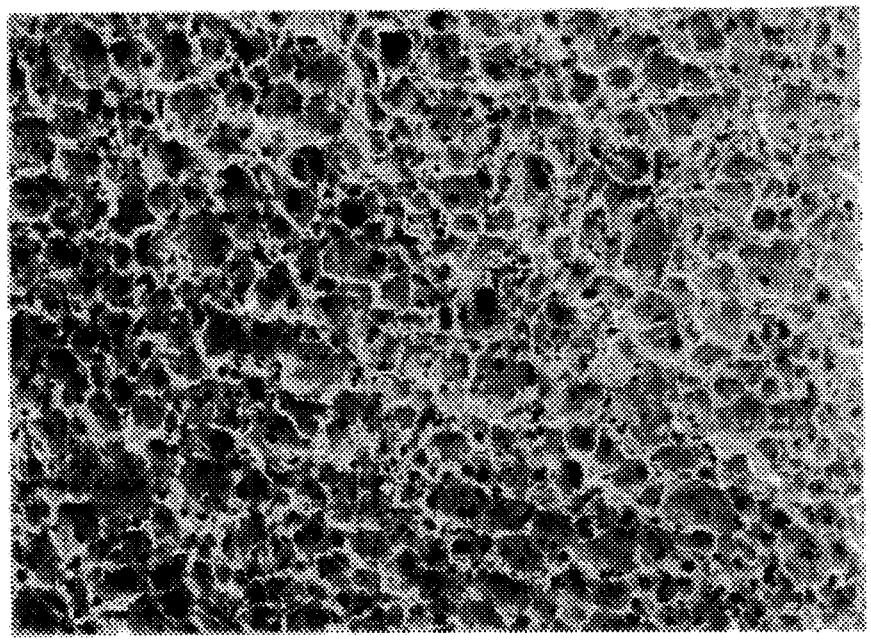
FIG. 16B. Scanning electron micrograph (SEM) of a collagen/p-GlcNAc hybrid material prepared according to the method described, below, in Section 13.1. Ratio collagen suspension:p-GlcNAc suspension equals 3:1, with final concentrations of 7.5 mg/ml collagen and 0.07 mg/ml p-GlcNAc. Magnification 100x.
Figure 16C:
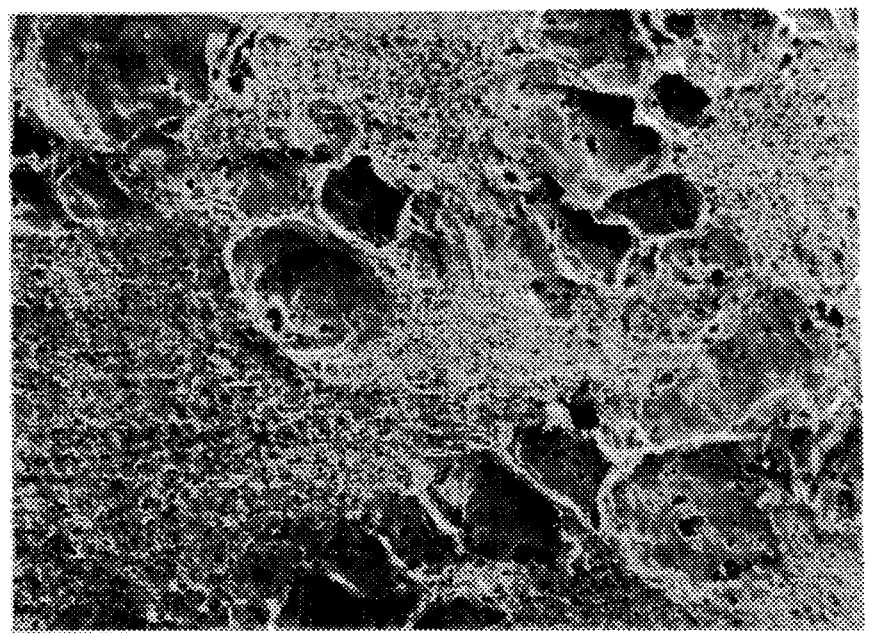
FIG. 16C. Scanning electron micrograph (SEM) of a collagen/p-GlcNAc hybrid material prepared according to the method described, below, in Section 13.1. Ratio collagen suspension:p-GlcNAc suspension equals 1:1, with final concentrations of 5.0 mg/ml collagen and 0.12 mg/ml p-GlcNAc. Magnification 100x.
Figure 16D:
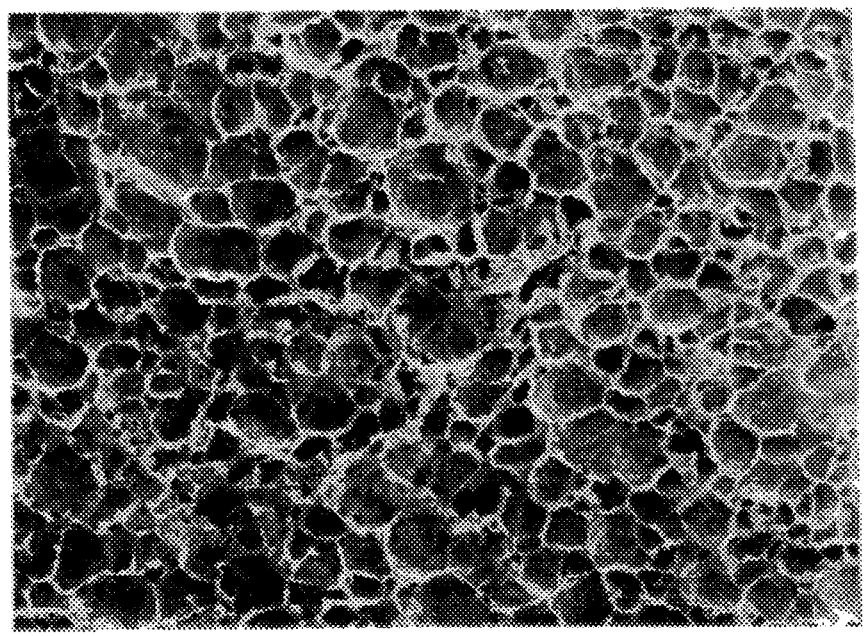
FIG. 16D. Scanning electron micrograph (SEM) of a collagen/p-GlcNAc hybrid material prepared according to the method described, below, in Section 13.1. Ratio collagen suspension:p-GlcNAc suspension equals 2:2, with final concentrations of 10.0 mg/ml collagen and 0.25 mg/ml p-GlcNAc. Magnification 100x.
Figure 16E:
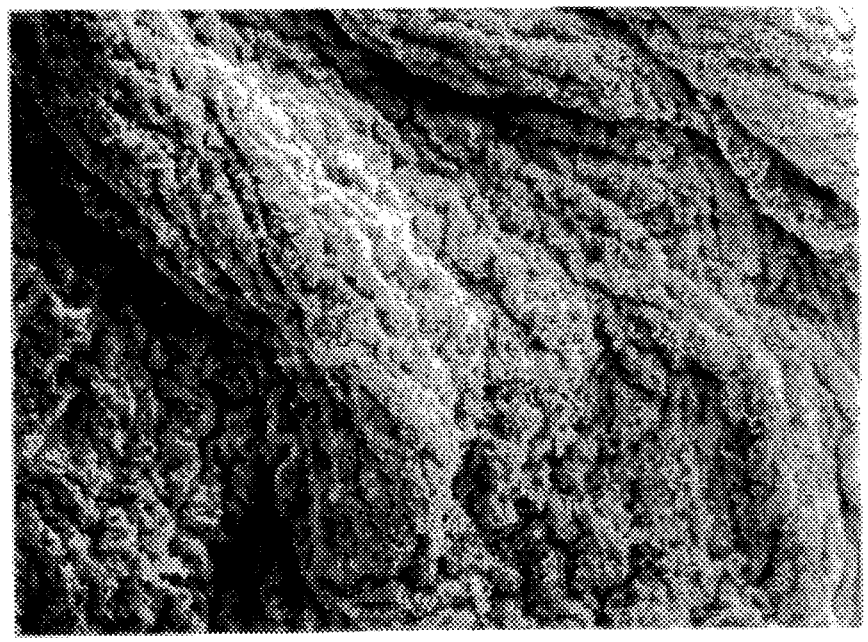
FIG. 16E. Scanning electron micrograph (SEM) of a collagen/p-GlcNAc hybrid material prepared according to the method described, below, in Section 13.1. Ratio collagen suspension:p-GlcNAc suspension equals 1:3, with final concentrations of 2.5 mg/ml collagen and 0.25 mg/ml p-GlcNAc. Magnification 100x.
Figure 17A:
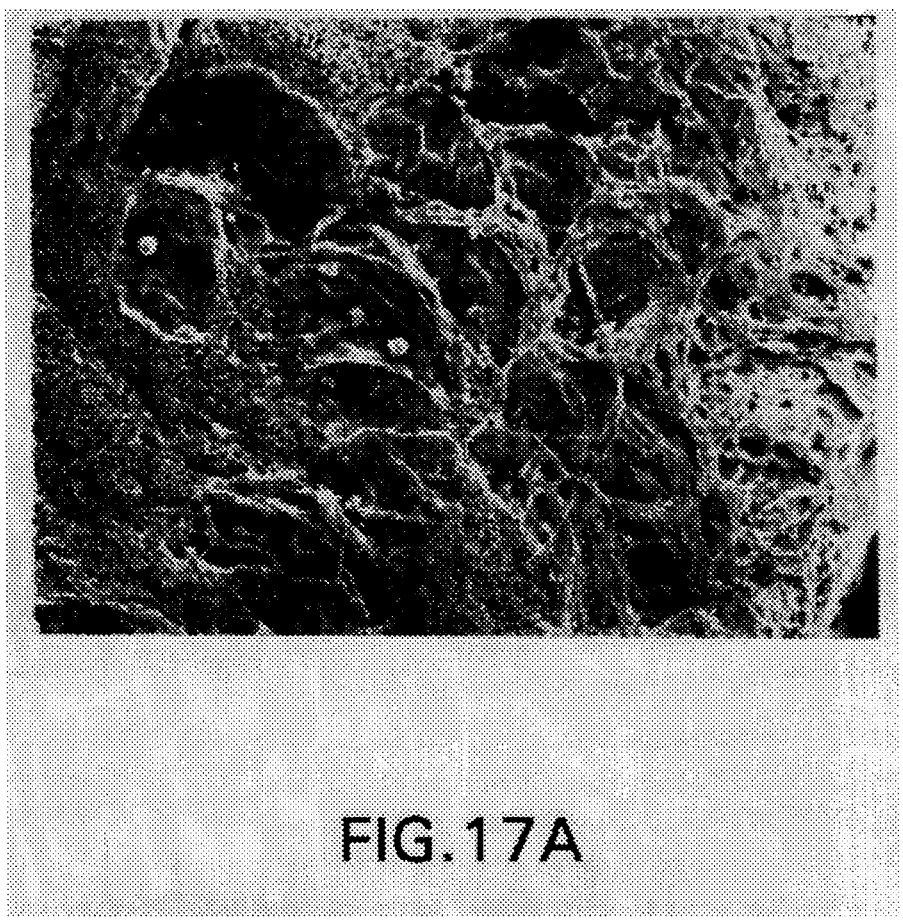
FIG. 17A. SEM of mouse 3T3 fibroblast cells cultured on the collagen-only control material of FIG. 16A, above. Magnification 100x.
Figure 17B:
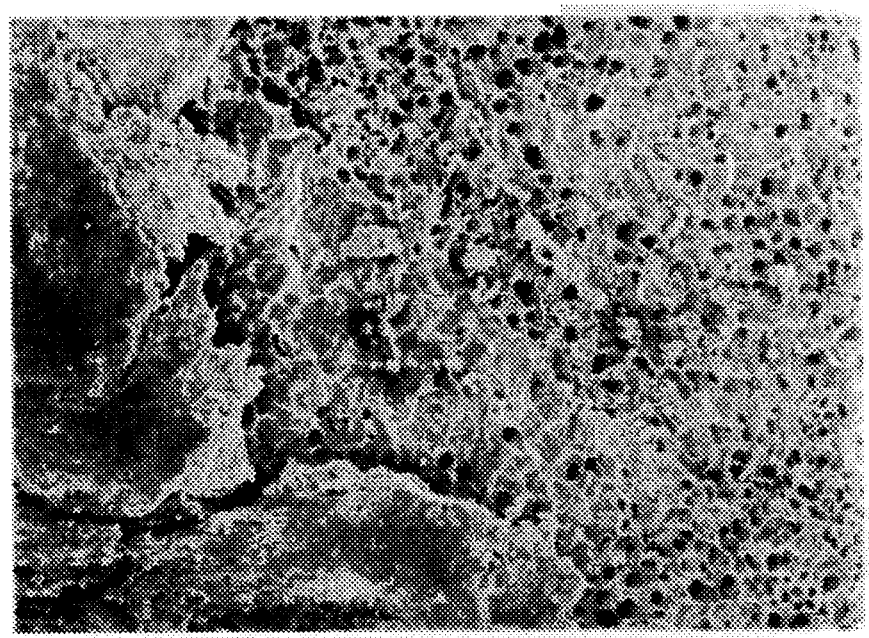
FIG. 17B. SEM of mouse 3T3 fibroblast cells cultured on the collagen/p-GlcNAc material of FIG. 16B, above. Magnification 100x.
Figure 17C:
FIG. 17C. SEM of mouse 3T3 fibroblast cells cultured on the collagen/p-GlcNAc material of FIG. 16C, above. Magnification 100x.
Figure 17D:
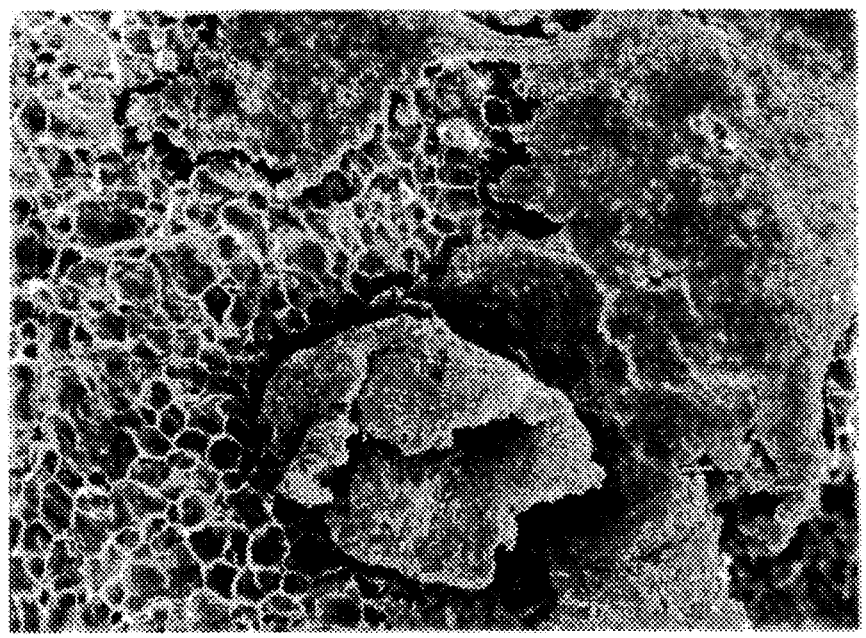
FIG. 17D. SEM of mouse 3T3 fibroblast cells cultured on the collagen/p-GlcNAc material of FIG. 16D, above. Magnification 100x.

Collagen and p-GlcNAc aqueous suspensions were mixed in differing ratios (namely, 3:1, 1:1, 2:2, and 1:3 collagen:p-GlcNAc suspension ratios), frozen, lyophilized, and crosslinked. Such a procedure yielded collagen/p-GlcNAc slabs. SEM micrographs of the resulting materials are shown in FIGS. 16 B–E. FIG. 16A represents a collagen-only control material. Note the porous structure of the hybrid material.

The collagen/p-GlcNAc hybrids of the invention provide an efficient three-dimensional structure for the attachment and growth of cells, as shown in the SEM micrographs in FIGS. 17A–D.

14. EXAMPLE: NMR CHARACTERIZATION OF PURE PREPARATIONS OF p-GlcNAc

Presented in this Example is an NMR (nuclear magnetic resonance) analysis of a pure p-GlcNAc preparation.

14.1. MATERIALS AND METHODS p-GlcNAc preparations: The p-GlcNAc used in the NMR studies described here was prepared using the chemical purification method described, above, in Section 5.3.2, with hydrofluoric acid utilized as the chemical reagent.

NMR techniques: Solid state NMR data was obtained using a Bruker 500 MH NMR spectrometer. Computer image analysis was used to transform the raw NMR spectrum data so as to eliminate background and to normalize baselines. An example of such transformed data are shown in FIG. 18. Transformed NMR curves such as that in FIG. 18 were used to obtain areas for every carbon atom type, and then to calculate the ratios of CH3(area) to C-atom(area). Such values, obtained as described, are provided in FIG. 20.

14.2. RESULTS

Figure 19:
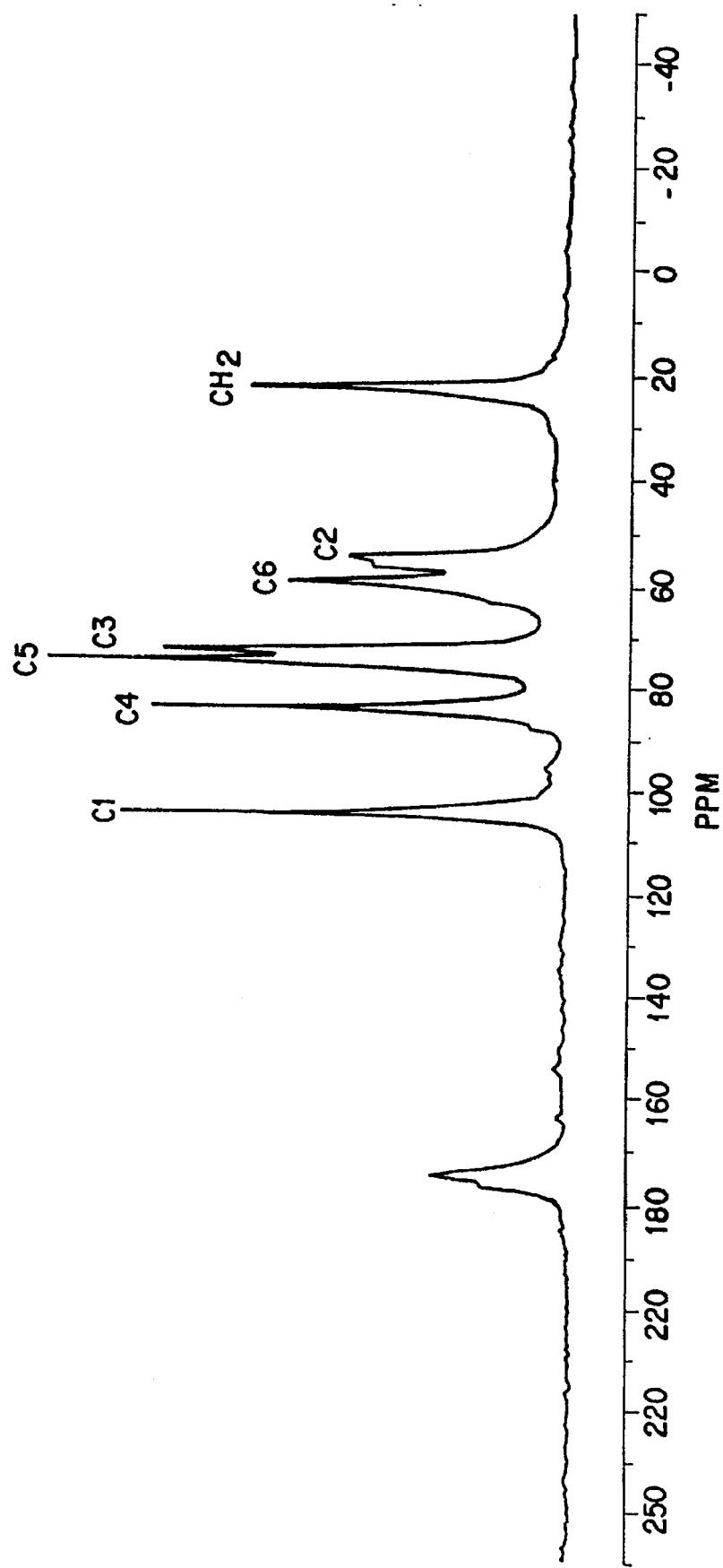
FIG. 19. Typical p-GlcNAc $C^{13}$-NMR spectrum. The individual peaks represent the contribution to the spectrum of each unique carbon atom in the molecule.

Solid state NMR data was obtained by measuring the $C^{13}$-NMR spectrum of a 500 mg sample of p-GlcNAc. A typical NMR spectrum is shown in FIG. 19. The individual peaks represent the contribution to the spectrum of each unique carbon atom in the molecule. The relative percentage of each type of carbon atom in the molecule was determined dividing the area of the peak generated by that carbon species by the total sum of the areas under all of the NMR peaks obtained in the spectrum. Thus, it was possible to calculate the ratio of each of the atoms of the molecule measured by a reference atom. All p-GlcNAc molecules consist of N-acetylated glucosamine residues having C1, C2, C3, C4, C5 and C6 atoms, by definition. The ratio, then, of the area of the N-acetyl CH3 carbon atom peak to the areas of any of the glucosamine residue carbon atom peaks, above, should be 1.0 if all of the glucosamine residues in the polymer are N-acetylated. Data such as those in FIG. 20 were used to obtain values for the CH3(area) ratios.

Figure 20:
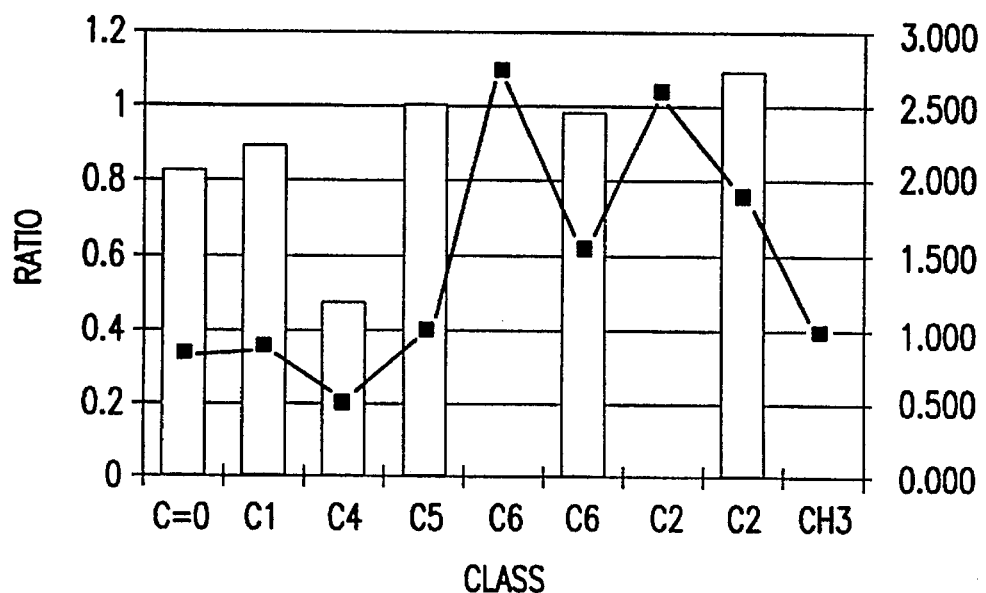
FIG. 20. Transformed NMR spectrum data representing values calculated for CH3(area) to C-atom(area) ratios. Top: Graphic depiction of data; bottom: numerical depiction of data.
Figure 21B:
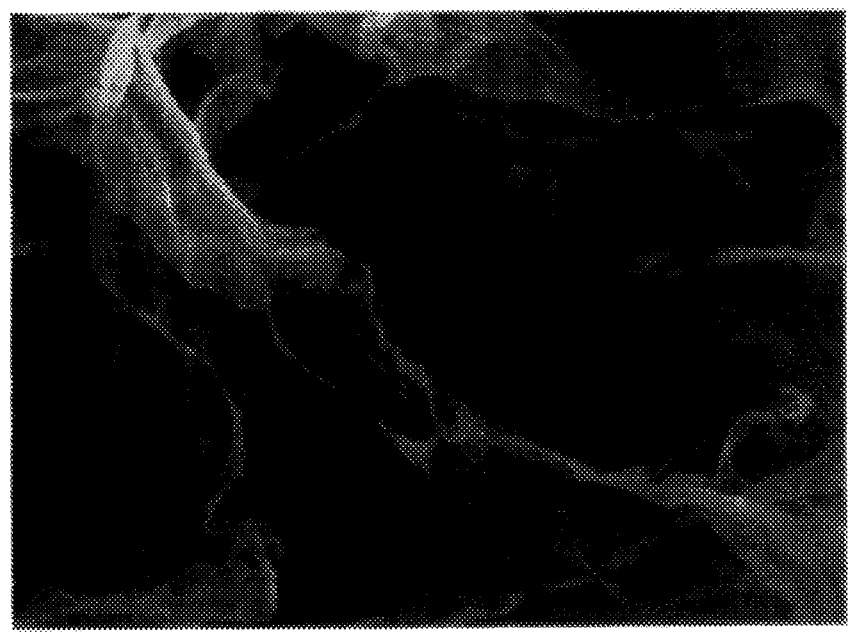
Figure 21B:
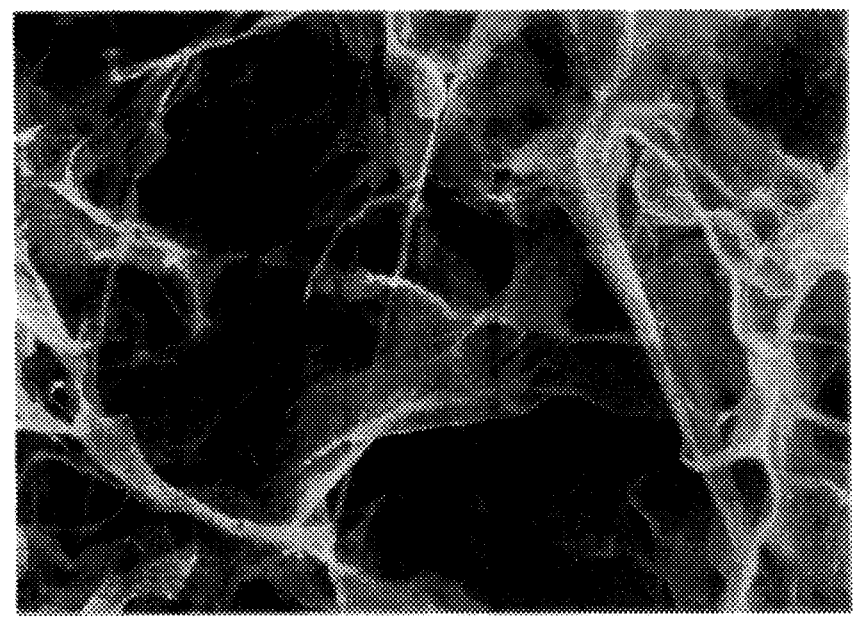
Figure 21C:
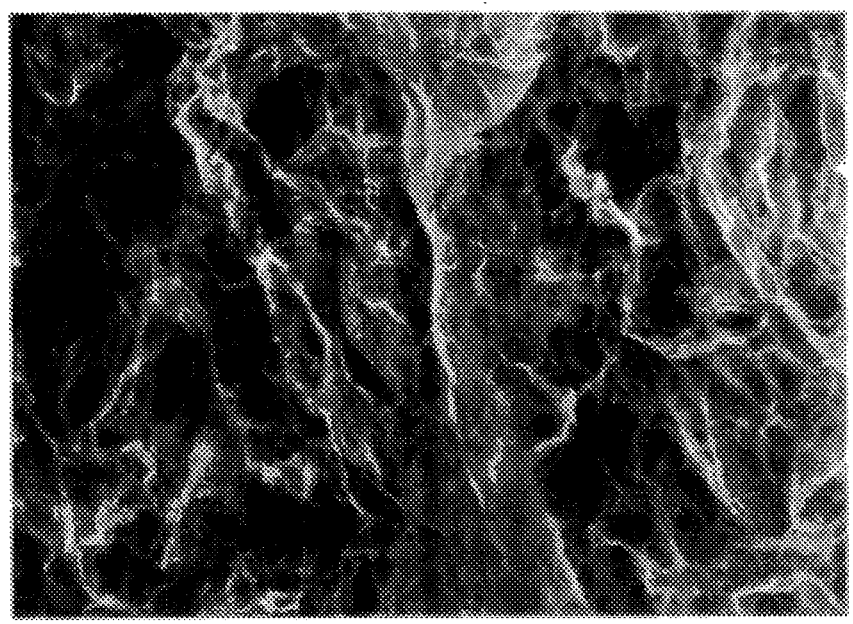
Figure 21D:
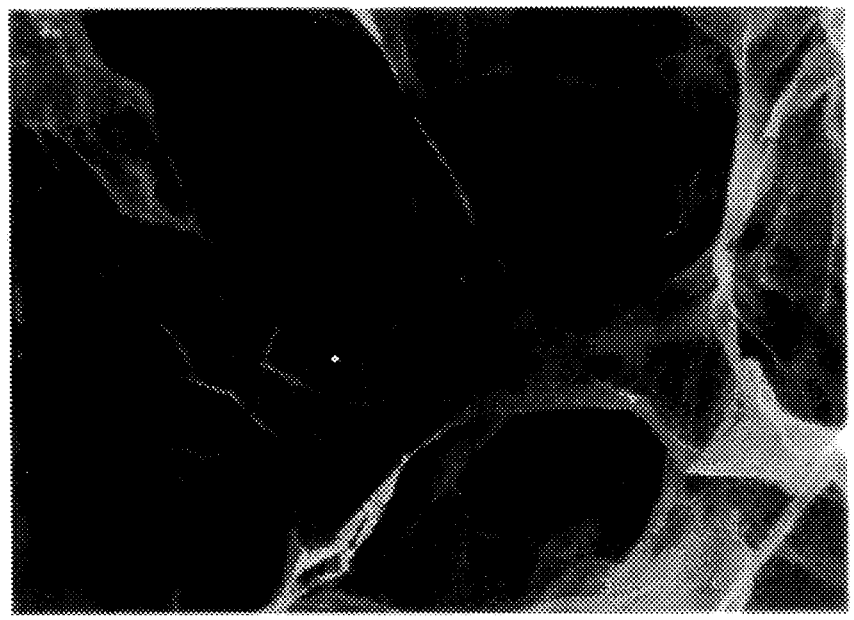
Figure 21E:
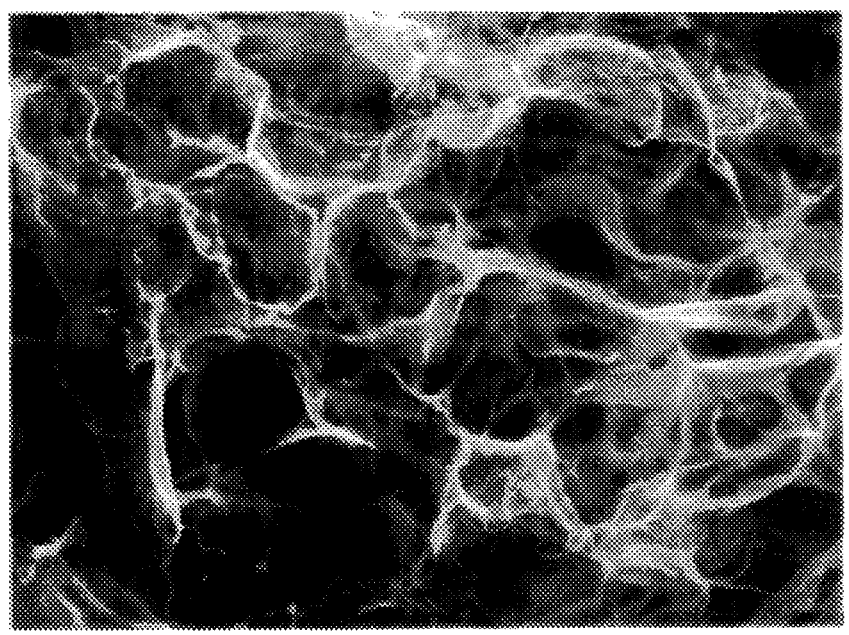
Figure 21F:
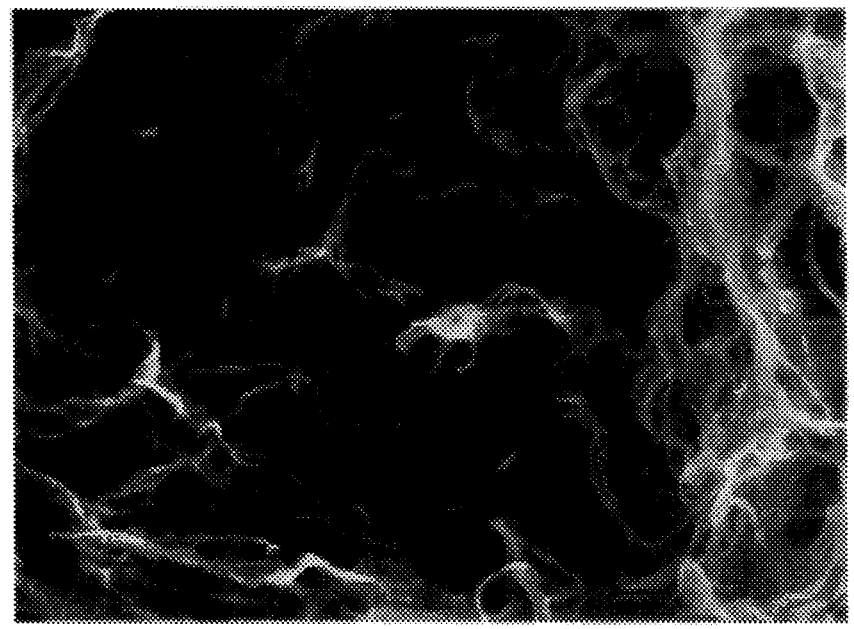
Figure 21G:
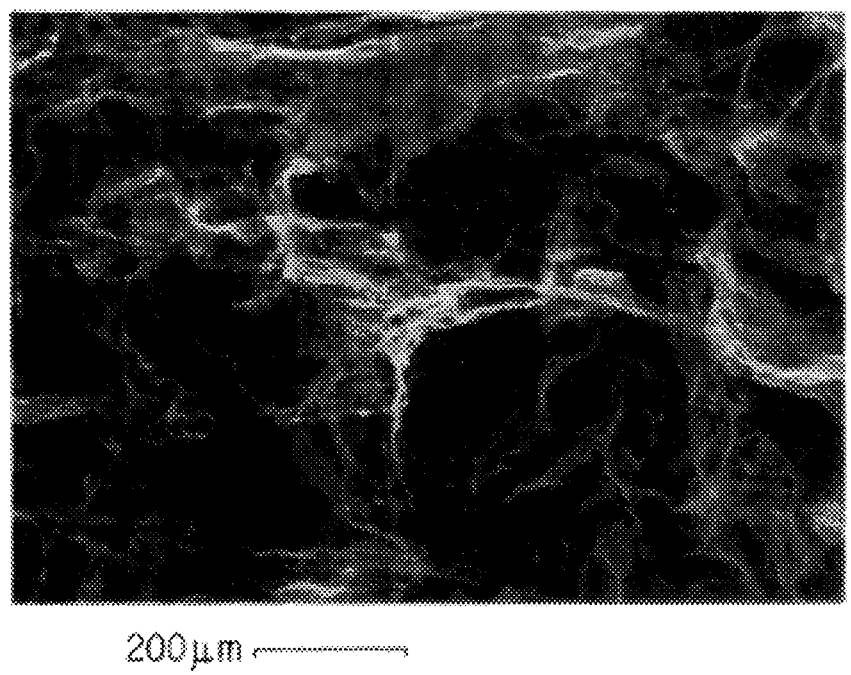
Figure 22A:
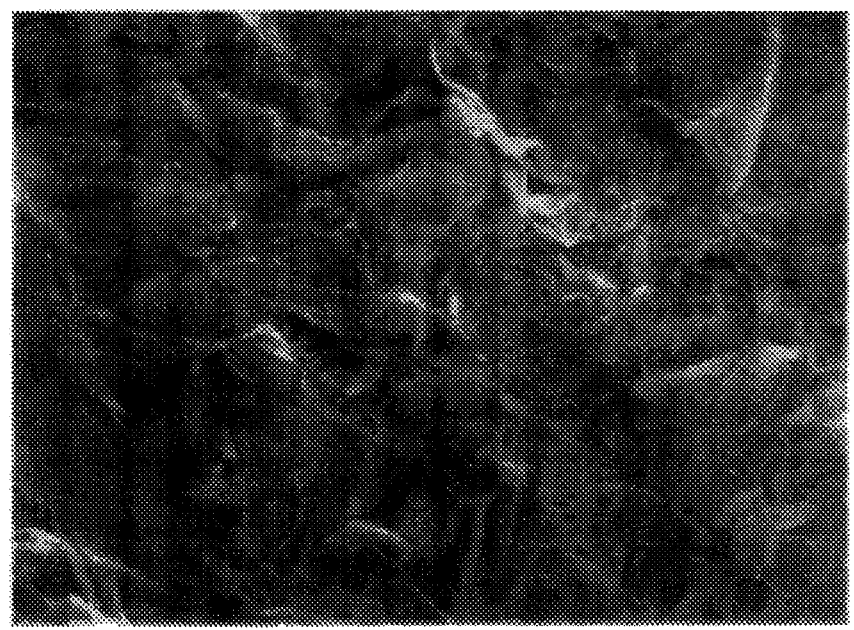
FIG. 22A–G. Fibroblast cells grown on three-dimensional p-GlcNAc matrices prepared by lyophilizing p-GlcNAc in distilled water. Magnification: 100x (FIGS. 22A, 22E), 500x (FIG. 22B), 1000x (FIGS. 22C, 22F), 5000x (FIGS. 22D, 22G). Scales marking 5, 20, 50, or 200 microns, as indicated, are included in each of the figures.
Figure 22B:
Figure 22C:
Figure 22D:
Figure 22E:
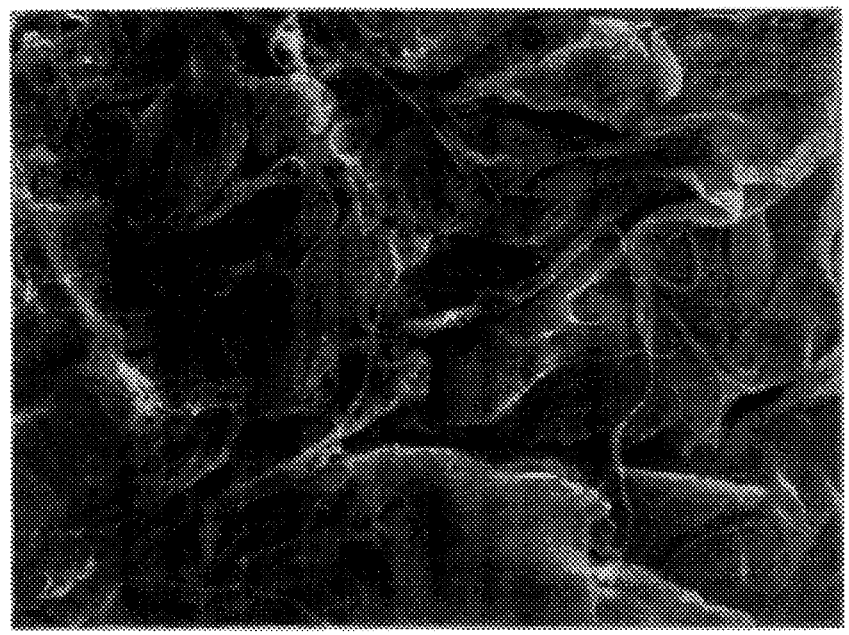
Figure 22F:
Figure 22G:
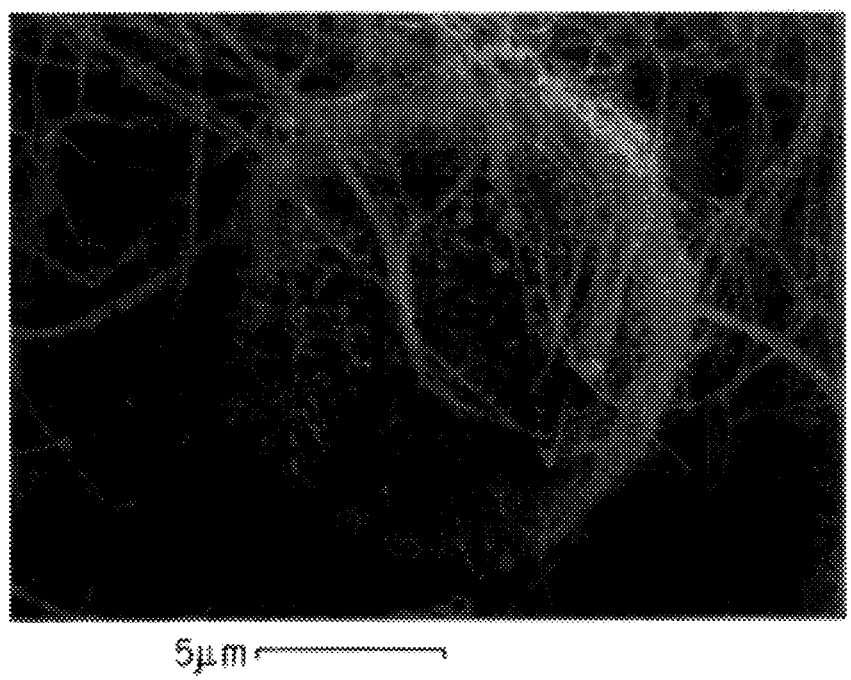

The calculated ratios in FIG. 20 are in many cases equal to or nearly equal to 1.0, within experimental error, e.g. CH3/C2=1.097, CH3/C6=0.984, CH3/C5=1.007, CH3/C1=0.886. These results are consistent with the conclusion that the p-GlcNAc material of the invention is free of contaminants and is fully acetylated (i.e. that essentially 100% of the glucosamine residues are N-acetylated).

15. EXAMPLE: SYNTHESIS AND BIOLOGICAL CHARACTERIZATION OF CONTROLLED PORE SIZE THREE-DIMENSIONAL p-GlcNAc MATRICES

Described below, are methods for the production of three-dimensional p-GlcNAc based porous matrices having controlled average pore sizes. Such matrices have a variety of important applications, particularly, for example, as means for the encapsulation of cells. Such cell encapsulation compositions are useful as transplantable cell-based therapeutics, and in other cell & tissue engineering applications such as in cartilage regeneration. The capability to manipulate the morphology and dimensionality of p-GlcNAc materials, as demonstrated here, provides a powerful tool in expanding the potential applications of the p-GlcNAc material of the invention.

15.1. MATERIALS AND METHODS p-GlcNAc starting material: p-GlcNAc was prepared using the chemical purification method described, above, in Section 5.3.2, with hydrofluoric acid utilized as the chemical reagent.

Matrix formation: Suspensions (5 mls) containing 20 mg p-GlcNAc samples were made in the solvents listed below in Section 15.2, prior to lyophilization. Samples were then poured into wells of tissue culture dishes and frozen at $-20°$ C. The frozen samples were then lyophilized to dryness, and the resulting three-dimensional matrices were removed.

Scanning electron microscopy techniques: The procedures utilized here were performed as described, above, in Section 12.1. The images shown in FIGS. 21A–G. are 200× magnifications of the matrix material, and a scale marking of 200 microns is indicated on each of these figures.

15.2. RESULTS p-GlcNAc suspensions were obtained with each of the following solvents, as described, above, in Section 15.1:
A. Distilled water
B. 10% methanol in distilled water
C. 25% methanol in distilled water
D. Distilled water only
E. 10% ethanol in distilled water
F. 25% ethanol in distilled water
G. 40% ethanol in distilled water Samples of matrix formed using each of the solvents were subjected to scanning electron microscopic (SEM) analysis, as shown in FIGS. 21A–G. These figures reveal that the average matrix pore size decreases as the percentage of either methanol or ethanol increases in each suspension.

Specifically, pore diameter in the two water suspensions (FIGS. 21A and 21D) approach 200 microns on average. Pore size in the samples depicted in FIGS. 21C and 21F (25% methanol and ethanol, respectively) are between 30 and 50 microns on average.

The results shown here suggest that while both ethanol and methanol may be successfully used to control p-GlcNAc pore size, ethanol may be more efficient than methanol.

16. EXAMPLE: CELL GROWTH ON THREE-DIMENSIONAL POROUS p-GlcNAc MATRICES

Described in this Section are results demonstrating the successful use of three-dimensional p-GlcNAc porous matrices as substrates for the culturing of cells.

16.1. MATERIALS AND METHODS p-GlcNAc starting material: p-GlcNAc was prepared using the chemical purification method described, above, in Section 5.3.2, with hydrofluoric acid utilized as the chemical reagent.

Matrix formation: Three-dimensional p-GlcNAc matrices were prepared by the lyophilization of suspensions of p-GlcNAc in water, water-ethanol, or water-methanol mixtures.

Suspensions (5 mls) containing 20 mgs p-GlcNAc were prepared in the following solvents prior to lyophilization:
1. Distilled water only
2. 10% methanol in distilled water
3. 25% methanol in distilled water
4. Distilled water only
5. 10% ethanol in distilled water
6. 25% ethanol in distilled water
7. 40% ethanol in distilled water Samples were poured into circular wells of plastic tissue culture dishes and were frozen at $-20°$ C. The frozen samples were then lyophilized to dryness, and the resulting three-dimensional matrices were removed. Samples of each matrix were subjected to scanning electron microscopic (SEM) analysis.

Cells: Mouse embryo BALBC/3T3 fibroblast cell line (clone A31), obtained from the ATCC, were used for culturing on the three-dimensional porous p-GlcNAc matrices.

Culturing conditions: One $cm^2$ samples of porous matrices were placed in tissue culture wells and were covered with a standard tissue-culture growth medium. Each well was seeded and cells were cultured for 6 days at $37°$ C. in a $CO_2$ incubator (5% $CO_2$).

SEM procedures: Matrix samples were fixed and subjected to SEM analysis as described, above, in Section 12.1. The matrices were prepared by lyophilizing p-GlcNAc in distilled water. Images vary in magnification from 100× to 5000×, as indicated in figure legends (FIGS. 22A–G).

16.2. RESULTS

SEM photographs of p-GlcNAc matrices containing attached mouse fibroblast cells attached are shown in FIGS.

22A–G. These photographs show that the three-dimensional p-GlcNAc matrices contain attached mouse fibroblast cells. Further, the photographs reveal that there is a close interaction and connection between the cells and the p-GlcNAc matrix material. It is also notable that the cells have a rounded three-dimensional morphology which is different from the flat, spread shape of the cells when cultured directly onto plastic culture dishes. Cell viabilities were determined to be greater than 95%.

17. EXAMPLE: p-GlcNAc SUCCESSFULLY REDUCES AND PREVENTS POST-SURGICAL ADHESIONS

The Example presented herein demonstrates the successful use of p-GlcNAc materials, specifically a p-GlcNAc membrane and gel formulation, to reduce or prevent the formation of post-surgical adhesions in a series of animal models for such adhesions.

17.1. MATERIALS AND METHODS

Synthesis p-GlcNAc-lactate: p-GlcNAc membrane starting material was produced by the chemical method, as described, above, in Section 5.3.2, with hydrofluoric acid utilized as the chemical reagent.

The p-GlcNAc was converted to deacetylated p-GlcNAc by the following method. (It should be noted that approximately 1.4 g of p-GlcNAc are needed to produce 1 g of p-GlcNAc lactate, given the expected loss in mass of approximately 15% which occurs upon deacetylation). In a stoppered flask approximately 200 mg of p-GlcNAc membrane material were mixed vigorously with approximately 200 ml 60% NaOH. The vigorous shaking served to separate the p-GlcNAc membrane material to the greatest extent possible. The NaOH solution used was made at least 12 hours before use. The reaction flasks were placed in an 80° C. water bath for 6 hrs, with periodic shaking to separate and wet the p-GlcNAc material. After 6 hrs, the samples were taken from the water bath and the NaOH solution was immediately decanted. The membrane materials were washed with ddH$_2$O, at room temperature, until a pH of 7 was reached. The membranes were removed from the water and dried on a Teflon sheet.

At this point a 2 mg sample was collected for C, H, N analysis in order to determine the extent of deacetylation. Further, solubility of the deacetylated material in 1% acetic acid was checked, with a solubility of 1 mg/ml indicating that the p-GlcNAc material was appropriately deacetylated.

The partially deacetylated pGlcNAc was then converted to pGlcNAc-lactate using the following method: Sufficient 2-propanol (containing 10% water) to wet all of the partially deacetylated pGlcNAc material and to allow for stirring was added to 1 g of the partially deacetylated p-GlcNAc in a 250 ml Erlenmeyer flask. (Approximately 30 mls 2-propanol are required.) 2-propanol must be reagent grade, and fresh prior 0 to each synthesis. With stirring, 1.1 mL of a 50% aqueous lactic acid solution is added. Lactic acid should be reagent grade, and must be analyzed to determine the exact concentration of available (i.e., non-esterified) lactic acid present. This was generally accomplished by titration with 0.1N NaOH to the phenolphthalein end-point (pH 7.0). The concentration of lactic acid used must be constant, i.e., must be +/−1 percent, for each p-GlcNAc synthesis. The mixture was allowed to stir for at least two hours at room temperature. It is possible to add low heat in order to increase the reaction rate. Reaction time may be extended, or the amount of 50% aqueous lactic acid may be increased to ensure that the reaction goes to completion. The contents of the flasks were finely filtered through a Buchner funnel using quantitative ashless filter paper. The material was washed with 15 ml of anhydrous 2-propanol. The material was allowed to air dry in a fume hood for 2 hours and then placed in an oven at 40° C. overnight. For every gram of partially deacetylated p-GlcNAc starting material, a final p-GlcNAc-lactate weight of approximately 1.4 g, (i.e., an increase of 40% in mass) should be obtained.

Formulation of p-GlcNAc-lactate as a gel: The p-GlcNAc-lactate material was formulated into a gel as follows: p-GlcNAc-lactate material was dissolved in distilled and deionized water to a concentration of between 0.1–4.0% p-GlcNAc-lactate, by weight. Reagent grade propylene glycol (2-propanediol) was then added to a final propylene glycol concentration of between 1–10%. In some cases, a preservative was added to prevent bacterial and/or fungal contamination of the product. Typically, concentrations of p-GlcNAc-lactate of between 0.1%–4.0% were prepared. The viscosity of these preparations increases dramatically as the p-GlcNAc-lactate percentage increases, such that formulations having 0.5% or more of the p-GlcNAc-lactate behave as gels.

Animal models:

Sprague-Dawley rats: Adhesions are produced in this model by abrading or irritating the serosal surface of the cecum and apposing it to an area of parietal peritoneum. The success rate for inducing adhesions in control animals with this method is reported to be at an average 80%.

Specifically, the surgical procedure for inducing post-surgical adhesions in these rats involved the following. Animals were placed in dorsal recumbency and prepared and draped accordingly for aseptic surgery. Abdominal cavities were exposed through a midline incision. An area, approximately 0.5 cm ×1.0 cm, of parietal peritoneum on the left abdominal wall was carefully excised, removing a thin layer of muscle, along with the peritoneum.

The cecum was then elevated and isolated. An area, approximately 0.5 cm ×1.0 cm, on the lateral surface of the proximal end of the cecum was abraded by rubbing ten times with a dry gauze. The cecum was then scraped with a scalpel blade to cause minute petechial hemorrhages. The cecal abrasion and the peritoneal incision were left exposed for 15 minutes.

After 15 minutes, the test article (i.e., the p-GlcNAc material) or control article was applied to the cecal wound. The cecal abrasion and the peritoneal wound were then apposed and held in contact with Allis tissue forceps for an additional 15 minutes.

The cecum was then replaced into the abdomen such that the abraded area of the cecum was adjacent to the peritoneal site. The abdominal incision was closed and the animal was allowed to recover from the anesthesia.

Fourteen days after surgery, animals were euthanized and the abraded area was examined for the formation of post-surgical adhesions. If adhesions were present, the entire area involved in the adhesion (i.e., body wall, test or control article, and internal organs) were dissected free of the animal.

The extent of involvement and tenacity of adhesions were evaluated according to the following scales:

| Extent of involvement scores: | |
|---|---|
| 0 | no adhesion |
| 1 | adhesion <= 25% of the area |
| 2 | adhesion <= 50% of the area |
| 3 | adhesion <= 75% of the area |
| 4 | adhesion > 75% of the area |
| | Tenacity Scores: |
| 0 | no adhesion |
| 1 | adhesion freed with blunt dissection |
| 2 | adhesion freed with aggressive dissection |
| 3 | adhesion requiring sharp dissection |

Additional animal models: Pig and horse large animal bowel models were used to assess the prevention of peritoneal adhesions.

Surgical procedure: The animals were placed in dorsal recumbency and prepared and draped accordingly for aseptic surgery. The abdominal cavity was exposed through a midline incision. The small intestine was elevated and a 2 cm ×2 cm section was identified, extensively abraded (approximately 200 strokes using a scalpel), and allowed to dry for 10 minutes. The test article (i.e., p-GlcNAc material) or control article was then applied to the abraded wound, and the wounded section of the small intestine was replaced into the abdomen. In such a large bowel type of animal model, six wounds, each separated by 4 inches of bowel from the adjacent wound provides an environment highly prone to form adhesions. Following induction of the last of the wounds, the abdominal incision is closed and the animal is allowed to recover from the anesthesia.

Analysis of peritoneal adhesions: Twenty one days after surgery, animals were euthanized and the abraded area was examined, with adhesion formation being evaluated following a procedure similar to that of the Sprague-Dawley rat cecum model.

17.2. RESULTS

When injury occurs, the body sets in motion a complex set of responses designed to restore the injured area. In the final stages of healing, connective tissue forms at the wound site to regenerate the body structure and protect the affected area from further damage. In some instances this cascade of events does not work properly and can lead to life threatening conditions.

For example, as a visceral organ heals following surgery, a fibrin clot generated during the surgical procedure may invade the surface of adjoining organs forming a link which allows for fibroblast migration. This migration leads to collagen deposition and tissue growth, which in turn causes the organs involved to adhere to one another.

Such adhesions, referred to as post-surgical adhesions, may produce pain, obstruction and malfunction by distorting the organ or organs involved. Immobilized joints, intestinal obstruction and infertility are often linked to the formation of post-surgical adhesions. Furthermore, post-surgical adhesion will complicate and extend the length of future surgical procedures in the surrounding region. This last issue is of particular relevance to open heart surgeries and cesarean section obstetrical procedures where additional surgeries may be required. The formation of adhesions is very common following abdominal, cardiovascular and orthopedic surgical procedures.

When adhesions become pathological and seriously interfere with organ function, surgical adhesiolysis (sharp or blunt dissection of the adhesion in conjunction with meticulous surgical techniques) is the treatment that is currently used to eliminate adhesions. In 1991, approximately 500,000 adhesiolysis procedures were performed in the U.S. This procedure is, however, notoriously ineffective, with the frequency of recurrence of adhesion formation reported to be as high as 90%. Further, no other technique or composition has proven effective in the prevention of such post-surgical adhesions.

The results presented herein, therefore, are significant in that they demonstrate the effectiveness of the p-GlcNAc materials of the invention for the prevention of post-surgical adhesions. Specifically, the results presented here demonstrate the efficacy of p-GlcNAc based solid and liquid formulations as barriers to the formation of abdominal post-surgical adhesions in accepted rat and pig animal model systems.

One of the accepted animal models used to study adhesion formation employs visceral-parietal peritoneal adhesions in Sprague-Dawley rats. Both partially deacetylated p-GlcNAc membranes and p-GlcNAc-lactate gel formulations prevented and/or considerably reduced the incidence of adhesion formation as compared with either non-treated controls or treated with InterCEED™ (Johnson & Johnson), the only commercially available product for this indication.

Specifically, a total of 18 rats were used to test p-GlcNAc-lactate gel formulations. 12 animals were used as controls, with 6 receiving no treatment and 6 receiving InterCeed™. 6 animals received 0.25% p-GlcNAc-lactate gel, 10% propylene glycol, water. Animals receiving the p-GlcNAc-lactate gel treatment showed a significantly reduced incidence of postoperative adhesion formation, compared to either of the controls, as shown, below, in Table VIII.

TABLE VIII

| | Extent of Involvement | Tenacity |
|---|---|---|
| Control (No treatment) | 1 +/− 2.1 | 1 +/− 1.5 |
| InterCEED ™ | 1 +/− 1.8 | 1 +/− 1.5 |
| p-GlcNAc-lactate gel | 0 +/− 0.8 | 1 +/− 1.2 |

Partially deacetylated p-GlcNAc membranes were also tested for their ability to reduce or prevent the occurrence of post-surgical adhesions in the rat animal model. A total of 22 rats were used in the study. 12 animals were used as controls, with 6 receiving no treatment and 6 receiving InterCEED™. Ten animals each received a 1 cm ×1 cm membrane of an approximately 60% deacetylated p-glcNAc formulation. The animals which received the partially deacetylated p-GlcNAc membrane showed a significant reduction in the incidence of formation of postoperative adhesions, as compared with the non-treated controls and InterCEED™, as shown, below, in Table IX.

TABLE IX

| | Extent of Involvement | Tenacity |
|---|---|---|
| Control (No treatment) | 3 +/− 1.8 | 1 +/− 0.6 |
| InterCEED ™ | 3 +/− 1.6 | 1 +/− 0.4 |
| p-GlcNAc-membrane | 1 +/− 0.8 | 1 +/− 0.3 |

Large animal bowel models for the prevention of peritoneal adhesions were also used to test p-GlcNAc compositions. Specifically, six pigs and one horse were used to study both the partially deacetylated p-GlcNAc membrane and the p-GlcNAc-lactate gel. The partially deacetylated p-GlcNAc membrane consisted of a 2 cm ×2 cm piece of 60% deacetylated p-GlcNAC membrane, while the p-GlcNAc-lactate gel consisted of 0.25% p-GlcNAc lactate formulated with 10% propylene glycol and water. Control animals received no treatment to the wounded site.

The results of these large animal studies revealed that, while the control sites formed multiple adhesions and scar tissue in the surrounding site, both the p-GlcNAc membrane and gel formulations effectively reduced the formation of adhesions.

Samples from control and treated sites were additionally examined using SEM, which showed an increased amount of fibrosis in the control sites as compared to the treated tissues.

18. EXAMPLE: BIODEGRADABILITY OF p-GlcNAc MATERIALS

The Example presented in this Section demonstrates that p-GlcNAc materials of the invention may be prepared which exhibit controllable in vitro and in vivo biodegradability and rates of resorption.

18.1. MATERIALS AND METHODS p-GlcNAc materials: Prototype I was made by the method described, above, in Section 5.3.2, via the chemical method, with hydrofluoric acid being utilized as the chemical reagent. Prototype I represented 100% acetylated p-GlcNAc.

The p-GlcNAc starting material of prototype 3A was made by the method described, above, in Section 5.3.2, via the chemical method, with hydrofluoric acid being utilized as the chemical reagent. The p-GlcNAc material was then deacetylated by the method described, above, in Section 5.4. Specifically, the p-GlcNAc material was treated with a 40% NaOH solution at 60° C. for 30 minutes. The resulting prototype 3A was determined to be 30% deacetylated.

The p-GlcNAc starting material of prototype 4 was made by the method described, above, in Section 5.3.2, via the chemical method, with hydrofluoric acid being utilized as the chemical reagent. The p-GlcNAc material was then deacetylated by treatment with a 40% NaOH solution at 60° C. for 30 minutes. Next, the fibers were suspended in distilled water, frozen at −20° C., and lyophilized to dryness. Prototype 4 was also determined to be 30% deacetylated.

Abdominal implantation model: Sprague Dawley albino rats were utilized for the abdominal implantation model studies. Animals were anesthetized and prepared for surgery, and an incision was made in the skin and abdominal muscles. The cecum was located and lifted out. A 1 cm ×1 cm membrane of p-GlcNAc material was placed onto the cecum, and the incision was closed with nylon. Control animals were those in which no material was placed onto the cecum.

Animals were opened at 14 and 21 days post implantation. Photographs were taken during the implant and explant procedures (FIGS. 23A–E). Samples of cecum were prepared for histopathology after the explant procedure.

p-GlcNAc in vitro degradation lysozyme-chitinase assay: The assay is a colorimetric assay for N-acetyl glucosamine, and was performed as follows: 150 µl of a reaction sample was pipetted into 13×100 mm glass disposable test tubes, in duplicate. 25 µl of 0.25M potassium phosphate buffer (pH 7.1) was added to each test tube, followed by the addition of 35 µl of 0.8M potassium borate solution (pH 9.8). Tubes were immediately immersed into an ice-bath for a minimum of 2 minutes. Samples were then removed from the ice-bath, 1 ml of freshly prepared DMAB reagent was added, and the samples were vortexed. DMAB (Dimethyl aminobenzaldehyde) reagent was made by adding 70 mls of glacial acetic acid and 10 mls of 11.6N (concentrated) HCl to 8 grams of p-dimethyl aminobenzaldehyde. Samples were then incubated at 37° C. for 20 minutes.

To prepare a standard curve, the following procedure was utilized. A GlcNAc stock solution was diluted to 0.1 mg/ml with 0.010M sodium acetate buffer (pH 4.5), and 0 µl, 20 µl, 30 µl, 90 µl or 120 µl of the diluted GlcNAc solution was added to a set of test tubes. This was followed by the addition of 150 µl, 130 µl, 60 µl or 30 µl, respectively, of 0.010M sodium acetate buffer (pH 4.5) to the test tubes. Next, 25 µl of 0.25M potassium phosphate buffer (pH 7.1) and 35 µl of 0.8M potassium borate buffer (pH 9.8) were added to each test tube. A duplicate set of test tubes is prepared by the same procedure.

Figure 23:
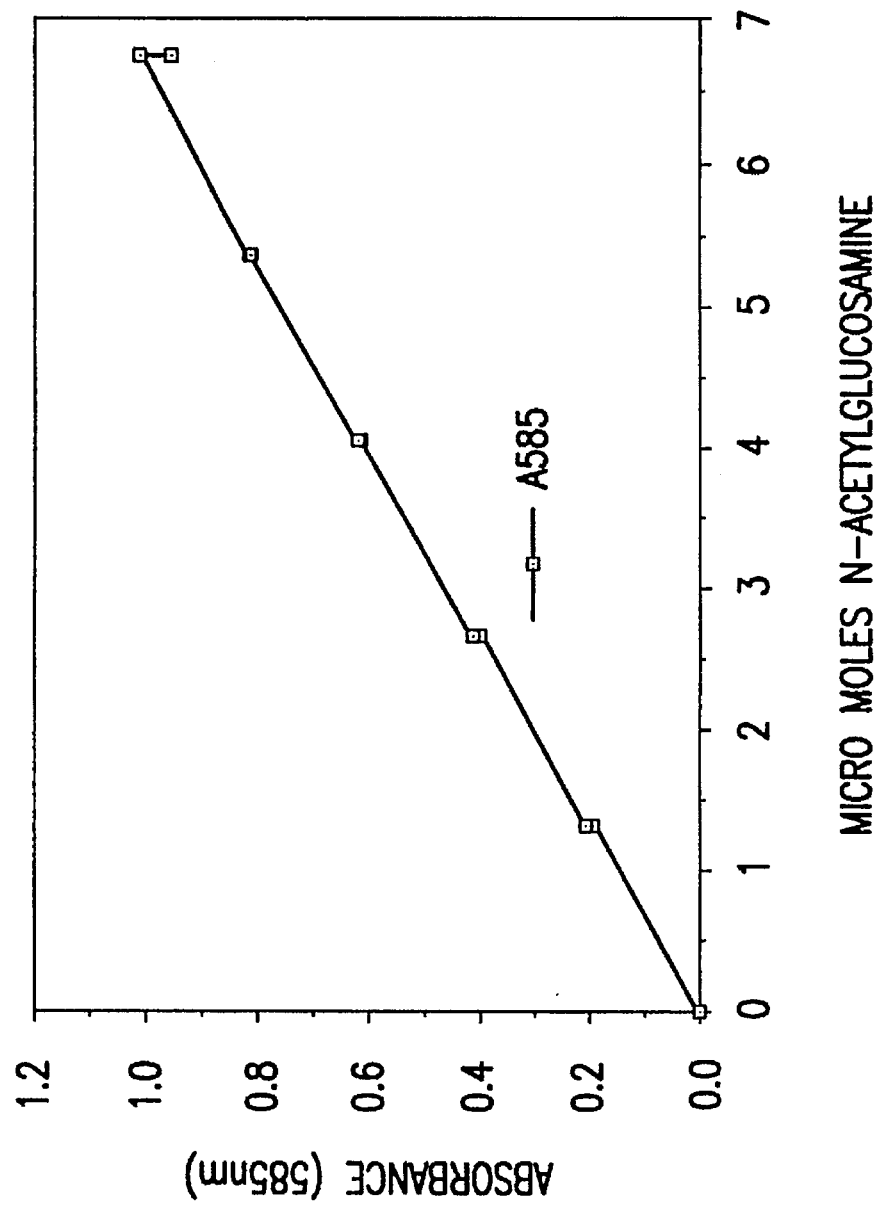
FIG. 23. A typical standard curve obtained using the procedure described, below, in Section 18.1. A standard curve such as this one was used in the lysozyme-chitinase assay also described, below, in Section 18.1.

The test tubes are capped and boiled at 100° C. for exactly 3 minutes. The tubes are then immersed in an ice bath. The tubes are removed from the ice bath and 1 ml of DMAB reagent, freshly prepared according to the method described above in the Section, is added to each tube. The tubes are incubated at 37° C. for 20 minutes. The absorbance of the contents of each tube is read at 585 nM. Absorbance should be read as quickly as possible. The standard curve is plotted on graph paper and used to determine the concentration of N-acetyl glucosamine in the reaction samples. A typical standard curve is shown in FIG. 23.

18.2. RESULTS

The in-vitro biodegradability of p-GlcNAc materials was studied in experiments which assayed the relative susceptibility of p-GlcNAc membrane materials to degradation by lysozyme. p-GlcNAc membranes were exposed to an excess of lysozyme in a 10 mM acetate buffer, and the subsequent release of N-acetyl glucosamine was determined using the assay described, above, in Section 18.1.

Figure 24:
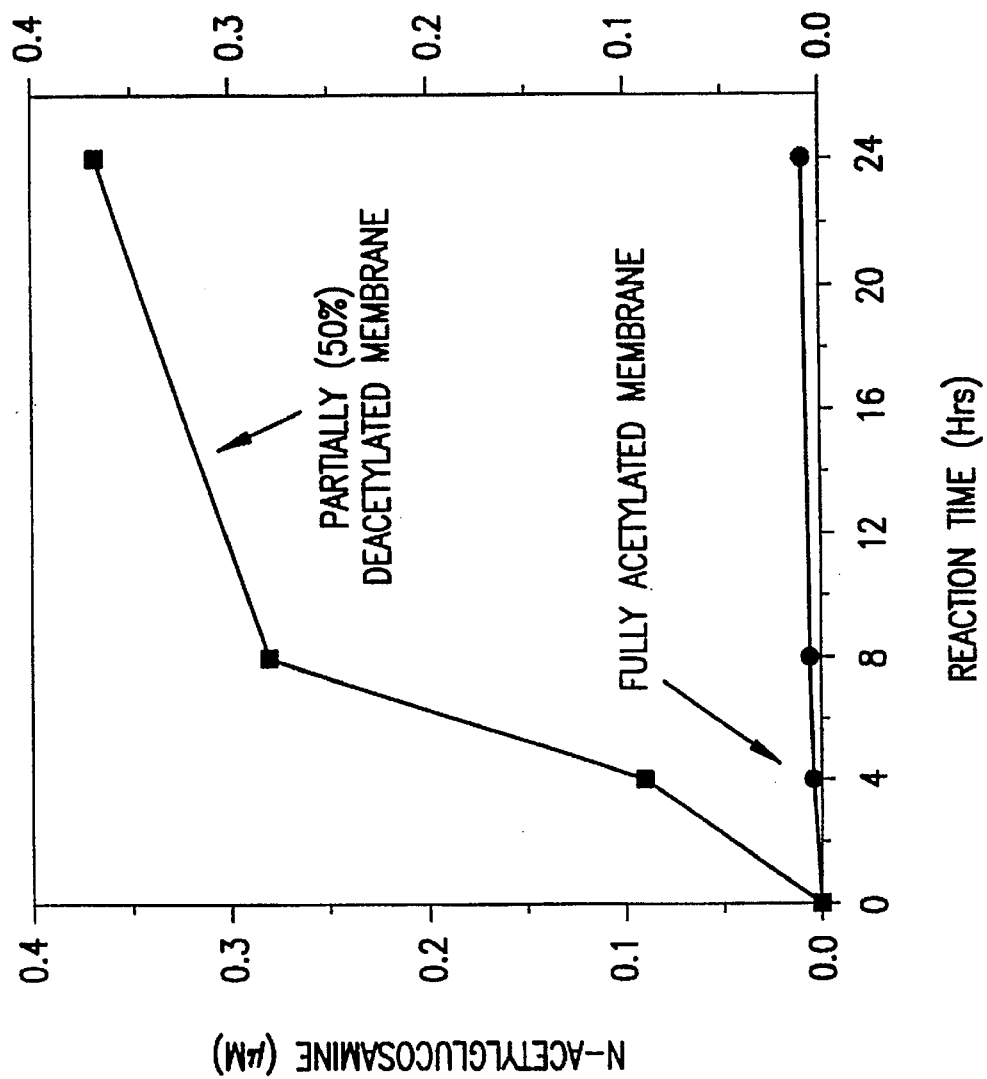
FIG. 24. p-GlcNAc lysozyme digestion data. The graph presented here depicts the accumulation of N-acetylglucosamine over time, as p-GlcNAc membranes are digested with lysozyme. The graph compares the degradation rate of fully acetylated p-GlcNAc to partially (50%) deacetylated p-GlcNAc, and demonstrates that the degradation rate for the partially deacetylated p-GlcNAc was substantially higher than that of the fully acetylated p-GlcNAc material.
Figure 25:
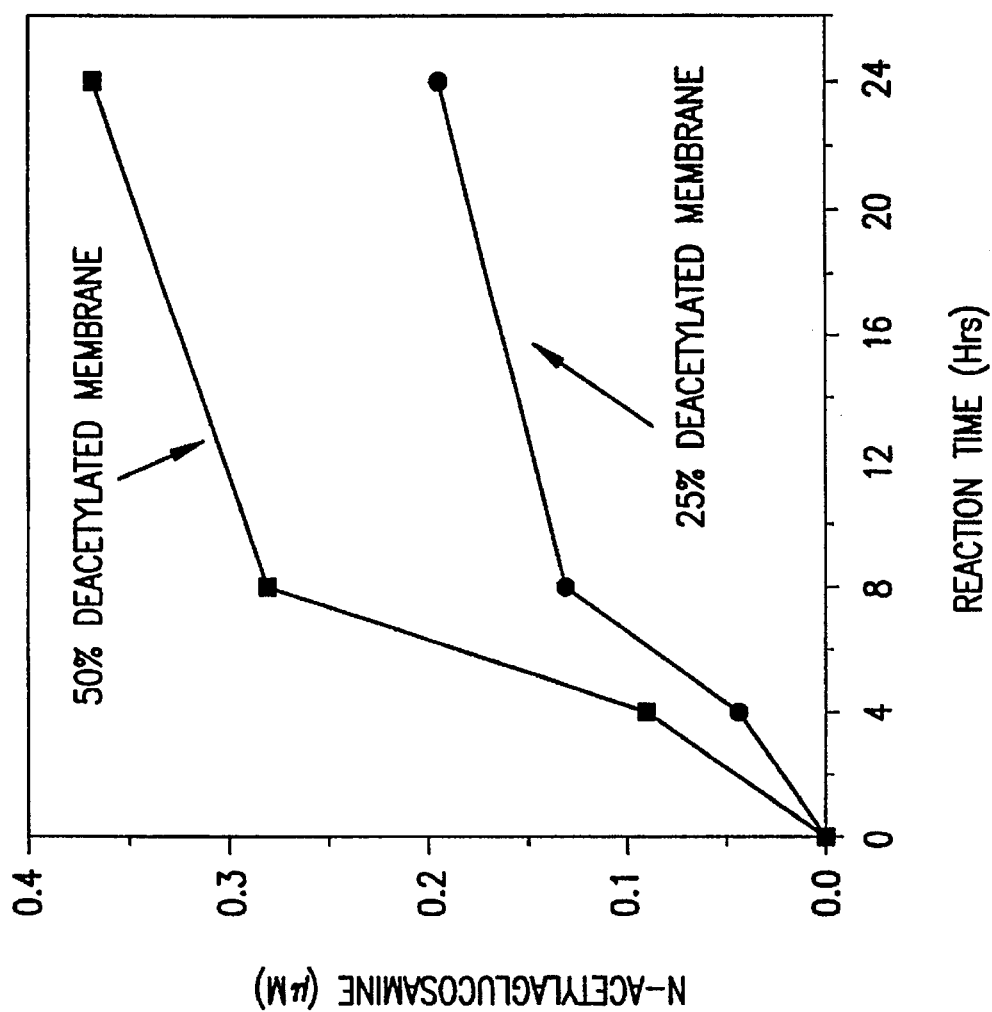
FIG. 25. p-GlcNAc lysozyme digestion data. The graph presented here depicts the accumulation of N-acetylglucosamine over time, as p-GlcNAc membranes are digested with lysozyme. The graph compares the degradation rate of two partially deacetylated p-GlcNAc membranes (specifically a 25% and a 50% deacetylated p-GlcNAc membrane). The data demonstrate that the degradation rate increases as the percent of deacetylation increases, with the degradation rate for the 50% deacetylated p-GlcNAc membrane being substantially higher than that of the 25% deacetylated p-GlcNAc membrane.

The results of these experiments indicated that partially deacetylated membranes are more susceptible to digestion by lysozyme (see FIG. 24) and, further, that the rate of lysozyme degradation is directly related to the extent of deacetylation (see FIG. 25, which compares the degradation rates of a 50% to a 25% deacetylated p-GlcNAc membrane).

p-GlcNAc in vivo degradation

Additionally, experiments were performed which addressed the in-vivo biodegradability of p-GlcNAc materials. Such experiments utilized an abdominal implantation model. Three p-GlcNAc materials, as listed below, were tested.

p-GlcNAc materials tested:

1) p-GlcNAc, fully acetylated (designated prototype 1);

2) partially deacetylated p-GlcNAc membrane (designated prototype 3A); and 3) lyophilized and partially deacetylated p-GlcNAc membrane(designated prototype 4).

Results

Figure 26A:
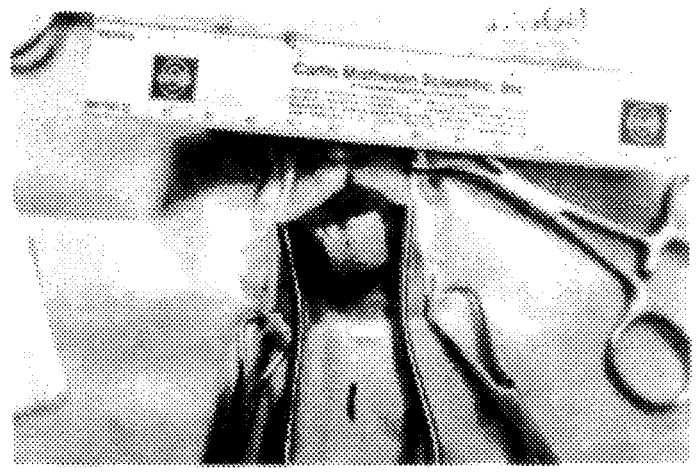
FIG. 26A–26E. p-GlcNAc in vivo biodegradability data.
Figure 26B:
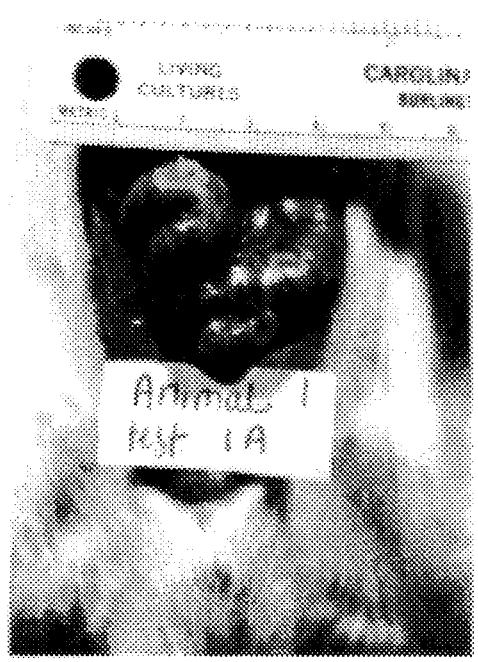
Figure 26C:
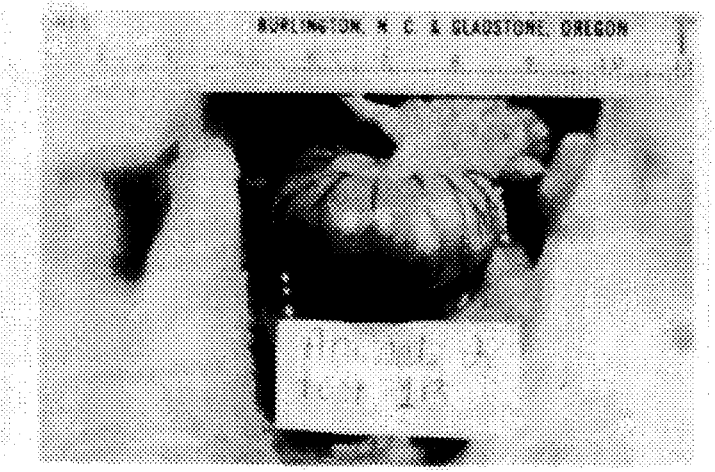
Figure 26D:
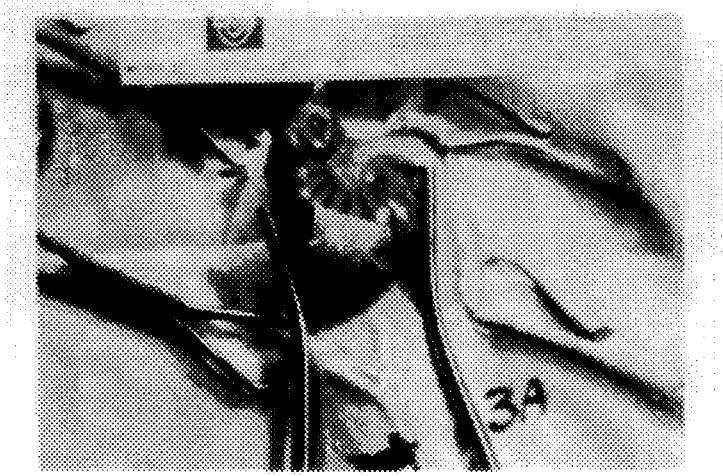
Figure 26E:
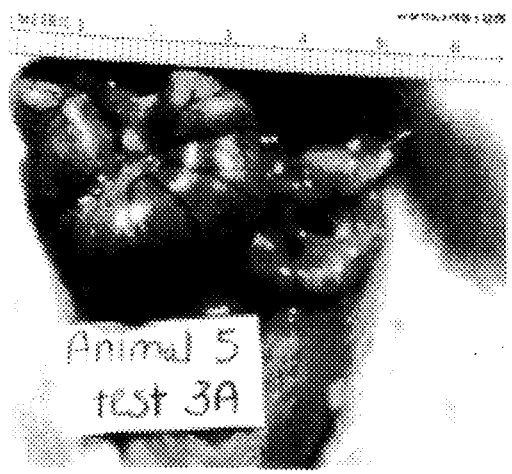

The fully acetylated p-GlcNAc (prototype 1) was resorbed within 21 days, as shown in FIGS. 26A–26C. The partially deacetylated p-GlcNAc membrane (prototype 3A) was completely resorbed within 14 days, as shown in FIGS. 26D–26E. The lyophilized and partially deacetylated p-GlcNAc membrane (prototype 4) had not yet been completely resorbed after 21 days post-implantation.

Histopathology analyses showed that once the p-GlcNAc material has been resorbed there were no histological differences detectable between tissue samples obtained from the treated and from the control animals.

19. EXAMPLE: p-GlcNAc HEMOSTASIS STUDIES

The experiments described herein study the efficacy of the p-GlcNAc materials of the invention for the control of bleeding. The success of the p-GlcNAc materials in controlling bleeding is, further, compared against commercially available hemostatic products.

19.1. MATERIALS AND METHODS p-GlcNAc and control materials: partially deacetylated (approximately 70%) p-GlcNAc membranes were made using the chemical separation technique described, above, in Section 5.3.2, with hydrofluoric acid being utilized as the chemical reagent, and the techniques described, above, in Section 5.4. 2 cm ×1 cm pieces were used. p-GlcNAc-lactate gel (4% p-GlcNAc-lactate, formulated in propylene glycol and water) was produced following the methods described, above, in Section 17.1. The control material utilized for the study of bleeding in the spleen and liver was Gelfoam™ (Upjohn Company). Gelfoam™ and Avitene™ (Medchem Products, Inc.) were the control materials used in the study of small blood vessel bleeding.

Test animals: New Zealand White rabbits were used. 3 animals received two wounds in the spleen and one wound in the liver. 4 animals received five surgical wounds to blood vessels of similar size in the caudal mesenteric artery system.

Surgical preparation: The animals were anesthetized with ketamine HCl and Xylazine. The animals were placed in dorsal recumbency, and all the hair from the abdomen was removed. The abdomen was then scrubbed with povidone-iodine and 70% isopropyl alcohol and draped for aseptic surgery.

Liver/spleen surgical procedures: A midline incision was made and either the spleen or liver was exteriorized and packed with moist sponges. A 3–4 mm diameter cork borer was used to make a circular wound of about 2 mm depth at one end of the organ. Once the splenic tissue was removed, a pre-weighed 4"×4" gauze sponge was used to absorb all the blood lost from the splenic wound for a period of one minute. The sponge was re-weighed to quantify the amount of blood lost from that particular wound. The test animal was then treated by application to the wound of one of the treatment materials. The time until hemostasis and the amount of blood lost prior to hemostasis was recorded.

After hemostasis in the first wound was achieved, a second wound in the spleen and one wound in the liver were made following the same procedure.

Small blood vessel surgical procedure: A midline incision was made and the small bowel was exteriorized exposing the caudal mesenteric artery system. The bowel was packed with moist sponges and five blood vessels of about the same size were identified. A scalpel was used to make a wound of about 1 mm depth at one of the vessels. A pre-weighed 4"×4" gauze sponge was used to absorb all the blood lost from the vessel wound for a period of one minute. The sponge was re-weighed to quantify the amount of blood lost from that particular wound. The animal was then treated by application to the wound of one of the treatment materials. The time until hemostasis occurred and the amount of blood lost prior to hemostasis were recorded.

After hemostasis in the first wound was achieved, four more wounds were made following the same procedure.

19.2. RESULTS p-GlcNAc materials were tested for their ability to control bleeding in the spleen and liver of rat animal models. The p-GlcNAc materials tested were: 1) partially deacetylated (approximately 70%) p-GlcNAc; and 2) p-GlcNAc-lactate gel (4% p-GlcNAc-lactate, formulated in propylene glycol and water). The effectiveness of these p-GlcNAc materials was compared to Gelfoam™ (Upjohn Company).

Each material was tested three times (twice in the spleen and once in the liver). Both of the p-GlcNAc based materials exhibited an effectiveness in controlling bleeding within the first minute after application which was comparable to that of Gelfoam™. The p-GlcNAc based materials have additional advantages. Specifically, the p-GlcNAc materials do not need to be held in place during the procedure, may be left in the body, where they will be resorbed within two to three weeks (Gelfoam™ is not indicated for this purpose), are compatible with both general and minimally invasive surgical procedures.

Next, the efficacy of p-GlcNAc based materials in the control of bleeding in small blood vessels was studied, and compared against commercially available hemostatic products.

Each material was tested five times (twice in one of the animals and once in the other three animals). The p-GlcNAc membrane and gel formulations were easily applied to the site and controlled the bleeding within 2 minutes. Gelfoam™, which had to be held in place in order to perform its function achieved hemostasis within the same 2 minute range as the p-GlcNAc materials. Avitene™, a fibrous material made of collagen, was difficult to handle and required more than five minutes to control the bleeding.

Thus, the results described herein demonstrate that the p-GlcNAc materials tested here represent effective, convenient hemostatic agents.

20. EXAMPLE: p-GlcNAc DRUG DELIVERY SYSTEMS

Described herein are studies demonstrating the successful use of p-GlcNAc materials to deliver anti-tumor drugs to the site of malignant skin cancer and colon cancer tumors such that the delivered anti-tumor drugs exhibit a therapeutic impact upon the tumors.

20.1. MATERIALS AND METHODS p-GlcNAc-lactate drug delivery compositions: Mixtures of 5'-fluorouracil (5'-FU) and p-GlcNAc-lactate were formulated as follows; 0.5 mL of 5'-FU (50 mg/mL) was mixed with 0.5 mL of propylene glycol, and 2.0 mL of 4% p-GlcNAc-lactate was added and mixed. The p-GlcNAc-lactate was produced using the techniques described, above, in Section 5.4. Even after extensive mixing, the 5'FU did not completely dissolve into the p-GlcNAc-lactate gel. Assuming complete mixing, the final concentration of 5'-FU would be 6.25 mg/mL.

Mixtures of mitomycin (Mito) and p-GlcNAc-lactate were formulated as follows; 0.5mg of Mito (lyophilized powder) were dissolved in 5ml of propylene glycol, and 0.5 ml of the Mito solution was mixed with 0.5 mL of MPT's 4% p-GlcN-lactate preparation to give a final Mito concentration of 0.2 mg/ml and a final p-GlcNAc-lactate concentration of 2%. The materials were compatible, with the Mito dissolving easily into the p-GlcNAc-lactate gel. p-GlcNAc membrane 5'FU delivery compositions: Samples of 5'-fluorouracil (5'-FU) were immobilized into disks of pure p-GlcNAc membrane material produced using the chemical separation method described, above, in Section 5.3.2, with hydrofluoric acid being utilized as the chemical reagent. Each disk described here had a diameter of 1.5 cm, as described here. For the preparation of high dose (HD) disks, 0.64 mL of a 50 mg/mL solution of 5'-FU was mixed with suspensions containing approximately 8 mg of pure p-GlcNAc. The mixtures were allowed to stand for several hours to promote the absorption of 5'-FU into the p-GlcNAc, and were then dried at 55° C. for 3.5 hours. The resulting HD disks contained a total of 32 mg 5'-FU, which is equivalent to approximately twice the normal total 14 day dose of 5'-FU typically given to a cancer patient, normalized to the weight of the experimental mice based on the typical dose of 5'-FU per Kg body weight for humans. It should be noted here, and in the low dose concentrations described below, that the amount of 5'-FU contained in the disks was approximated and was based only on the amount of 5'-FU put into the suspensions.

Low dose (LD) 5'-FU containing p-GlcNAc disks were prepared in the same manner, except that the LD disks contained 17 mg of 5'-FU, an amount equivalent to equal the normal total human dose for a 14 day period, normalized to the weight of the experimental mice based on the typical dose of 5'-FU per Kg body weight for humans.

Test Animals: For the 5'FU study, SCID (severe combined immunodeficiency) mice were inoculated with subcutaneous flank injections of HT-29 colon cancer cells (ATCC; $1\times10^5$ cells per inoculum) obtained by standard tissue culture methods, in order to produce HT-29 colon cancer tumors. These injections led to palpable tumors which were harvested in 14–21 days. Tumors were dissected and necrotic tissue was cut away. The HT-29 colon cancer tumors were sliced into 3×3×3 mm pieces.

The experimental SCID mice were anesthetized via intraperitoneal injections with a standard dose of Avetin, and a slice of HT-29 colon cancer tumor was implanted onto the cecum of each mouse. Specifically, each mouse was surgically opened to expose its abdomen and the cecum was located, which was nicked with a scalpel to make a small incision. A 3×3×3 mm tumor slice was sutured over the incision onto the cecum using 5.0 silk sutures. The abdomen was then closed using Clay Adams staples.

All mice were caged singly and fed for two weeks. All mice were healthy and none had obstructed colons at the end of the two week period.

On day 14, each mouse was anesthetized, and its abdomen was reopened. The growing tumors were measured (length and horizontal dimensions). Tumors were then treated with the p-GlcNAc/anti-tumor drug or were used as controls.

Six mice were used for the p-GlcNAc-lactate 5'FU study, and 15 mice were used for the p-GlcNAc membrane 5'FU study.

For the mitomycin study, nine SCID mice were inoculated with sub-cutaneous injections of A431 squamous cell skin cancer cells (ATCC; $1\times10^5$ cells per inoculum). Tumors resulted in all mice within 14 days.

Treatments: For the p-GlcNAc-lactate 5'FU study, animals were treated once daily by "painting" the 5'-fluorouracil (5'-FU)-containing p-GlcNAc gel mixture onto the skin area over the tumor mass. Measurements of the tumor size were obtained daily. Control animals included animals treated with p-GlcNAc alone, without 5'-FU, and animals which received no treatment.

For the p-GlcNAc membrane 5'FU study, the HT29 colon tumors in the SCID mice were treated by surgically implanting disks of the drug-containing p-GlcNAc membrane material directly onto their surface, after having allowed the tumor to grow on the colon for 14 days. Mice were sacrificed 14 days following the implant procedure. Measurements of tumor volumes were made immediately prior to implanting the drug-containing p-GlcNAc membranes on day 0 and at the termination of the experiment on day 14. Control animals included ones treated with the p-GlcNAc membrane without 5'-FU, and controls which received no treatment. Additionally, two animals received daily systemic injections of 5'-FU in doses equivalent to the HD and LD regimen.

For the p-GlcNAc-lactate Mito study, animals were treated daily as in the p-GlcNAc-lactate 5'-FU study, with 3 animals being treated with the Mito containing mixture. In addition, 3 animals were treated with p-GlcNAc minus Mito, 2 animals received no treatment, and 1 animal received propylene glycol.

20.2. RESULTS

20.2.1. p-GlcNAc-LACTATE 5'FU

Experiments designed to study the effect of p-GlcNAc-lactate Mito drug delivery systems on tumor size were conducted, as described, above, in Section 20.1.

The largest length and width dimension were measured for each tumor and the cross-sectional area using these dimensions was calculated. The cross-sectional area values are shown in Table X, below.

TABLE X

| Animal # | Treatment | Day 0 | Day 4 | Day 11 | Day 15 |
|---|---|---|---|---|---|
| | | Tumor Size (cm$^2$) | | | |
| 1 | CL + 5FU | 63 | 90 | 168 | 156 |
| 2 | CL + 5FU | 48 | 56 | 70 | 88 |
| 3 | CL Control | 21 | 36 | 88 | 108 |
| 4 | CL Control | 58 | 110 | 150 | 195,30 |
| 5 | Nothing | 40 | 64 | 132 | 234 |
| 6 | Nothing | 28 | 42 | 100 | 132 |
| | | % Increase in Size | | | |
| 1 | CL + 5FU | 0 | 43 | 167 | 147 |
| 2 | CL + 5FU | 0 | 17 | 47 | 84 |
| 3 | CL Control | 0 | 71 | 319 | 414 |
| 4 | CL Control | 0 | 90 | 160 | 289 |
| 5 | Nothing | 0 | 61 | 232 | 488 |
| 6 | Nothing | 0 | 48 | 253 | 366 |

Figure 27:
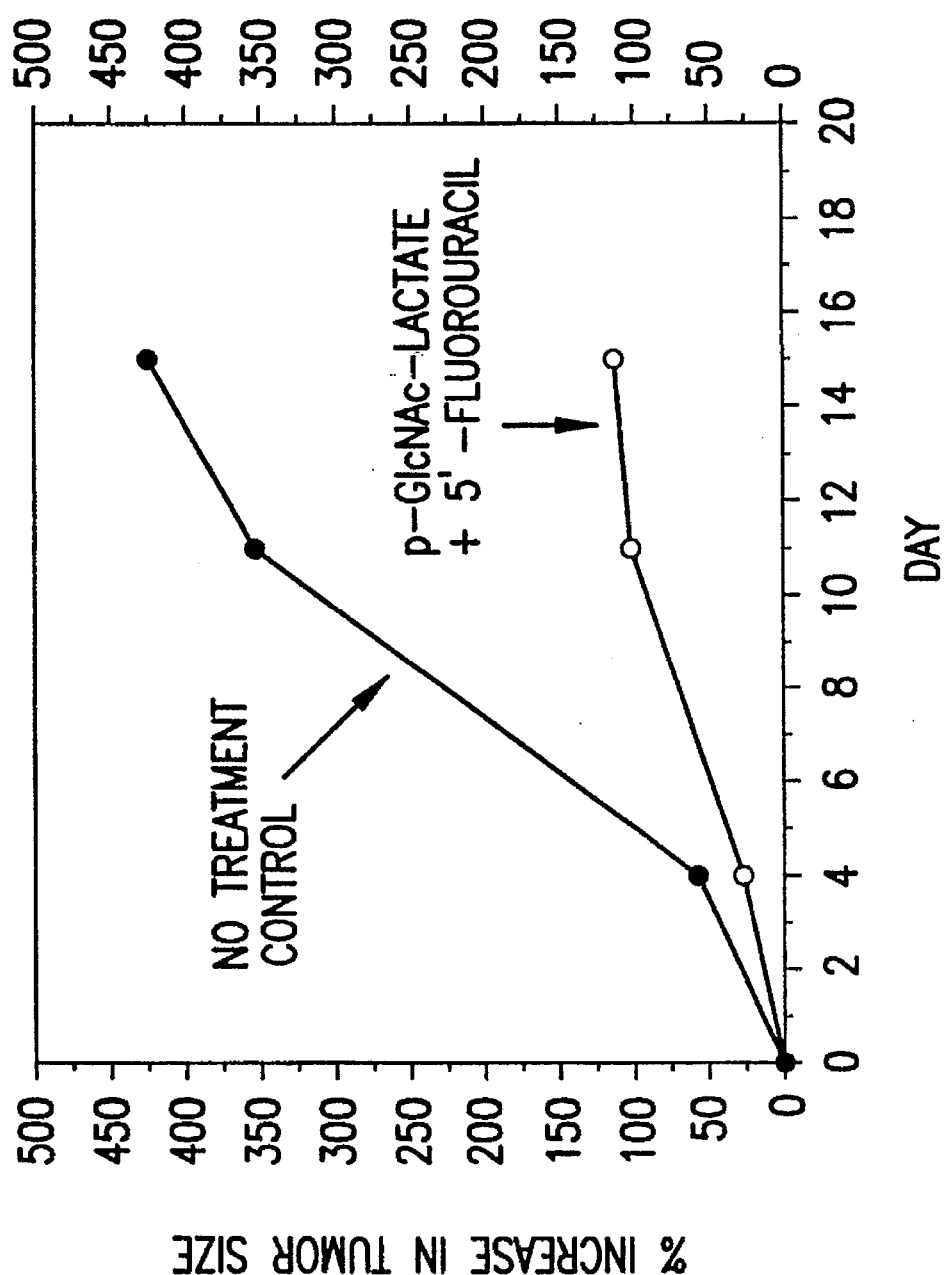
FIG. 27. The graph depicted here illustrates data concerning the percent increase in tumor size of animals which either received no treatment (●) or received p-GlcNAc-lactate/fluorouracil (5'-FU) (○), as described, below, in Section 20.1.
Figure 28:
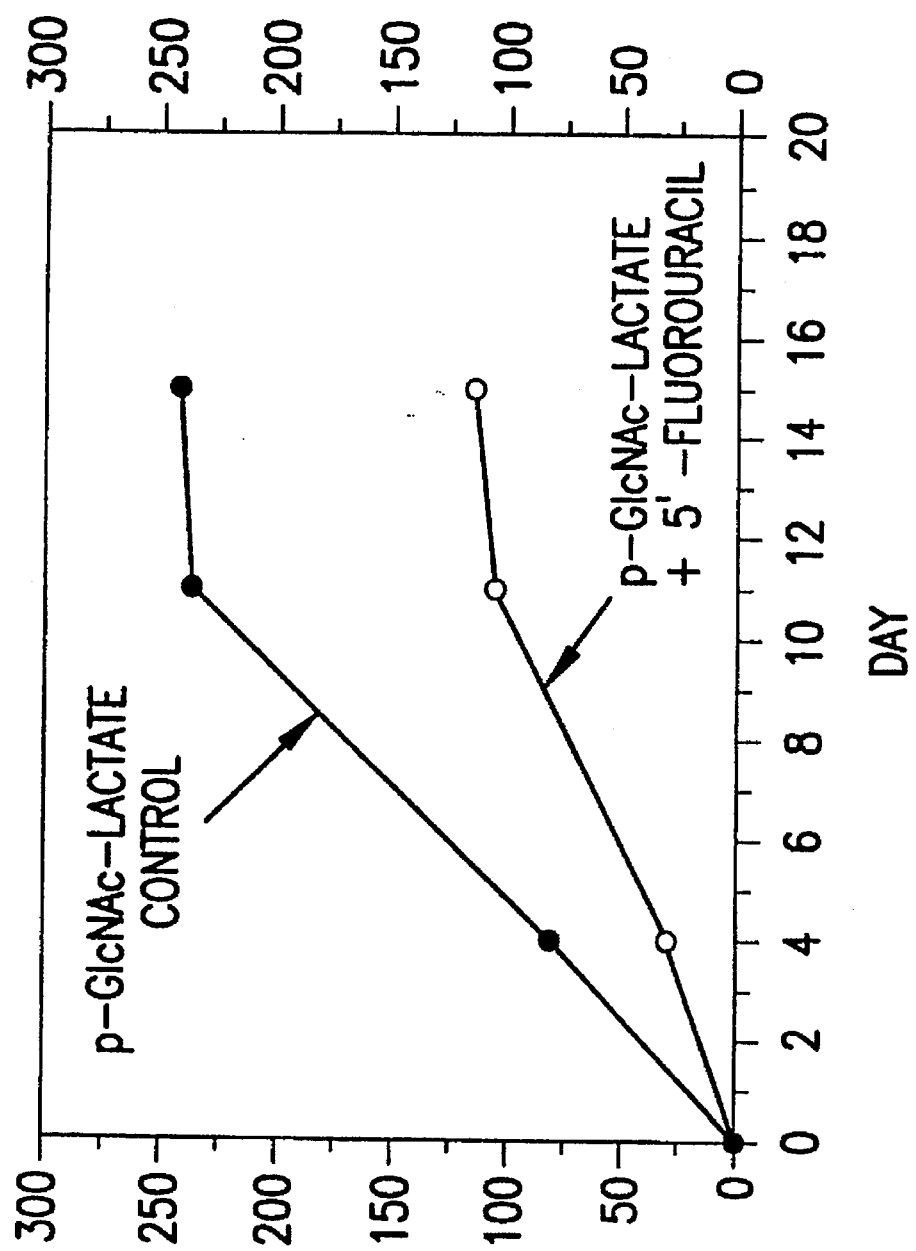
FIG. 28. The graph depicted here illustrates data concerning the percent increase in tumor size of animals which either received p-GlcNAc-lactate alone (●) or received p-GlcNAc-lactate/fluorouracil (5'-FU) (○), as described, below, in Section 20.1.

The data comparing p-GlcNAc-lactate 5'FU treated animals with controls are shown in FIGS. 27–28. The data summarized in Table X and FIGS. 27–28 clearly suggest that the HT-29 subcutaneous tumors in the rats treated with the 5'-FU containing p-GlcNAc-lactate gels have a significantly retarded rate of growth compared to controls. Their growth has been slowed 2.5-fold in comparison to the p-GlcNAc-lactate gel controls and 4-fold compared to the no treatment controls.

20.2.2. p-GlcNAc-LACTATE MITO

Experiments designed to study the effect of p-GlcNAc-lactate 5'FU drug delivery systems on tumor size were also conducted, as described, above, in Section 20.1.

The largest length and width dimensions were measured for each tumor and the cross sectional area using these dimensions was calculated. The cross-sectional area values were as shown in Table XI, below.

TABLE XI

| Animal # | Treatment | Day 0 | Day 3 | Day 5 | Day 8 |
|---|---|---|---|---|---|
| | | Tumor Size (cm$^2$) | | | |
| 1 | pGlcNAc-Lactate + Mito | 23 | 23 | 42 | 49 |
| 2 | pGlcNAc-Lactate + Mito | 23 | 16 | 54 | 63 |
| 3 | pGlcNAc-Lactate + Mito | 72 | 99 | Term | Term |
| 4 | pGlcNAc-Lactate control | 27 | 54 | 140 | 203 |
| 5 | pGlcNAc-Lactate control | 30 | 54 | 96 | 140 |
| 6 | pGlcNAc-Lactate control | 30 | 58 | 200 | 221 |
| 7 | Nothing | 48 | 75 | 126 | 300 |
| 8 | Nothing | 44 | 80 | 207 | Dead |
| 9 | Propylene glycol | 49 | 86 | 180 | 216 |
| | | % Increase in Size | | | |
| 1 | pGlcNAc-Lactate + Mito | 0 | 0 | 83 | 135 |
| 2 | pGlcNAc-Lactate + Mito | 0 | -30 | 135 | 174 |
| 3 | pGlcNAc-Lactate + Mito | 0 | 38 | Term | Term |
| 4 | pGlcNAc-Lactate control | 0 | 100 | 419 | 652 |
| 5 | pGlcNAc-Lactate control | 0 | 80 | 220 | 367 |
| 6 | pGlcNAc-Lactate control | 0 | 93 | 567 | 637 |
| 7 | Nothing | 0 | 56 | 163 | 525 |

TABLE XI-continued

| Animal # | Treatment | Day 0 | Day 3 | Day 5 | Day 8 |
|---|---|---|---|---|---|
| 8 | Nothing | 0 | 82 | 370 | Dead |
| 9 | Propylene glycol | 0 | 76 | 267 | 341 |

Figure 29:
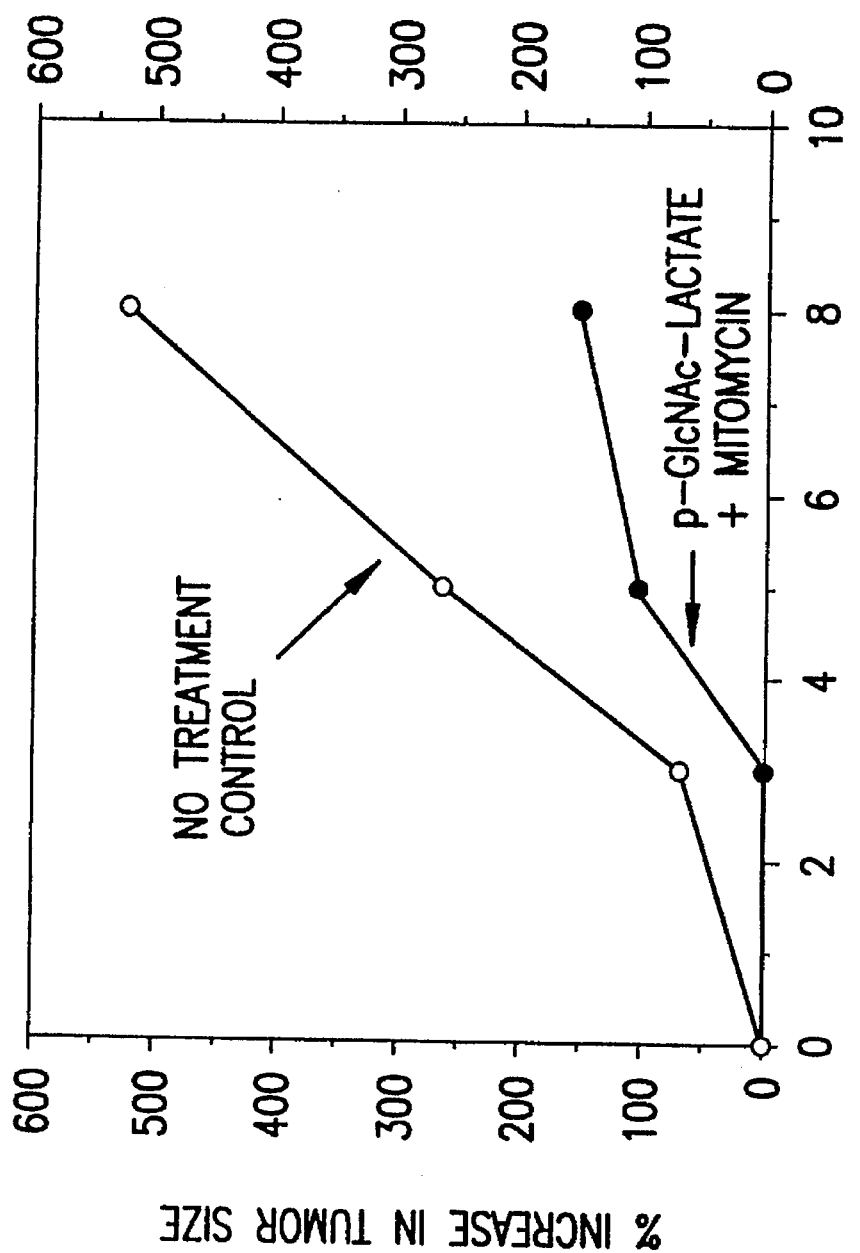
FIG. 29. The graph depicted here illustrates data concerning the percent increase in tumor size of animals which either received no treatment (●) or received p-GlcNAc-lactate/mitomycin (mito) (○), as described, below, in Section 20.1.
Figure 30:
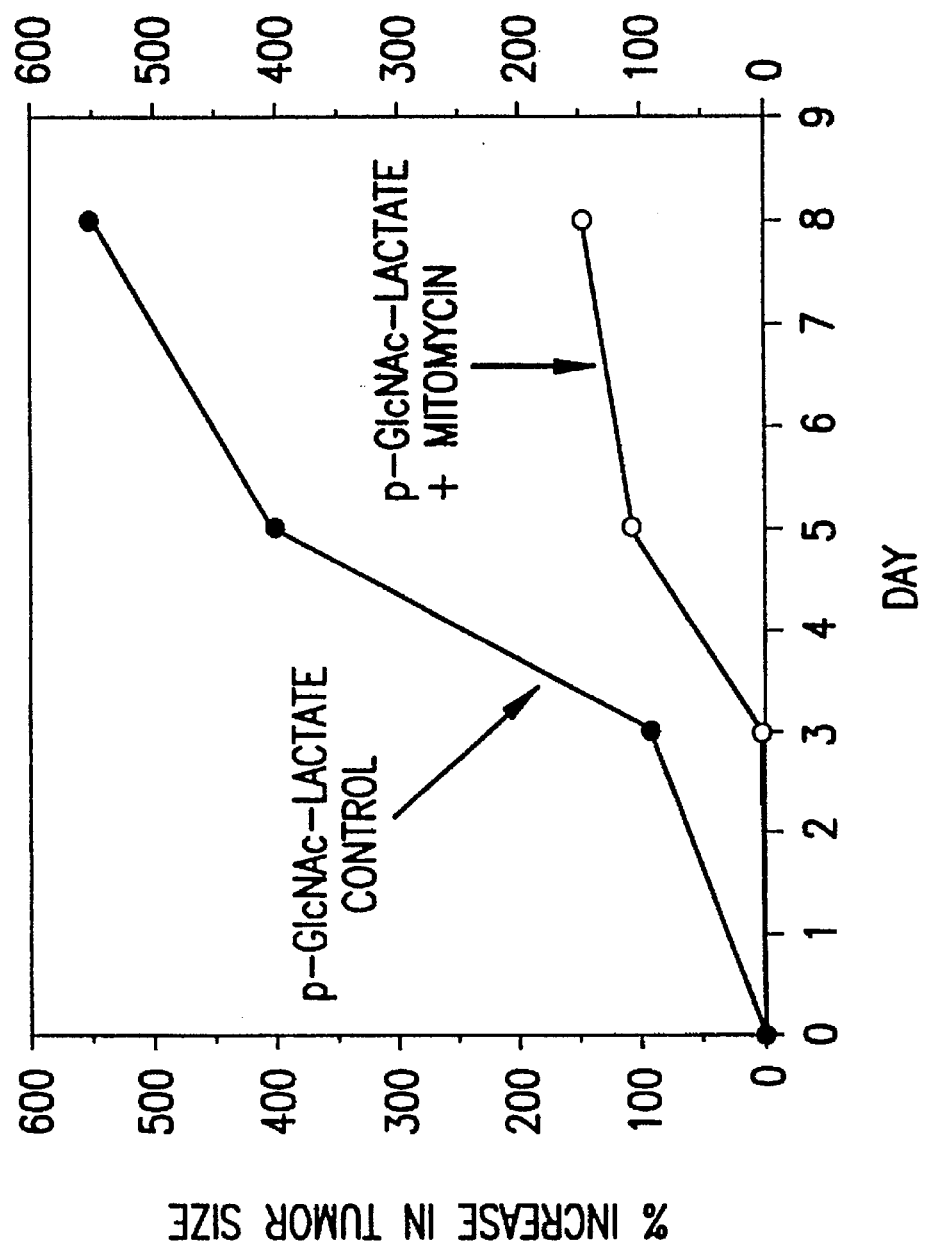
FIG. 30. The graph depicted here illustrates data concerning the percent increase in tumor size of animals which either received p-GlcNAc-lactate alone (●) or received p-GlcNAc-lactate/mitomycin (mito) (○), as described, below, in Section 20.1.

The data comparing p-GlcNAc-lactate Mito treated animals with controls are shown in FIGS. 29–30. The data summarized in Table XI and FIGS. 29–30 clearly suggest that the tumors growing in the rats treated with the Mitomycin-containing p-GlcNAc-lactate gels animals have a significantly retarded rate of growth. Their growth was slowed 4-fold in comparison to the p-GlcNAc-lactate gel controls and 4-fold compared to the no treatment controls.

20.2.3. p-GlcNAc MEMBRANE 5'FU

Next, experiments designed to study the effect of p-GlcNAc membrane 5'FU drug delivery systems on skin cancer tumor size were conducted, as described, above, in Section 20.1.

The tumor volume data obtained during the study, including percent change in volume caused by the different treatments, is summarized in Table XII, below. Tumors were assumed to be cylindrical in shape. Their volumes were determined by measuring their width and length, and using the following equation: $V=\pi r^2 l$, where the radius r is 0.5 times the width and l is the length.

TABLE XII

| p-GlcNAc Membrane + 5'-Fluorouracil Animal Data | | | | | |
|---|---|---|---|---|---|
| Animal # | Treatment | Tumor Volume Pre-Treatment (mm$^3$) | Tumor Volume Post-treatment (mm$^3$) | % Change | Comments |
| A. 5'-FU High Dose: | | | | | |
| 1. 5'-FU HD | | 393 | 283 | -28.0 | |
| 2. 5'-FU HD | | 785 | 308 | -60.8 | |
| 3. 5'-FU HD | | 98.1 | 62.8 | -36.0 | |
| 4. 5'-FU HD | | 785 | 550 | -30.0 | |
| Average per Animal | | | | -38.7 | |
| B. 5'-FU Low Dose: | | | | | |
| 5. 5'-FU LD | | 603 | 170 | -71.9 | |
| 6. 5'-FU LD | | 603 | 615 | 2.0 | |
| 7. 5'-FU LD | | 269 | 198 | -26.0 | |
| 8. 5'-FU LD | | 169 | 226 | 33.3 | |
| Average per animal | | | | -15.7 | |

TABLE XII-continued p-GlcNAc Membrane + 5'-Fluorouracil Animal Data

| Animal # Treatment | Tumor Volume Pre-Treatment (mm³) | Tumor Volume Post-treatment (mm³) | % Change | Comments |
|---|---|---|---|---|
| C. p-GlcNAc Control: | | | | |
| 9. p-GLcNAc Control | 170 | 550 | 320.0 | |
| 10. p-GLcNAc Control | | | | Died day 12 |
| Average per Animal | | | 320.0 | |
| D. No Treatment Control: | | | | |
| 11. No Treatment | 402 | 864 | 215.0 | Sat. tumors |
| 12. No Treatment | 21.2 | 572 | 2700.0 | Sat. tumors |
| Average per Animal | | | 1457.0 | |
| E. 5'-FU via Intravenous Injection - Control: | | | | |
| 13. Low Dose | 402 | 703 | 175.0 | |
| 14. Low Dose | 402 | 402 | 0.0 | Died day 13 |
| 15. High Dose | 402 | 132 | −67.0 | Died day 13 |

Figure 31:
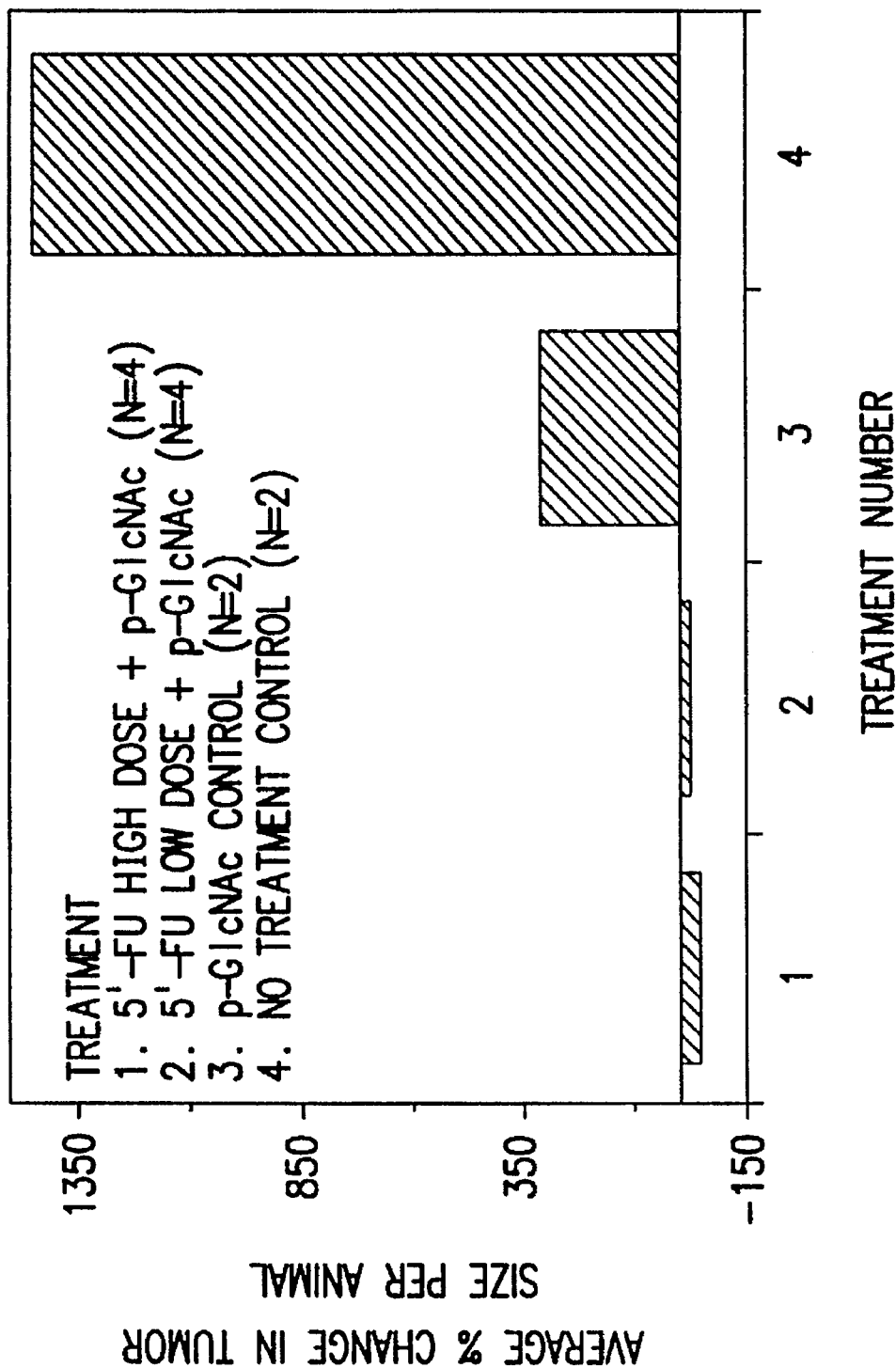
FIG. 31. The bar graph depicted here illustrates the average percent change in tumor size per animal of animals treated with p-GlcNAc/5'-FU high dose (bar 1), p-GlcNAc/5'-FU low dose (bar 2), p-GlcNAc membrane alone (bar 3), and untreated (bar 4). N=4 for bars 1 and 2, n=2 for bars 3 and 4.

FIG. 31 summarizes a portion of the data presented, above, in Table XII. as shown in FIG. 31, the data strongly suggest that tumors treated with the high dose (HD) 5'-FU-containing p-GlcNAc membranes have stopped growing and have, in all cases, actually become significantly smaller. The low dose (LD) polymer materials resulted in disease stability and slight decrease in tumor size. In contrast, the tumors in the control animals continued to rapidly increase in size. It is interesting to note that two of the three control animals which were treated via IV died during the study, indicating that systemic delivery of the equivalent amount of 5'-FU is lethal, whereas site-specific delivery via the p-GlcNAc polymer is efficacious in ridding the animal of the disease.

20.3. CONCLUSION

The data presented in this Section strongly suggest that the site-specific delivery of anti-tumor drugs has a positive effect in retarding and reversing tumor growth. Successful results were obtained using p-GlcNAc drug delivery compositions having two different formulations, namely p-GlcNAc-lactate and p-GlcNAc membrane formulations. Further, successful results were obtained using two different anti-tumor drugs, 5'-FU and Mito. Thus, the p-GlcNAc drug delivery systems of the invention exhibit anti-tumor activity, useful, for example, in the delivery of drugs specifically to the site of the tumor cells of interest.

21. EXAMPLE: FURTHER p-GlcNAc DRUG DELIVERY SYSTEMS

Described herein are further studies demonstrating the successful use of p-GlcNAc materials to deliver 5'-FU to the site of malignant colon cancer tumors such that the delivered 5'-FU exhibit a therapeutic impact upon the tumors.

21.1. MATERIALS AND METHODS p-GlcNAc membrane 5'FU delivery composition:

The p-GlcNAc membrane 5'-FU delivery composition was formulated as described herein.

The aqueous p-GlcNAc suspension used was a 1.0–1.1 mg/ml mixture. 0.70 ml of the p-GlcNAc suspension was filtered using a glass frittered disk funnel and a 0.8 micron, 47 mm membrane filter. After approximately 5–6 minutes on the filtering apparatus, the membrane filter, containing the p-GlcNAc, was removed and placed in a clean petri dish. Using a clean scalpel and forceps, the p-GlcNAc was scraped gently from the membrane and placed into a 2 ml cryovial. At this time, the appropriate amount of 5'-FU (i.e., 50 mg/ml) was added to the p-GlcNAc in the cryovial. For preparation of the control disk, no 5'-FU was added.

For example, to prepare a 0.5× SX disk, 0.17 ml of 5'-FU (50 mg/ml 5'-FU solution) was added for a total of 8 mg of 5'-FU/disk. The cryovial was then securely capped and the contents vortexed until a thick slurry formed. The slurry was then placed into one well of a 48-well plate, and flattened using a glass stirring rod. The above procedure was then repeated until the desired number of p-GlcNAc disks were prepared. After all the disks were placed in the 48-well plate, the plate was covered with Parafilm™ and the contents were frozen for at least one hour. Then, the disks were lyophilized overnight (approximately sixteen hours). Using a sterile needle, the disks were freed from the 48-well plate and flattened using the bottom of a clean dish and light pressure by hand. The disks were stored in clean petri dishes and labeled. It should be noted that autoclaving (e.g., 20 min, 121° C.) the disks does not damage them.

The 1× disks were prepared in the same manner as above except that 0.34 ml of 5'-FU (50 mg/ml 5'-FU solution) was added for a total of 16 mg of 5'-FU/disk. To prepare the 2× disks, 0.68 ml of 5'-FU (50 mg/ml of 5'-FU solution) was added for a total of 32 mg of 5'-FU/disk.

The resulting 0.5× disk contained a total of 8 mg 5'-FU each, which is equivalent to approximately half the normal total 14 day dosage of 5'-FU typically given to a cancer patient by intravenous administration, normalized to the weight of the experimental mice based on the typical dose of 5'-FU per kg of body weight for humans. 1× p-GlcNAc disks containing 5'-FU were prepared in the same manner, except that the 1× p-GlcNAc disks contained 16 mg of 5'-FU, an amount equivalent to equal the normal total 14 day dose of 5'-FU typically given to a cancer patient by intravenous administration, normalized to the weight of the experimental mice based on the typical dose of 5'-FU per kg body weight for humans. 2× p-GlcNAc disks contained 32 mg of 5'-FU, an amount equal to twice times the normal total 14 day dose of 5'-FU typically given to a cancer patient by intravenous administration, normalized to the weight of the experimental mice based on the typical dose of 5'-FU per kg body weight for humans.

Test Animals

The test animals for the present 5'-FU study on HT-29 colon tumors were prepared in the same manner as described in Section 20.1.

Treatments

The mice were treated in the same manner as described in Section 20.1 for the p-GlcNAc membrane 5'-FU study, except that the mice were sacrificed 10 days following the implant procedure.

21.2. RESULTS

The tumor volume data obtained during the study included percent change in volume caused by the different treatments, is summarized below in Table XIII. Tumors were assumed to be cylindrical in shape. Their volumes were determined by measuring their width and length, and using the equation: $V=\pi r^2 l$, where the radius, r, is 0.5 times the width and l is the length.

found in the data presented in Section 20 (suggesting less incorporation of 5'-FU then originally presumed) and the variability in tumor reduction. For example, in Section 20, Table XII shows a wide range of tumor size changes, while in contrast, no such large variations were noted in this Section, as exemplified in Table XIII, above.

22. EXAMPLE: WOUND HEALING STUDIES

The experiment described herein studies the efficacy of the p-GlcNAc materials of the invention for the promotion of wound healing and the reduction of scar tissue.

22.1. MATERIALS AND METHODS p-GlcNAc membrane: p-GlcNAc membranes (2.0×2.0 cm) were used in this study. The p-GlcNAc was prepared using the chemical purification method described, above, in Section 5.3.2.

TABLE XIII

| Animal # Treatment | Tumor Volume Pre-Treatment (mm³) | Tumor Volume Post-treatment (mm³) | % Change | Comments |
| --- | --- | --- | --- | --- |
| A. 0.5x Dose: | | | | |
| 1. 5'-FU (.5x) | 169.0 | — | — | Died post-op |
| 2. 5'-FU (.5x) | 785.0 | 401.9 | −48 | |
| 3. 5'-FU (.5x) | 863.0 | 141.3 | −83 | |
| Average per Animal | | | | −65.5 |
| B. 1x Dose: | | | | |
| 4. 5'-FU (1.0x) | 269.0 | 98 | −63 | Died Day 8 post membrane |
| 5. 5'-FU (1.0x) | 269.0 | — | — | Died Post-Op |
| 6. 5'-FU (1.0x) | 401.9 | 62 | −84 | Died Day 8 post membrane |
| Average per Animal | | | | −73.5 |
| C. 2x Dose: | | | | |
| 7. 5'-FU (2.0x) | 401.9 | 98.0 | −75 | Died Day 8 post membrane |
| 8. 5'-FU (2.0x) | 785 | 50.24 | −93 | Died Day 8 post membrane |
| 9. 5'-FU (2.0x) | 572 | — | — | Died post-op |
| Average per Animal | | | | −84.0 |
| D. p-GlcNAc Control: | | | | |
| 10. p-GlcNAc Control | 401.9 | 785.0 | +190 | |
| 11. p-GlcNAc Control | 1356.5 | 1140.0 385.0 | +30 | 2nd mass |
| Average per Animal | | | | +110 |
| E. No Treatment Control: | | | | |
| 12. No Treatment | 401.9 | 1020.5 | +250 | |
| 13. No Treatment | 50.0 | 572.0 | +1100 | |
| Average per Animal | | | | +675 |

21.3. CONCLUSION

As is shown in Section 21.2, above, each of the disks (i.e., 1× and 2×) were very effective in reducing tumor size. While the 0.5× dose disks did so with little noticeable toxicity, the 1× and 2× dose disks resulted in significant mortality rates. This is presumably due to the higher effective 5'-FU dose being delivered to the animals. Thus, according to this data, it appears that doses smaller than conventional doses (in this case half the conventional dose) provide site-delivery effective in reducing tumor size without toxic effects.

Furthermore, preparation of the disks as described in this Example, in comparison to the Example presented in Section 20, below, appears to produce disks with less variability in dosage. This observation is based on the lack of toxicity Test Animals: Four healthy 23–27 kg, 13 week old Yorkshire pigs were used in the study. The animals were held in quarantine for seven days prior to the surgical procedure. Each animal was identified with an individual permanent ear tag.

Experimental Design: Four healthy Yorkshire pigs were used with each animal serving as its own control. Under general anesthesia four 2.0×2.0 cm serosal abrasion lesions were created on the surface of the intestine in each animal. Lesions 1 and 3 were left as untreated control sites, while sites 2 and 4 were each topically treated with the test article. Animals were recovered for 21 days at which time they were reanesthetized. The abdomen was explored and the abrasion sites were examined macroscopically for hemorrhaging, necrosis, discolorations and fibroblasts. Tissue samples were collected for histomicroscopy and scanning electron microscopy. The animals were anesthetized using a combination of xylazine (3.5–5.5 mg/kg, body weight) and Telazol (5.5–8.0 mg/kg, body weight) administered intra-muscularly. Animals were then incubated and maintained under general anesthesia using halothane and oxygen.

Surgical Procedure: With the animal under general anesthesia and in drosal recumbency, the ventral abdomen was aseptically prepared for surgery. The abdomen was clipped and then a gross and sterile scrub was performed using povidone iodine and 70% isopropyl alcohol. The animal was then draped for surgery. A 12 cm ventral midline celiotomy was made. Four (2.0×2.0 cm) serosal abrasions were created by lightly passing a new scalpel blade (#10 Bard-Parker blade, using 1 blade/site) across the serosal surface for 200 counts. Lesions created consisted of uniformly distributed minute, petechial hemorrhages. The first two lesions were created on the antimesenteric serosal surface of the small intestine and the remaining two were created on the antimesenteric serosal surface of the spiral colon. The margins of each lesion site were identified by using 4 peripherally placed sutures of 3-0 nylon. Sites 1 and 3 were left untreated and sites 2 and 4 were treated with the test article. The abdomen was closed using PDS and stainless steel staples for skin closure.

Clinical Observations were performed and recorded daily.

Euthanasia was achieved by administering an overdose of barbiturate while the animal was under general anesthesia on Day 21. The procedure was performed following the American Veterinary Medical Association guidelines.

22.2. RESULTS

Figure 32A:
FIG. 32A. Photograph of p-GlcNAc-treated site of Yorkshire pig abdomen 21 days after four 2.0×2.0 cm serosal abrasion lesions were created.
Figure 32B:
FIG. 32B. Photograph of non-treated-control site of Yorkshire pig abdomen 21 days after four 2.0×2.0 cm serosal abrasion lesions were created.

The treatment with the p-GlcNAc membrane was beneficial in promoting wound healing and reducing scar tissue formation. Macroscopically, the non-treated control sites were characterized by extensive fibrosis and discoloration. In contrast, the p-GlcNAc treated sites developed healthy tissue and very limited fibrosis. Representative findings are illustrated in FIG. 32A and 32B. (The spots are the remains of the suture material that was used to identify the margins of the lesions.) Histomicroscopy and scanning electron microscopy findings were consistent with the macroscopic observations.

23. EXAMPLE: TAXOL FORMULATION

Presented in this Example is a method of preparing various concentrations of taxol-pGlcNAc formulations.

23.1. MATERIALS AND METHODS p-GlcNAc starting material: An aqueous p-GlcNAc suspension (1.0–1.1 mg/ml mixture) was used. 0.70 ml of the aqueous p-GlcNAc solution was filtered using a glass filtered disk funnel and a 0.8 micron, 47 mm membrane filter. After approximately 5–6 minutes on the filtering apparatus, the membrane filter, containing the p-GlcNAc, was removed and placed in a clean petri dish. Using a clean scalpel and forceps, the p-GlcNAc was scraped gently from the membrane and placed into a 2 ml cryovial. At this time, the appropriate amount of taxol (6 mg/ml) and $H_2O$ (deionized and distilled) was added to the p-GlcNAc in the cryovial.

For example, as shown in Table XIV, below, to prepare a 1× disk containing 0.21 mg of taxol, 35 µl of taxol (6 mg/ml taxol solution) and 105 µl of $H_2O$ were added. The cryovial was then securely capped and the contents vortexed until a thick Slurry formed. The slurry was then placed into a well of a 48-well plate, and flattened using a glass stirring rod. The above procedure was then repeated until the desired number of p-GlcNAc disks were prepared.

After all the disks were placed in the 48-well plate, the plate was covered with Parafilm™ and the contents were frozen for at least one hour. Then, the disks were lyophilized overnight (approximately sixteen hours). Using a sterile needle, the disks were freed from the 48-well plate and flattened using the bottom of a clean dish and light pressure by hand. Disks were stored in clean petri dishes and labeled. It should be noted that autoclaving (e.g., 20 min, 121° C.) the disks does not harm them.

Similarly, a 2× formulation containing 0.42 mg of taxol, was prepared as above, except that 70 µl of taxol (mg/ml taxol solution) and 105 µl $H_{23}O$ was added to the p-GlcNAc in the cryovial. Table XIV, below, summarizes various taxol/p-GlcNAc formulations.

TABLE XIV

| Dose of Taxol | p-GlcNAc | $H_2O$ added |
|---|---|---|
| Controls - No Taxol | 7 ml p-GlcNAc | 140 µl $H_2O$ |
| 1X - 35 µl (0.21 mg) Taxol | 7 ml p-GlcNAc | 105 µl $H_2O$ |
| 2X - 70 µl (0.42 mg) Taxol | 7 ml p-GlcNAc | 70 µl $H_2O$ |
| 4X - 140 µl (0.84 mg) Taxol | 7 ml p-GlcNAc | 0 µl $H_2O$ |

It is apparent that many modifications and variations of this invention as set forth here may be made without departing from the spirit and scope thereof. The specific embodiments described above are given by way of example only, and the invention is limited only by the terms of the appended claims.

What is claimed is:

1. An anti-tumor drug/poly-β-1→4-N-acetylglucosamine composition comprising poly-β-1→4-N-acetylglucosamine comprising about 4,000 to about 150,000 N-acetylglucosamine monosaccharides covalently attached in a β-1→4 conformation, free of protein, substantially free of other organic contaminants, substantially free of inorganic contaminants, and having a molecular weight of about 800,000 daltons to about 30 million daltons within which an anti-tumor drug is encapsulated.

2. The anti-tumor drug/poly-β-1→4-N-acetylglucosamine composition of claim 1 wherein at least one N-acetylglucosamine monosaccharide has been deacetylated.

3. The anti-tumor drug/poly-β-1→4-N-acetylglucosamine composition of claim 1 or 2 wherein the anti-tumor drug is 5'-fluorouracil, mitomycin, cis-platin, taxol, adriamycin, actinomycin, a bleomycin, a daunomycin or a methamycin anti-tumor drug.

4. An anti-tumor drug poly-β-1→4-glucosemine composition comprising poly-β-1→4-glucosamine comprising about 4,000 to about 150,000 glucosamine monosaccharides covalently attached in a β-1→4 conformation, free of protein, substantially free of other organic contaminants, substantially free of inorganic contaminants and having a molecular weight of about 640,000 daltons to about 24 million daltons within which an anti-tumor drug is encapsulated.

5. The anti-tumor drug/poly-β-1→4-glucosamine composition of claim 4 wherein the anti-tumor drug is 5'-fluorouracil, mitomycin, cis-platin, taxol, adriamycin, actinomycin, a bleomycin, a daunomycin or a methamycin anti-tumor drug.

6. An anti-tumor drug/poly-β-1→4-N-acetylglucosamine composition comprising poly-β-1→4-N-acetylglucosamine of about 4,000 to about 150,000 N-acetylglucosamine monosaccharides covalently attached in a β-1–4 conformation, free of protein, Substantially free of other organic contaminants, substantially free of inorganic contaminants, and having a molecular weight of about 800,000 daltons to about 30 million daltone wherein at least one N-acetylglucosamine monosaccharide has been deacetylated, and where at least one anti-tumor drug is functionally attached to the deacetylated monosaccharide of the poly-β-1→4-N-acetylglucosamine.

7. The anti-tumor drug/poly-β-1→4-N-acetylglucosamine composition of claim 6 wherein the drug is a peptide covalently attached to the deacetylated monosaccharide.

8. The anti-tumor drug/poly-β-1→4-N-acetylglucosamine composition of claim 6 wherein the drug is a peptide non-covalently attached to a deacetylated monosaccharide.

9. An anti-tumor drug/poly-β-1→4glucosamine composition comprising about 4,000 to about 150,000 glucosamine monosaccharides covalently attached in a β-1→4 conformation, free of protein, substantially free of other organic contaminants, substantially free of inorganic contaminants and having a molecular weight of about 640,000 daltons to about 24 million daltons wherein at least one glucosamine monosaccharide of the poly-β-1→4-glucosamine contains an anti-tumor drug functionally attached thereto.

10. The anti-tumor drug/poly-β-1→4-glucosamine composition of claim 9 wherein the drug is a peptide covalently attached to the glucosamine monosaccharide.

11. The anti-tumor drug/poly-β-1→4-glucosamine composition of claim 9 wherein the drug is a peptide non-covalently attached to the glucosamine monosaccharide.

12. A method for anti-tumor drug delivery comprising: administering to a patient the anti-tumor drug/poly-β-1→4-N-acetylglucosamine composition of claim 1 or 2 so that, upon administration, the drug is released into the system of the patient as the poly-β-1→4-acetylglucosamine degrades.

13. A method for anti-tumor drug delivery comprising: administering to a patient the anti-tumor drug/poly-β-1→4-glucosamine of claim 4 or 5 so that, upon administration, the drug is released into the system of the patient as the poly-β-1→4-glucosamine degrades.

14. A method for anti-tumor drug delivery comprising: administering to a patient the anti-tumor drug/poly-β-1→4-N-acetylglucosamine composition of claim 6, 7 or 8 so that, upon administration, the attached anti-tumor drug is released as the poly-β-1→4-acetyl-glucosamine degrades.

15. A method for anti-tumor drug delivery comprising: administering to a patient the anti-tumor drug/poly-β-1→4-glucosamine composition of claim 9, 10 or 11 so that, upon administration, the attached anti-tumor drug moiety is released as the poly-β-1→4-glucosamine degrades.

16. A method for anti-tumor drug delivery comprising: administering to a patient the anti-tumor drug/poly-β-1→4-glucosamine composition of claim 3 so that, upon administration, the drug is released into the system of the patient as the poly-β-1→4-acetylglucosamine degrades.

* * * * *